United States Patent
Sinha et al.

(10) Patent No.: US 9,587,233 B2
(45) Date of Patent: *Mar. 7, 2017

(54) ANTIDOTES FOR FACTOR XA INHIBITORS AND METHODS OF USING THE SAME

(71) Applicant: PORTOLA PHARMACEUTICALS, INC., South San Francisco, CA (US)

(72) Inventors: Uma Sinha, San Francisco, CA (US); Genmin Lu, Burlingame, CA (US); Pamela B. Conley, Palo Alto, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/790,305

(22) Filed: Jul. 2, 2015

(65) Prior Publication Data

US 2016/0002617 A1 Jan. 7, 2016

Related U.S. Application Data

(60) Continuation of application No. 13/591,098, filed on Aug. 21, 2012, now Pat. No. 9,109,046, which is a division of application No. 12/749,217, filed on Mar. 29, 2010, now Pat. No. 8,268,783, and a continuation-in-part of application No. 12/239,651, filed on Sep. 26, 2008, now Pat. No. 8,153,590.

(60) Provisional application No. 61/164,886, filed on Mar. 30, 2009, provisional application No. 60/976,343, filed on Sep. 28, 2007, provisional application No. 61/090,574, filed on Aug. 20, 2008.

(51) Int. Cl.
| | |
|---|---|
| C07K 14/755 | (2006.01) |
| C12N 9/64 | (2006.01) |
| A61K 38/48 | (2006.01) |
| A61K 47/48 | (2006.01) |
| C07K 14/745 | (2006.01) |
| A61K 39/00 | (2006.01) |

(52) U.S. Cl.
CPC .......... *C12N 9/6432* (2013.01); *A61K 38/482* (2013.01); *A61K 38/4826* (2013.01); *A61K 38/4833* (2013.01); *A61K 38/4846* (2013.01); *A61K 38/4853* (2013.01); *A61K 47/48215* (2013.01); *C07K 14/745* (2013.01); *C12Y 304/21006* (2013.01); *A61K 39/00* (2013.01)

(58) Field of Classification Search
None
See application file for complete search history.

(56) References Cited

U.S. PATENT DOCUMENTS

| | | | |
|---|---|---|---|
| 5,278,144 A | 1/1994 | Wolf | |
| 5,298,599 A | 3/1994 | Rezaie et al. | |
| 5,516,650 A | 5/1996 | Foster et al. | |
| 5,589,571 A | 12/1996 | King | |
| 5,589,572 A | 12/1996 | King | |
| 5,597,799 A | 1/1997 | Wolf | |
| 5,602,233 A | 2/1997 | King | |
| 5,770,699 A | 6/1998 | King | |
| 5,795,863 A * | 8/1998 | Wolf | C07K 14/745 424/94.64 |
| 5,817,309 A | 10/1998 | Nowak et al. | |
| 5,939,304 A | 8/1999 | Suzuki et al. | |
| 6,060,300 A | 5/2000 | Raditsch et al. | |
| 6,069,234 A | 5/2000 | Chmielewska et al. | |
| 6,086,871 A | 7/2000 | Fischer et al. | |
| 6,376,515 B2 | 4/2002 | Zhu et al. | |
| 6,472,562 B1 | 10/2002 | Klingler et al. | |
| 6,660,885 B2 | 12/2003 | South et al. | |
| 6,835,739 B2 | 12/2004 | Zhu et al. | |
| 7,220,569 B2 | 5/2007 | Himmelspach et al. | |
| 7,220,849 B2 | 5/2007 | High et al. | |
| 7,247,654 B2 | 7/2007 | Priestley et al. | |
| 7,598,276 B2 | 10/2009 | Grant et al. | |
| 8,153,590 B2 * | 4/2012 | Lu | A61K 38/4826 424/185.1 |
| 8,268,783 B2 * | 9/2012 | Sinha | A61K 38/4826 424/185.1 |
| 8,455,439 B2 * | 6/2013 | Lu | A61K 35/16 424/94.64 |

(Continued)

FOREIGN PATENT DOCUMENTS

| | | |
|---|---|---|
| CA | 2156991 | 2/1996 |
| DE | 4430205 | 2/1996 |

(Continued)

OTHER PUBLICATIONS

Skogen et al., "Comparison of coagulation factor Xa and des-(1-44)factor Xa in the assembly of prothrombinase" J Biol Chem. Feb. 25, 1984;259(4):2306-10.*
U.S. Appl. No. 07/808,329, filed Dec. 16, 1991, Wolf.
Agnelli, et al., "A phase II study of the oral factor Xa inhibitor LY517717 for the prevention of venous thromboembolism after hip or knee replacement," *J. Thromb. Haemost.*, (2007), 5(4):746-753.
Ansell, et al., "The Pharmacology and Management of the Vitamin K Antagonists: The Seventh ACCP Conference on Antithrombotic and Thrombolvtic Therapy," *Chest*, (2004), 126:204-233.
Bajaj, et al., "Decarboxylation of γ-Carboxyglutamic Acid Residues in Human Prothrombin," *J. Biol. Chem.*, (1982), 257(7):3726-3731.
Betz, et al., "Inhibition of factor Xa by a Peptidyl-α-ketothiazole Involves Two Steps. Evidence for a Stabilizing Conformational Change," *Biochem.*, (1999), 38(44):14582-14591.
Bijsterveld, et al., "Ability of Recombinant Factor VIIa to Reverse the Anticoagulant Effect of the Pentasaccharide Fondaparinux in Healthy Volunteers," *Circulation*, (2002), 106:2550-2554.

(Continued)

*Primary Examiner* — Michael Szperka
(74) *Attorney, Agent, or Firm* — Sheppard Mullin Richter & Hampton LLP

(57) ABSTRACT

The present invention relates antidotes to anticoagulants targeting factor Xa. The antidotes are factor X and factor Xa protein derivatives that bind to the factor Xa inhibitors thereby substantially neutralizing them but do not assemble into the prothrombinase complex. The derivatives describe herein lack or have reduced intrinsic coagulant activity. Disclosed herein are methods of reversing anticoagulation, stopping or preventing bleeding in a patient that is currently undergoing anticoagulant therapy with a factor Xa inhibitor.

7 Claims, 13 Drawing Sheets

(56) References Cited

U.S. PATENT DOCUMENTS

| | | | |
|---|---|---|---|
| 8,455,441 B2* | 6/2013 | Lu | A61K 38/4826 424/185.1 |
| 8,889,129 B2* | 11/2014 | Lu | A61K 38/4826 424/185.1 |
| 9,056,106 B2* | 6/2015 | Sinha | A61K 38/4846 |
| 9,062,298 B2* | 6/2015 | Lu | A61K 38/4826 424/185.1 |
| 9,109,046 B2* | 8/2015 | Sinha | A61K 38/4826 |
| 9,388,401 B2* | 7/2016 | Lu | A61K 38/4826 |
| 2003/0064414 A1 | 4/2003 | Benecky et al. | |
| 2003/0181381 A1 | 9/2003 | Himmelspach | |
| 2003/0207796 A1 | 11/2003 | Sinha et al. | |
| 2004/0198660 A1 | 10/2004 | Petersen et al. | |
| 2013/0129693 A1 | 5/2013 | Sinha et al. | |

FOREIGN PATENT DOCUMENTS

| | | |
|---|---|---|
| EP | 1820508 A | 8/2007 |
| WO | WO-96/00577 | 1/1996 |
| WO | WO-98/38317 | 9/1998 |
| WO | WO-98/38318 | 9/1998 |
| WO | WO-98/39456 | 9/1998 |
| WO | WO-2007/059513 | 5/2007 |
| WO | WO-2007/096116 | 8/2007 |
| WO | WO-2008/084106 | 7/2008 |
| WO | WO-2009/042962 | 4/2009 |
| WO | WO-2010/056765 | 5/2010 |
| WO | WO 2010/070137 | 6/2010 |
| WO | WO-2011/008885 | 1/2011 |

OTHER PUBLICATIONS

Bijsterveld, et al., "Neutralization of the anticoagulant effect of fondaparinux by recombinant activated factor VII in healthy male volunteers", European Heart Journal, (2002), 23(725): Abstract No. P3701.

Brandstetter, et al., "X-ray Structure of Active Site-inhibited clotting Factor Xa," J. Bio. Chem., (1996), 271 (47):29988-29992.

Camire, et al. "Protothrombinase Assembly and S1 Site Occupation Restore the Catalytic Acitivty of FXa Impaired by Mutation at the Sodium binding Site," Journal of Biological Chemistry, (2002), 277(40):37863-37870.

Camire, et al., "Enhance γ-Carboxylation of Recombinant Factor X Using a Chimeric Construct Containing the Prothrombin Propeptide," Biochem., (2000), 39:14322-14329.

Chang, et al. "Low Molecular Weight Protamine as Nontoxic Heparin/Low Molecular Weight Heparin Antidote (III): Preliminary in Vivo Evaluation of Efficacy and Toxicity Using a Canine Model," AAPS Phannsci., (2001), 3(2):1-8: Article 19.

Elg, et al., "Effects of Agents, Used to Treat Bleeding Disorders, on Bleeding Time Prolonged by a Very High Dose of a Direct Thrombin Inhibitor in Anesthesized Rats and Rabbits," Thrombosis Research, (2001) 101:159-170.

Eriksson, et al., "YM150, an Oral Direct Factor Xa Inhibitor, as Prophylaxis for Venous Thrombeombolism in Patients with Elective Primary Hip Replacement Surgery. A dose Escalation Study," Blood, (2005), 106(11 ), Abstract 1865; Retrieved online from [http://abstracts.hematologylibrary.org/cgi/content/abstract/106/11/1865?maxtoshow=&HITS=10&hits=10&RESULTFORMAT=&fulltext=YM150&searchid=1&FIRSTINDEX=0&volume=106&issu e=11&resourcetype=HWCIT].

Gerotziafas, et al., "Recombinant factor VIIa partially reverses the inhibitory effect of fondaparinaux on thrombin generation after tissue factor activation in platelet rich plasma and whole blood,"Thrombosis and Haemostasis, (2004), 91 :531-537.

Haverkamp, et al., "The use of specific antidotes as a response to bleeding complications during anticoagulant therapy for venous thromboembolism," Journal of Thrombostasis and Haemostasis, (2003), 1 :69-73.

Herbert, et al., "Dx 9065A, a Novel, Synthetic, Selective and Orally Active Inhibitor of Factor Xa: In Vitro and in Vivo Studies," J Pharmacol Exp Ther., (1996), 276(3):1030-1038.

Hirsh, et al., "Heparin and Low-Molecular Weigh Heparin: The Seventh ACCP Conference on Antithrombotic and Thrombolytic Therapy," Chest, (2004), 126:5188-5203.

Hollenbach, et al., "A Comparative Study of Prothrombinase and Thrombin Inhibitors in a Novel Rabbit Model of Non-Occlusive Deep Vein Rhrombosis," Thromb. Haemost., (1994), 71 (3), 357-362.

Hulin, et al., "A Novel Protamine Variant Reversal of Heparin Anticoagulation in Human Blood in Vitro," Journal of Vascular Surgery, C.V. Mosby Co., St. Louis, MO, US. (1997), 26(6): 1043-1048.

International Preliminary Report on Patentability for International Application No. PCT/US2010/029064, dated Jun. 28, 2011, 17 pages.

International Search Report and Written Opinion for PCT/US2010/029064 dated Sep. 7, 2010, 9 pages.

Izaguirre, et al. "Mechanism by Which Exosites Promote the Inhibition of Blood Coagulation Proteases by Heparin-activated Antithrombin," J. Boil. Chem., (2007), 282, 33609-33622.

Jesty, et al., "The Activation of Coagulation Factor X: Identity of Cleavage Sites in the Alternative Activation Pathways and Characterization of the COOH-Terminal Peptide," J. Biol. Chem., (1975), 250(12):4497-4504.

Kubitza, et al., "Safety, pharmacodynamics, and pharmacokinetics of BAY 59-7939—an oral, direct factor Xa inhibitor—after multiple dosing in healthy male subjects," Eur. J. Clin. Pharmacol., (2005), 61 :873-880.

Larson, et al., "Structure/Function Analyses of Recombinant Variants of Human Factor Xa: Factor Xa Incorporation into Prothrombinase on the Thrombin-Activated Platelet Surface Is Not Mimicked by Synthetic Phospholipid Vesicles," Biochem., (1998), 37:5029-5038.

Lauritzen, et al., "Recombinant Human FVIIa Reduces Heparin and Low Molecular Weight Heparin (LMWH)—Induced in Rats," Blood, (2005), 106:607A-608A: Abstract No. 2149.

Levi, et al., "Recombinant Factor VIIa as an Antidote for Anticoagulant Treatments" Seminars in Hematology, (2004), 41(1):(Suppl) 65-69.

Leytus, et al., "Gene for Human Factor X: a Blood Coagulation Factor Whose Gene Organization is Essentially Identical with That of Factor IX and Protein C," Biochemistry, (1986), 25:5098-5102.

Lin, et al., "Reversible Acylation of Factor Xa as a Potential Therapy for Hemophilia," Thrombosis Res., (1997), 88(4):365-372.

Lisman, et al., "Recombinant factor VIIa reverses the in vitro and ex vivo anticoagulant and profibrinolytic effects of fondaparinux," Journal of Thrombosis and Haemostasis, (2003), 1:2368-22373.

Lu, et al., "Recombinant Antidote for Reversal of Anticoagulation by Factor Xa Inhibitors", Blood, (2008), 112(11):362.

Luettgen, et al., "In Vitro Evaluation of Apixoban, a Novel, Potent, Selective and Orally Bioavailable Factor Xa Inhibitor," Blood, (2006), 108(11): abstract 4130 Retrieved online from [http://abstracts.hematologylibrary.org/cgi/content/abstract/108/11/4130?maxtoshow=&HITS=10&hits=10&RESULTFORMAT=&fulltext=Evaluation+of+Apixaban&searchid=1&FIRSTINDEX=0&volume=108&issue=11&resourcetype=HWCIT].

Mann, et al., "Surface-Dependent Reactions of the Vitamin K-Dependent Enzyme Complexes," Blood, (1990), 76(1):1-16.

Marlu, et al.,"Gla-domainless factor Xa: molecular bait to bypass a blocked tenase complex," Haematologica, (2012), 97(8):1165-72.

Maroney, et al., "Absence of hematopietuc tissue factor pathway inhibitor mitigates bleeding in mice with hemophilia," PNAS, (2012). 109-3927-31.

Morita, et al., "Preparation and Properties of Derivatives of Bovine factor X and Factor Xa from which the γ-Carboxyglutamic Acid Containing Domain Has been Removed," J. Bio. Chem., (1986), 261 (9):4015-4023.

National Center for Biotechnology Information [Online], Genbank Entrez CoreNucleotide Accession No. NM_000504 [Retrieved on Dec. 9, 2008] Retrieved from the Internet: [http://www.ncbi.nlm.nih.gov/entrez/viewer.fcgi?d b=nuccore&id=89142731].

(56) References Cited

OTHER PUBLICATIONS

Nogami, et al., "Mechanisms of Interactions of Factor X and Factor Xa with the Acidic Region in the Factor VIII A1 Domain," *J. Biol. Chem.*, (2004), 279(32):33104-33113.

Nogami, et al., "Role of factor VIII C2 domain in factor VIII Binding to Factor Xa," *J. Biol. Chem.*, (1999), 274(43):31000-31007.

Nowak, et al., "The Ecarin Clotting Time, A Universal Method to Quantify Direct Thromibin Inhibitors" *Pathophysiology of Haemostasis and Thrombosis*, (2003), 33: 173-183.

Office Action, dated Oct. 30, 2013, in corresponding Mexican Patent Application No. Mx/a/2010/003095, with translation, 4 pages.

Pabinger, et al., "Prothrombin Complex Concentrate (Beriplex® P/N) for Emergency Anticoagulation Reversal: A Prospective Multinational Clinical Trial," *Journal of Thrombosis and Haemostasis*, (2008), 6:622-631.

Padmanabhan, et al., "Structure of Human Des(145) Factor Xa at -22 Å Resolution," *Journal Mol. Biol.*, (1993), 232:947-966.

Peraramelli et al., "The Kunitz 1 and Kunitz 3 domains of tissue factor pathway inhibitor are required for efficient inhabitation of factor Xa," Thrombosis and Haemostasis, (2012), 108(2):266-276.

Perzborn, et al. "In Vitro and in vivo studies of the novel antithrombotic agent BAY 59-7939-an oral, direct factor Xa inhibitor," *J. Thromb. Haemost.*, (2005), 3:514-521.

Petersen, et al., "Effect of Leukocyte Proteinases on Tissue Factor Pathway Inhibitor," *Thrombosis and Haemostasis*, (1992), 67(5):537-541.

Pinto, et al. "Discovery of 1-(4-Methoxyphenyl) 7 oxo 6 (4 (2 oxopiperidin-1-yl)phenyl)-4,5,6, 7- tetrahydro-1H-pyrazolo[3,4-c]pyridine-3-carboxamide (Apixaban, BMS-562247), a Highly Potent, Selective, Efficacious, and Orally Bioavailable Inhibitor of Blood Coagulation Factor Xa," *J. Med. Chem.*, (2007), 55(22):5339-5356.

Pryzdial, et al., "Autoproteolysis or Plasmin-mediated Cleavage of Factor Xaα Exposes a Plasminogen Binding Site and Inhibits Coagulation," *J Biol Chem.*, (1996), 271(28):16614-20.

Reutelingsperger, et al., "Purification and characterization of a novel protein from bovine aorta that inhibits coagulation: Inhibition of the phospholipid-dependent factor Xa-catalyzed prothrombin activation through a high affinity binding of the anticoagulant to the phospholipids," *European Journal of Biochemistry*, (1988), 173:171-178.

Rezaie, et al., "Contribution of Residue 192 in Factor Za to Enzyme Specificity and Function," *The Journal of Biological Chemistry*, (1995), 270927):16176-16181.

Rezaie, et al., "Analysis of the Function of the First Epidermal Growth Factor-like Domainof Factor X," *The Journal of Biological Chemistry*, (1993), 268(11):8176-8180.

Rochrig, et al., "Discovery of the Novel Antithrombotic Agent 5-Chloro N ({(5S) 2 oxo 3 [4 (3 oxomorphalin-4-yl)phenyl)-1,3-oxazolidin-5-yl}methyl)thriophene-2carboxamide (BAY 59-7939): An Oral, Direct Factor Xa Inhibitor," *J. Med. Chem.*, (2005), 48(19):5900-5908.

Rudolph, et al., "Definition of a Factor Va Binding Site in Factor Xa," *J. Biol. Chem.*, (2001), 276(7):5123-5128.

Rudolph, et al., "Substitution of asparagine for arginine 347 of recombinant factor Xa markedly reduces factor Va binding," *Biochem.*, (2000), 39(11 ):2861-2867.

Samama, et al., "Biochemistry and clinical pharmacology of new anticoagulant agents," *Pathophysiology of Thrombosis and Haemostasis*, (2002), 32:218-224.

Schulmann, et al., "Anticoagulants and Their Reversal," *Transfusion Medicine Reviews*, (2006), 21(1): 37-48.

Sinha et al., Expression, purification, and characterization of inactive human coagulation factor Xa (Asn322Ala419) Protein Expression and Purif., (1992), 3:518-524.

Sinha, et al., "Effect of Gamma Carboxylation on Prothrombinase Inhibitory Activity of Catalytically Inactive Factor Xa," *Thrombosis Research*, (1994), 75:427-436.

Skogen, et al., "Comparision of coagulation factor Xa and Des-(1-44)factor Xa in the assembly of prothrombinase," *J. Biol. Chem.*, (1984), 259(4):2306-2310.

Skolnick, et al., "From Genes to Protein Structure and Function: Novel Application of Computational Approaches in Genomic Era," *Trends in Biotechnology*, (2000), 18:34-39.

Taniuchi, et al. "Biochemical and pharmacological Characterization of YM-60828, a Newly Synthesized and Orally Active Inhibitor of Human Factor Xa," *Thromb Haemost.*, (1998), 79(3):543-548.

Tinel, et al., "Partial Reversal of the Anticoagulant Effect of High-Dose Rivaroxa ban an Oral, Direct Factor Xa Inhibitor—by Recombinant Factor VIIa in Rats.," *Blood*, (2006), 108(11):274A, Part 1, XP009115120.

Turpie, et al. "BAY 59-7939: an oral, direct Factor Xa inhibitor for the prevention of venous thromboembolism in patients after total knee replacement. A phase II dose-ranging study," *J. Thromb. Haemost.*, (2005), 3(11):2479-2486.

US Notice of Allowance in U.S. Appl. No. 13/414,499 dated Feb. 7, 2013, 4 pages.

US Noticeof Allowance in U.S. Appl. No. 12/749,217 dated May 24, 2012, 12 pages.

US Office Action dated in U.S. Appl. No. 13/414,499 dated Oct. 23,2012 4 pages.

Venkateswarlu, et al., "Structure and Dynamics of Zymogen Human Blood Coagulation Factor X," *Biophysical Journal*, (2002), 82: 1190-1206.

Viles-Gonzalez, et al., "Clinical and Experimental Experience with Factor Xa Inhibitors," *American Journal of Cardiovascular Drugs*, (2004), 4(6):379-384.

Warkentin, et al., "Reversing Anticoagulants Both Old and New," *Canadian Journal of Anesthesia*, (2002), 49:6:S11-S25.

Whisstock, et al., "Prediction of Protein Function from Protein Sequence and Structure," *Quarterly Reviews of Biophysics*, (2003), 36:307-340.

Wolf, et al., "Procoagulant activity of reversibly acylated human factor Xa," *Blood*, (1995), 86(11):4153-4157.

Yang, et al., "Antibodies Against the Activated Coagulation Factor X (FXa) in the Antiphospholipid Syndrome that Interfere With the FXa Inactivation by Antithrombin," *J. Immunol.*, (2006), 177(11):1-17.

Yegneswaran, et al., "Identification of Distinct Sequences in Human Blood Coagualtion Factor Xa and Prothrombin Essential for Substrate and Cofactor Recognition in the Prothrombinase Complex," *J. Biol. Chem.*, (2003), 278(35):33312-33318.

Young, et al., "Recombinant activated factor VII effectively reverses the anticoagulant effects of heparin, enoxaparin, fondaparinux, argatroban, and bivalirudin ex vivo as measured using thromboelastoqraphy," *Blood Coagulation & Fibroniolysis*, (2007), 18(6):547-553.

Hylek, "Drug Evaluation: DU-176b, an oral, direct Factor Xa Antagonist", Current Opinion in Investinational Drugs, 2007, vol. 8, No. 9, pp. 778-783.

Levi, "Emergency Reversal of Antithrombotic Treatment", Intern Emerg Med, 2009, vol. 4, pp. 137-145.

Pryzdial et al., "Kinetics of Blood Coagulation Factor Xa alpha Autoproteolytic Conversion to Factor XaBeta", 1996, The Journal of Biological Chemistry, vol. 271, No. 28, 1996, pp. 16621-16626.

Young et al., "Selective and Dual Action Orally Active Inhibitors of Thrombin and Factor Xa", 2007, Bioorganic and Medicial Chemistry Letters, vol. 17, pp. 2927-2930.

* cited by examiner

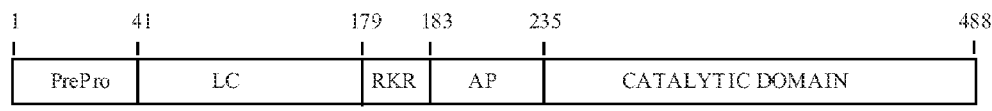
FIG. 1
FIG. 2
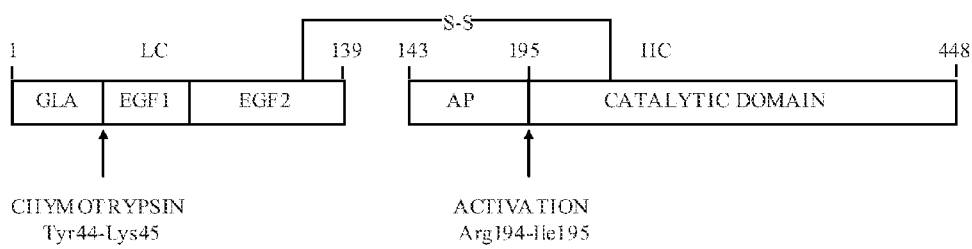
FIG. 3

```
atgggcgcccactgacctcgtcctgctcagtgcctccctggctggcctcctgctgctc
 M  G  R  P  L  H  L  V  L  L  S  A  S  L  A  G  L  L  L  L
gggaaagtctgttcatccgcagggagcaggccaacaacatcctggcgagggtcacgagg
 G  E  S  L  F  I  R  R  E  Q  A  N  N  I  L  A  R  V  T  R
gccaattccttcttttctggaataaatacaaagatggcgaccagtgtgagaccagtcct
 A  N  S  F  L  F  W  N  K  Y  K  D  G  D  Q  C  E  T  S  P
tgccagaaccagggcaaatgtaaagacggcctcggggaatacacctgcacctgtttagaa
 C  Q  N  Q  G  K  C  K  D  G  L  G  E  Y  T  C  T  C  L  E
ggattcgaaggcaaaaactgtgaattattcacacggaagctctgcagcctggacaacggg
 G  F  E  G  K  N  C  E  L  F  T  R  K  L  C  S  L  D  N  G
gactgtgaccagttctgccacgaggaacagaactctgtggtgtgctctgcccgcggg
 D  C  D  Q  F  C  H  E  E  Q  N  S  V  V  C  S  A  R  G
tacaccctggctgacaacggcaaggctgcattccacagggccctaccctgtgggaaa
 Y  T  L  A  D  N  G  K  A  C  I  F  T  G  P  Y  P  C  G  K
cagaccctggaacgcaggaagaggaggaagaggatcgtggaggccaggaatgcaaggac
 Q  T  L  E  R  R  K  R  R  K  R  I  V  G  G  Q  E  C  K  D
ggggagtgcccctggcaggccctgctcatcaatgaggaaaacgagggtttctgtggtgga
 G  E  C  P  W  Q  A  L  L  I  N  E  E  N  E  G  F  C  G  G
accattctgagcgagttctacatcctaacggcagccactgtctctaccaagccaagaga
 T  I  L  S  E  F  Y  I  L  T  A  A  H  C  L  Y  Q  A  K  R
ttcaaggtgagggtaggggaccggaacacggagcaggaggaggcggtgagcggtgcac
 F  K  V  R  V  G  D  R  N  T  E  Q  E  E  G  G  E  A  V  H
gaggtggaggtggtcatcaagcacaacaacggttcacaaaggagacctatgactcgacatc
 E  V  E  V  V  I  K  H  N  R  F  T  K  E  T  Y  D  F  D  I
gccgtgctccggctcaagacccccatcaccttccgcatgaacgtggccgctgcctgctc
 A  V  L  R  L  K  T  P  I  T  F  R  M  N  V  A  P  A  C  L
cccgagcgtgactggccgagtccacgctgatgacgcagaagacggggattgtgagcggc
 P  E  R  D  W  A  E  S  T  L  M  T  Q  K  T  G  I  V  S  G
ttcgggcgcacccacgagaagggccggcagtccaccaggctcaagatgctggaggtgccc
 F  G  R  T  H  E  K  G  P  Q  S  T  R  L  K  M  L  E  V  P
tacgtggaccgcaacagctgcaagctgtccagcagcttcatcatcacccagaacatgttc
 Y  V  D  P  N  S  C  K  L  S  S  S  F  I  I  T  Q  N  M  F
tgtgcgggctacgacaccaagcaggaggatgcctgccaggggacgcaggggcccccgcac
 C  A  G  Y  D  T  K  Q  E  D  A  C  Q  G  D  A  G  G  P  H
gtcaccgcttcaaggacacctactttgtgacaggcatcgtcagctggggagagggctgt
 V  T  R  F  K  D  T  Y  F  V  T  G  I  V  S  W  G  E  G  C
gcccgtaaggggaagtacggatctacaccaaggtcaccgccttcctcaagtggatcgac
 A  R  K  G  K  Y  G  I  Y  T  K  V  T  A  F  L  K  W  I  D
aggtccatgaaaaccaggggcttgcccaaggccaagagccatgccccggagtcataacg
 R  S  M  K  T  R  G  L  P  K  A  K  S  H  A  P  E  V  I  T
tcctctccattaaagtga
 S  S  P  L  K  -
```

FIG. 21

ANTIDOTES FOR FACTOR XA INHIBITORS AND METHODS OF USING THE SAME

CROSS-REFERENCE TO RELATED APPLICATIONS

This application is a continuation of U.S. application Ser. No. 13/591,098, filed Aug. 21, 2012, now U.S. Pat. No. 9,109,046 issued Aug. 18, 2015, which is a divisional of U.S. application Ser. No. 12/749,217, filed Mar. 29, 2010, now U.S. Pat. No. 8,268,783 issued Sep. 18, 2012; which claims the benefit under 35 U.S.C. §119(e) of U.S. Provisional Patent Application 61/164,886, filed Mar. 30, 2009. This application also is a continuation-in-part of U.S. Ser. No. 12/239,651, filed on Sep. 26, 2008, which application claimed the benefit under 35 U.S.C. §119(e) of U.S. Provisional Patent Application Ser. Nos. 60/976,343 and 61/090,574, filed Sep. 28, 2007 and Aug. 20, 2008, respectively. All of the above-listed patent applications are hereby incorporated by reference in their entirety.

FIELD OF INVENTION

The present invention relates to the use of factor X (fX) and factor Xa (fXa) derivatives having reduced or lacking intrinsic procoagulant activity but are also capable of binding and/or neutralizing fXa inhibitors thereby acting as antidotes to anticoagulants targeting fXa.

SEQUENCE LISTING

The instant application contains a Sequence Listing which has been submitted in ASCII format via EFS-Web and is hereby incorporated by reference in its entirety. Said ASCII copy, created on Nov. 7, 2012, is named 0705451802.txt and is 97,900 bytes in size.

BACKGROUND OF THE INVENTION

Anticoagulants serve a need in the marketplace in treatment or prevention of undesired thrombosis in patients with a tendency to form blood clots, such as, for example, those patients having clotting disorders, confined to periods of immobility or undergoing medical surgeries. One of the major limitations of anticoagulant therapy, however, is the bleeding risk associated with the treatments, and limitations on the ability to rapidly reverse the anticoagulant activity in case of overdosing or if an urgent surgical procedure is required. Thus, specific and effective antidotes to all forms of anticoagulant therapy are highly desirable. For safety considerations, it is also advantageous to have an anticoagulant-antidote pair in the development of new anticoagulant drugs.

Currently available anticoagulant-antidote pairs for over-anticoagulation are heparin—protamine and warfarin—vitamin K. Fresh frozen plasma and recombinant factor VIIa (rfVIIa) have also been used as non-specific antidotes in patients under low molecular weight heparin treatment, suffering from major trauma or severe hemorrhage. (Lauritzen, B. et al, *Blood,* 2005, 607A-608A.) Also reported are protamine fragments (U.S. Pat. No. 6,624,141) and small synthetic peptides (U.S. Pat. No. 6,200,955) as heparin or low molecular weight heparin antidotes; and thrombin muteins (U.S. Pat. No. 6,060,300) as antidotes for thrombin inhibitors. Prothrombin intermediates and derivatives have been reported as antidotes to hirudin and synthetic thrombin inhibitors (U.S. Pat. Nos. 5,817,309 and 6,086,871).

One promising form of anticoagulant therapy targets factor Xa (fXa), and in fact, several direct fXa inhibitors are currently in different stages of clinical development for use in anticoagulant therapy. One direct fXa inhibitor Xarelto™ (rivaraoxaban) has been approved for clinical use in the European Union and Canada for the prevention of venous thromboembolism in orthopedic surgery patients. Many of these are small molecules. While these new fXa inhibitors show promise for treatment, specific and effective antidotes are still needed. In cases of over-anticoagulation or requirement for surgery in patients treated with these fXa inhibitors, an agent may be required to substantially neutralize the administered fXa inhibitor or inhibitors and restore normal hemostasis.

Currently available agents, such as recombinant factor VIIa (rfVIIa), are mechanistically limited and not specific for reversal of fXa inhibitors and thus improved options for the clinician are highly desirable. In human studies, rfVIIa has been used to reverse the effect of indirect antithrombin III dependent fXa inhibitors such as fondaparinux and idraparinux (Bijsterveld, N R et al, *Circulation,* 2002, 106: 2550-2554; Bijsterveld, N R et al, *British J. of Haematology,* 2004(124): 653-658). The mechanism of action of factor VIIa (fVIIa) is to act with tissue factor to convert factor X (fX) present in blood circulation to fXa to restore normal hemostasis in patients. This mode of action necessarily dictates that the highest potential concentration of fXa that could be attained to neutralize active site directed fXa inhibitors is limited by the circulating plasma concentration of fX. Since the circulating plasma concentration of fX is 150 nanomolar ("nM"), the maximal amount of fXa produced by this mode would be 150 nM. Thus, the potential of using rfVIIa to reverse the effect of direct fXa inhibitors is mechanistically limited. Reported therapeutic concentrations of small molecule fXa inhibitors such as rivaroxaban have been higher (approximately 600 nM, Kubitza D, et al, *Eur. J. Clin. Pharmacol.,* 2005, 61:873-880) than the potential amount of fXa generated by rfVIIa. Use of rfVIIa for reversal of therapeutic or supratherapeutic levels of anticoagulation by fXa inhibitor would therefore provide inadequate levels of efficacy. As shown in FIG. 4, using rfVIIa has limited effect in neutralizing the anticoagulant activity of a factor Xa inhibitor betrixaban (described below). Recombinant fVIIa showed a dose responsive antidote activity from 50 nM to 100 nM, but the effect leveled off between 100 nM to 200 nM, indicating that its antidote effect is limited by factors other than its concentration. In all of the rfVIIa concentrations tested, betrixaban still showed a dose responsive inhibition of fXa, up to about 75% inhibition at a concentration of 250 nM. This observation is consistent with fVIIa's proposed mechanism of action. This is also supported by studies showing that rfVIIa did not completely reverse the inhibitory effect of fondaparinux on the parameters of thrombin generation and prothrombin activation. (Gerotiafas, G T, et al, *Thrombosis & Haemostasis* 2204 (91):531-537).

Exogenous active fXa cannot be administered directly to a subject in a way similar to rfVIIa. Unlike rfVIIa, which has very low procoagulant activity in the absence of its cofactor tissue factor, native fXa is a potent enzyme and has a potential risk of causing thrombosis. Thus, the use of either rfVIIa or active fXa as an antidote to a fXa anticoagulant therapy has disadvantages.

Thus, there is a need for improved antidote agents that do not cause undesired thrombosis and that are effective in substantially neutralizing the anticoagulant activity of a fXa inhibitor in the event of an overdose of the fXa inhibitor or in the event that normal hemostasis needs to be restored to prevent or stop bleeding.

Any and all publications, patents, patent applications mentioned herein are hereby incorporated by reference in their entirety.

SUMMARY OF THE INVENTION

It has now been discovered that administration of modified derivatives of fX proteins are useful as antidotes to anticoagulants targeting fXa. The modified derivatives of fX proteins do not compete with fXa in assembling into the prothrombinase complex, but instead bind and/or substantially neutralize the anticoagulants, such as fXa inhibitors. The derivatives useful as antidotes are modified to reduce or remove intrinsic procoagulant and anticoagulant activities, while retaining the ability to bind to the inhibitors. It is contemplated that the derivatives of the invention may include modifying the active site and changing or removing the entire Gla domain from fXa. It is further contemplated that modification of the Gla domain reduces or removes the anticoagulant effect of the fX derivative on normal hemostasis because an active site modified full length fXa is known to be an anticoagulant.

Thus, in one embodiment, the invention is directed to an isolated polypeptide factor X derivative comprising a modified active site and a modified or deleted Gla domain. It is contemplated that the derivative binds to a factor Xa inhibitor and does not assemble into a prothrombinase complex.

Additional modifications to the derivative include, but are not limited to the following: all or part of the activation peptide is deleted at an N-terminus of a heavy chain; the derivative has an amino acid modification which prevents cleavage of a β-peptide; a β-peptide is deleted; modification of an EGF domain; the derivative comprises a signal peptide; there is a mutation in the autolysis loop of the factor Xa heavy chain; and/or the linker that connects the light chain to the activation peptide is modified.

In one embodiment, the derivative maintains the structural characteristics necessary for binding the anticoagulant (or fXa inhibitor) targeting fXa. By the derivative binding, either directly or indirectly, to the inhibitor, the inhibitor is substantially neutralized.

In one aspect, the invention provides a method of neutralizing or reversing anticoagulation in a subject undergoing anticoagulant therapy with a factor Xa inhibitor who is in need of cessation of anticoagulation or suffering from bleeding. The method comprises administering to the subject an effective amount of a factor X derivative that binds to the factor Xa inhibitor but does not assemble into the prothrombinase complex. In one embodiment, the derivative has either reduced or no procoagulant activity. The derivative of the invention selectively binds and inhibits an exogenously administered factor Xa inhibitor thereby substantially neutralizing the anticoagulant activity of a fXa inhibitor. This method contemplates both in vitro and in vivo methods. It is further contemplated that the methods of the invention are also directed to preventing or reducing bleeding in a subject undergoing anticoagulant therapy with a factor Xa inhibitor.

It is to be understood that the derivatives contemplated by this invention are not plasma derived factor VIIa, recombinant factor VIIa, fresh frozen plasma, prothrombin complex concentrates, or whole blood.

One aspect of the present invention is the use of the factor X derivatives and compositions containing the same to treat patients who have received or are receiving over-anticoagulation therapy with a factor Xa inhibitor or patients who had previously been administered a factor Xa inhibitor and is then in need of hemostasis, such as required by elective or emergency surgery. In one aspect, the fX derivatives are distinguished from naturally occurring fX or fXa in that they have reduced or removed intrinsic procoagulant activity and will not interfere with physiological fXa function in hemostasis, while still capable of binding and substantially neutralizing fXa inhibitors.

In another aspect, the modified factor X protein is co-administered with an agent capable of extending the plasma half life (or circulating half life) of the factor X derivative. In yet another aspect, the antidote is conjugated with a moiety to extend its plasma half-life.

Also provided are pharmaceutical compositions that contain the factor X derivative that binds (and/or substantially neutralizes) the factor Xa inhibitor but does not assemble into the prothrombinase complex. The pharmaceutical composition optionally comprises a pharmaceutically acceptable carrier.

In another aspect, this invention provides a kit comprising a fX inhibitor for anticoagulant use and a fXa inhibitor antidote (or factor Xa derivative) for use when substantial neutralization of the fXa inhibitor's anticoagulant activity is needed.

One embodiment of the invention is directed to an isolated polypeptide comprising the amino acid sequence of SEQ ID NO. 12, 13, 15, 19, 20, 21, 22, 23, 24, or 25 or a polypeptide having at least 80% homology to 12, 13, 15, 19, 20, 21, 22, 23, 24, or 25. The polypeptides encompassed by the invention include both the single chain polypeptide (i.e., before the polypeptide is excreted from the cell) as well as the two-chain polypeptide (i.e., after cleavage at the linker after it is secreted from the cell).

It is contemplated that the polypeptides of SEQ ID NOs. 19 to 25 improve overall expression of the functional antidote and/or reduce heterogeneity at the C-terminus of the heavy chain.

Also provided is a pharmaceutical composition comprising a carrier and a polypeptide just described.

Also provided is a polynucleotide encoding for a polypeptide just described.

Further provided herein is a peptide conjugate comprising a carrier covalently or non-covalently linked to a polypeptide just described. The carrier can be a liposome, a micelle, a pharmaceutically acceptable polymer, or a pharmaceutically acceptable carrier.

This invention is also directed to an antibody that binds a polypeptide just described. The antibody is a polyclonal antibody, a monoclonal antibody, a chimeric antibody or a humanized antibody. Also provided is a biologically active fragment of the antibody. The antibody may be detectably labeled. The antibody (or antibody fragment) is also provided as part of a composition further comprising a carrier.

In one embodiment there is provided an antibody-peptide complex comprising the antibody of invention and a polypeptide that specifically binds to the antibody. The polypeptide is the polypeptide against which the antibody is raised. The antibody may be a polyclonal antibody, a monoclonal antibody, a chimeric antibody or a humanized antibody.

In another embodiment, there is provided a method for preparing a polypeptide of the invention comprising expressing a polynucleotide encoding the polypeptide in a prokaryotic or eukaryotic host cell. In one embodiment, the host cell is a eukaryotic cell and in particular is a Chinese hamster ovary cell. In another embodiment, the polypeptide is isolated.

In yet another embodiment, there is provided an isolated prokaryotic or eukaryotic host cell comprising a polynucleotide encoding polypeptide of the invention. In one embodiment, the host cell is in a composition further comprising a carrier.

In still yet another embodiment, there is provided a method of preventing or reducing bleeding in a subject undergoing anticoagulant therapy with a factor Xa inhibitor comprising administering to the subject an effective amount of a composition comprising a polypeptide of the invention and a carrier. Further provided is a method of selectively binding and inhibiting an exogenously administered factor Xa inhibitor in a subject undergoing anticoagulant therapy comprising administering to the subject an effective amount of a composition just described.

BRIEF DESCRIPTION OF THE DRAWINGS

FIG. 1 shows schematically the domain structure of human factor X (SEQ ID NO. 1) shown in Table 1 as reported in Leytus et al, *Biochem.*, 1986, 25, 5098-5102. SEQ ID NO. 1 is the amino acid sequence of human fX coded by the nucleotide sequence of human fX (SEQ ID NO. 2) as shown in Table 2 known in the prior art. For example, the translated amino acid sequence is reported in Leytus et al, *Biochem.*, 1986, 25, 5098-5102 and can be found in GenBank, with accession number "NM_000504". The amino acid numbering in this sequence is based on fX sequence. Human fX precursor (SEQ ID NO. 1) contains a prepro-leader sequence (amino acids 1 to 40 of SEQ ID NO. 1) followed by sequences corresponding to the fX light chain (LC) (amino acids 41 to 179 of SEQ ID NO. 1), the RKR triplet (amino acids 180 to 182 of SEQ ID NO. 1) which is removed during fX secretion, and the fX heavy chain (amino acids 183 to 488 of SEQ ID NO. 1, SEQ ID NO: 40) containing the activation peptide 8 (AP) (amino acids 183 to 234 of SEQ ID NO. 1) and the catalytic domain (amino acids 235 to 488 of SEQ ID NO. 1).

FIG. 2 (SEQ ID NO. 3) shows the amino acid sequence of mature human factor X. The amino acid numbering in this figure is based on fX sequence starting from the N-terminal of fX light chain. Factor X circulates in plasma as a two-chain molecule linked by a disulfide bond. The light chain (LC) has 139 amino acid (amino acids 41 through 179 of SEQ ID NO. 1) residues and contains the γ-carboxyglutamic acid (Gla)-rich domain (amino acids 1-45 of SEQ ID NO. 3), including a short aromatic stack (AS) (amino acids 40-45 of SEQ ID NO. 3), followed by two epidermal growth factor (EGF)-like domains (EGF1: amino acids 46-84, EGF2: amino acids 85-128 of SEQ ID NO. 3). The heavy chain (HC) has 306 amino acids and contains a 52 amino acids activation peptide (AP: amino acids 143-194 of SEQ ID NO. 3) followed by the catalytic domain (amino acids 195-448 of SEQ ID NO. 3). The catalytic triad equivalents to H57-D102-S195 in chymotrypsin numbering are located at His236, Asp282, and Ser379 in fX sequence and are underlined (amino acids 236, 282 and 379 of SEQ ID NO. 3).

FIG. 3 shows schematically the domain structure of mature human factor X shown in FIG. 2. The amino acid numbering in this figure is based on mature fX sequence. The cleavage sites for chymotrypsin digestion to remove the Gla-domain containing fragment (amino acid 1-44 of SEQ ID NO. 3) and fX activation to remove the activation peptide are highlighted. Chymotrypic digestion of fXa results in a Gla-domainless fXa lacking the 1-44 amino acid residues (SEQ ID NO. 4).

FIGS. 18 and 19 are discussed in Example 11.

FIG. 21 shows the alignment of the polynucleotide sequence (SEQ ID NO: 16) and translated polypeptide sequence (SEQ ID NO: 43) of r-Antidote.

As shown in FIG. 22A, a single IV injection of r-Antidote increased betrixaban level in plasma by more than 8 fold compared to vehicle control (control_1), indicating the ability of the antidote to effectively bind betrixaban in vivo. A second injection of the antidote further increased betrixaban level by less than 2 fold compared to the single injection, indicating limiting amount of betrixaban in mouse blood and reversal of its anticoagulant effect by the antidote.

DETAILED DESCRIPTION OF THE INVENTION

I. Definitions

Figure 4:
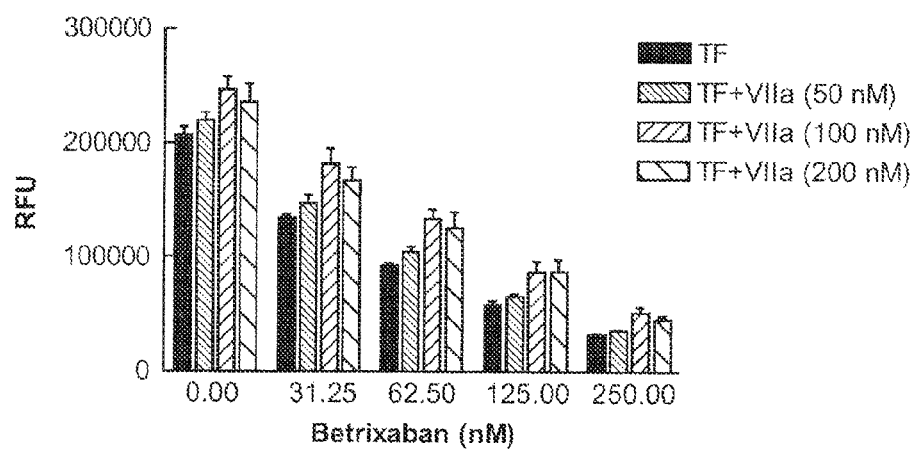
FIG. 4 shows the effect of varying concentrations of rfVIIa (referred to as VIIa in the figure) in the presence of tissue factor (TF) on the anticoagulant activity of a fXa inhibitor betrixaban (described below) in a thrombin generation (expressed as relative fluorescence units (RFU) assay as described in Example 2). The data show that a combination of rfVIIa and tissue factor was unable to completely neutralize the anticoagulant activity of a fXa inhibitor, betrixaban, in concentrations up to 200 nM of rVIIa.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3$^{rd}$ edition (Cold Spring Harbor Laboratory Press (2002)).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "subject" of diagnosis or treatment is a cell or a mammal, including a human. Non-human animals subject to diagnosis or treatment include, for example, murine, such as rats, mice, canine, such as dogs, leporids, such as rabbits, livestock, sport animals, and pets.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. Single letter and three letter abbreviations of the naturally occurring amino acids are listed below. A peptide of three or more amino acids is commonly called an oligopeptide if the peptide chain is short. If the peptide chain is long, the peptide is commonly called a polypeptide or a protein.

| 1-Letter | 3-Letter | Amino Acid |
|---|---|---|
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine |

"Factor Xa" or "fXa" or "fXa protein" refers to a serine protease in the blood coagulation pathway, which is produced from the inactive factor X (fX). Factor Xa is activated by either factor IXa with its cofactor, factor VIIIa, in a complex known as intrinsic Xase, or factor VIIa with its cofactor, tissue factor, in a complex known as extrinsic Xase. fXa forms a membrane-bound prothrombinase complex with factor Va and is the active component in the prothrombinase complex that catalyzes the conversion of prothrombin to thrombin. Thrombin is the enzyme that catalyzes the conversion of fibrinogen to fibrin, which ultimately leads to blood clot formation. Thus, the biological activity of fXa is sometimes referred to as "procoagulant activity" herein.

Factor Xa is a two chain molecule linked by one disulfide bond between the two chains. The heavy chain contains the serine protease, trypsin-like active site and the N-terminal activation peptide which is glycosylated. The heavy chain has at least three forms, α, β, and γ, which differ due to the cleavage of a C-terminal peptide in the heavy chain (Aronson, D. L. et al. *Proc. Soc. Exp. Biol. Med.* 137(4):1262-1266 (1971); Mertens, K. Et al., *Biochem. J.* 185:647-658 (1980)). This is further discussed in sections describing fX and fXa derivatives.

The nucleotide sequence coding human factor X ("fX") can be found in GenBank, with accession number "NM 000504", and is listed in FIG. 1b and SEQ ID No. 2. The corresponding amino acid sequence and domain structure of fX are described in Leytus et al, *Biochemistry*, 1986, 25:5098-5102. The domain structure of mature fX is also described in Venkateswarlu, D. et al, *Biophysical Journal*, 2002, 82:1190-1206. Upon catalytic cleavage of the first 52 residues (amino acids 143 to 194 of SEQ ID NO. 3) of the heavy chain, fX is activated to fXa (SEQ ID NO. 6). FXa contains a light chain (SEQ ID NO. 8) and a heavy chain (SEQ ID NO. 9). The first 45 amino acid residues (residues 1-45 of SEQ ID NO. 6) of the light chain is called the Gla domain because it contains 11 post-translationally modified γ-carboxyglutamic acid residues (Gla). It also contains a short (6 amino acid residues) aromatic stack sequence (residues 40-45 of SEQ ID NO. 6). Chymotrypsin digestion selectively removes the 1-44 residues resulting Gla-domain-less fXa (SEQ ID NO. 4). The serine protease catalytic domain of fXa locates at the C-terminal heavy chain. The heavy chain of fXa is highly homologous to other serine proteases such as thrombin, trypsin, and activated protein C.

The domain structure of mature factor X may be found in Venkateswarlu D. et al, *Biophysical J.*, 2002, 82, 1190-1206, which is hereby incorporated by reference in its entirety. The amino acid numbering in this figure is the same as in FIG. 3. The tripeptide of Arg140-Lys141-Arg142 (SEQ ID NO: 40) (the RKR triplet (SEQ ID NO: 40) as shown in FIG. 1) that connects the light chain to the activation peptide is not shown because the form that lacks the tripeptide is predominant incirculation blood plasma. Individual domains are shown in boxes. This includes amino acids 1-45 in FIG. 2 (SEQ ID NO. 3). Functionally important catalytic residues are circled, and "g" represents Gla (g-carboxyglutamic acid) residue.

"Native fXa" or "wild-type fXa" refers to the fXa naturally present in plasma or being isolated in its original, unmodified form, which processes the biological activity of activating prothrombin therefore promoting formation of blood clot. The term includes naturally occurring polypeptides isolated from tissue samples as well as recombinantly produced fXa. "Active fXa" refers to fXa having the biological activity of activating prothrombin. "Active fXa" may be a native fXa or modified fXa that retains procoagulant activity.

"fX Derivatives" or "modified fXa" derivatives refers to fX proteins that have been modified such that they bind, either directly or indirectly, to a factor Xa inhibitor and do not assemble into the prothrombinase complex. Examples include, but are not limited to, the polypeptide in SEQ ID NO. 19. Included within the definition of fX derivatives are fXa derivatives discussed below. In some embodiments, the modified derivative may also use the term "Factor Xai".

"fXa Derivatives" or "modified fXa" or "derivatives of a factor Xa protein" refers to fXa proteins that have been modified such that they bind, either directly or indirectly, to a factor Xa inhibitor and do not assemble into the prothrombinase complex. Structurally, the derivatives are modified to provide either no procoagulant activity or reduced procoagulant activity. "Procoagulant activity" is referred to herein as an agent's ability to cause blood coagulation or clot formation. Reduced procoagulant activity means that the procoagulant activity has been reduced by at least about 50%, or more than about 90%, or more than about 95% as compared to wild-type fXa during the same period. For example, recombinant fX-S395A essentially has no procoagulant activity as measured by in vitro assays, such as fXa activity assays.

The derivatives have modified active sites and a modified Gla domain. Additional modifications are also contemplated. It is contemplated that such modifications may be made in one or more of the following ways: deletion of one or more of the amino acid from the sequence, substitution of one or more amino acid residues with one or more different amino acid residues, and/or manipulation of one or more amino acid side chains or its "C" or "N" terminals.

The term "active site" refers to the part of an enzyme or antibody where a chemical reaction occurs. A "modified active site" is an active site that has been modified structurally to provide the active site with increased or decreased chemical reactivity or specificity. It is contemplated that the active site includes not only the actual site but also a domain containing the active site. Examples of active sites include, but are not limited to, the catalytic domain of human factor X comprising the 235-488 amino acid residues (FIG. 1), and the catalytic domain of human factor Xa comprising the 195-488 amino acid residues (FIGS. 2 and 3). The catalytic triad equivalent to H57-D102-S195 in chymotrypsin numbering are located at His236, Asp282, and Ser379. Examples of modified active site include, but are not limited to, the catalytic triad residues individually or in combination. One modification relates to a fXa derivative having a modified active site Ser379/A. Additional examples, include modifications to the catalytic domain of human factor Xa comprising 195-448 amino acid residues in SEQ ID NOS. 10, 11, 12, 13, or 15 with at least one amino acid substitution at position Arg306, Glu310, Arg347, Lys351, Lys414, or Arg424.

As stated above, the derivatives of the invention may have modified Gla domains or have the entire Gla domain removed. Examples of fXa derivatives suitable as antidotes in the methods of this invention are Gla-domainless fX (SEQ ID NO. 19), Gla-domainless fXa (SEQ ID NOS. 4, 5, 20, 21, 22, 23, 24, or 25), Gla-deficient fXa (SEQ ID NO. 7 with modifications described herein), fXa with modifications at the catalytic site (SEQ ID NOS. 10 or 11), and fXa with modifications at the sites known to be important for fV/fVa interaction or fVIII/fVIIIa interaction (SEQ ID NOS. 4, 5, 7, 10, or 11 with at least one amino acid substitution at position Arg306, Glu310, Arg347, Lys351, Lys414 or Arg424), as described in detail herein. Further examples of the fX and fXa derivatives contemplated by this invention are provided below.

"Gla-domainless" or "des-Gla" refers to fXa or fX that does not have a Gla-domain and encompasses fXa and fX derivatives bearing other modification(s) in addition to the removal of the Gla-domain. Examples of Gla-domainless fXa in this invention include, but are not limited to, fXa derivative lacking the 1-39 amino acid residues of SEQ ID NO. 3; fXa derivative lacking the 6-39 amino acid residues of SEQ ID NO. 3, corresponding to a fXa mutant expressed in CHO cells described in more details below (SEQ ID NO. 12, Table 12); fXa derivative lacking the 1-44 amino acid residues of SEQ ID NO. 3, corresponding to des-Gla fXa after chymotryptic digestion of human fXa (SEQ ID NO. 4, FIG. 3); and fXa derivative lacking the entire 1-45 Gla-domain residues of SEQ ID NO. 3 as described in Padmanabhan et al, *Journal Mol. Biol.*, 1993, 232:947-966 (SEQ ID NO 5). Other examples include des-Gla anhydro fXa (SEQ ID NO. 10, Table 10) and des-Gla fXa-S379A (SEQ ID NO. 11, Table 11).

In some embodiments, the des-Gla fXa comprises at least amino acid residues 40 to 448 of SEQ ID NO. 3 or an equivalent thereof. In some embodiment, the des-Gla fXa comprises at least amino acid residues 45 to 488 (SEQ ID NO. 4) or 46 to 488 (SEQ ID NO. 5) of SEQ ID NO. 3 or equivalents thereof.

In some embodiment, the des-Gla fXa comprises at least amino acid residues 40 to 139 and 195 to 448 of SEQ ID NO. 3 or equivalents thereof. In some embodiment, the des-Gla fXa comprises at least amino acid residues 45 to 139 and 195 to 448 of SEQ ID NO. 3 or equivalents thereof. In another embodiment, the des-Gla fXa comprises at least amino acid residues 46 to 139 and 195 to 448 of SEQ ID NO. 3 or equivalents thereof.

"Gla-deficient" refers to fXa or fX with reduced number of free side chain γ-carboxyl groups in its Gla-domain. Like Gla-domainless fXa, Gla-deficient fXa can also bear other modifications. Gla-deficient fXa includes uncarboxylated, undercarboxylated and decarboxylated fXa. "Uncarboxylated fXa" or "decarboxylated fXa" refers to fXa derivatives that do not have the γ-carboxy groups of the γ-carboxyglutamic acid residues of the Gla domain, such as fXa having all of its Gla domain γ-carboxyglutamic acid replaced by different amino acids, or fXa having all of its side chain γ-carboxyl removed or masked by means such as amination, esterification, etc. For recombinantly expressed protein, uncarboxylated fXa is, sometimes, also called non-carboxylated fXa. "Undercarboxylated fXa" refers to fXa derivatives having reduced number of γ-carboxy groups in the Gla domain as compared with wild-type fXa, such as fXa having one or more but not all of its Gla domain γ-carboxyglutamic acids replaced by one or more different amino acids, or fXa having at least one but not all of its side chain γ-carboxyl removed or masked by means such as amination and esterification, etc.

The domain structure of human Gla-domainless factor Xa may be found in Padmanabhan et al., *J. Mol. Biol.*, 1993, 232, 947-966, which is hereby incorporated by reference in its entirety. The numbering of the amino acid is based on topological equivalences with chymotrypsin, where, for example, Ser195 corresponds to Ser379 in FIG. 2 when the human mature fX numbering is used. Insertions are indicated with letters, and deletions are indicated by 2 successive numberings. 300 are added to light chain numbering to differentiate from the heavy chain numbering. β363 is β-hydroxy aspartate. Slashes indicate proteolytic cleavages observed in crystallized material. The sequence of Gla-domainless fXa lacking the 1-45 amino acid residues based mature fX (SEQ ID NO. 3) is listed in SEQ ID NO. 5.

In one embodiment of the invention, all or part of the "activation peptide" (AP) is removed. What is meant by activation peptide is amino acids 183 to 234 of SEQ ID NO. 1 or alternatively, amino acids 143-194 of SEQ ID NO. 3.

In another embodiment, a signal peptide is included in the derivative. The term "signal peptide" refers to a factor X signal peptide (SEQ ID NO. 18), a transferrin signal peptide (amino acid residues SP1 to SP19 of SEQ ID NO. 27), or a prothrombin signal peptide (amino acid residues SP1 to SP24 of SEQ ID NO. 26).

In one embodiment, the fXa derivative may lack a light chain of fXa but still contains a serine protease catalytic domain present in the heavy chain. In addition chimeras with other serine protease catalytic domain may be used to make substitutions in the heavy chain.

A "β-peptide" refers to all or a portion of the heavy chain.

"pd-Antidote" or "plasma-derived antidote" refers to the des-Gla anhydro fXa derivative and has the amino acid residues of SEQ ID NO. 10.

"r-Antidote" or "recombinant antidote" refers to a fXa derivative lacking the 6-39 amino acid residues of SEQ ID NO. 3, corresponding to a fXa mutant expressed in CHO cells and after removal of the linker described in more detail below (SEQ ID NO. 13, Table 13).

"Anticoagulant agents" or "anticoagulants" are agents that inhibit blood clot formation. Examples of anticoagulant agents include, but are not limited to, specific inhibitors of thrombin, factor IXa, factor Xa, factor XIa, factor XIIa or factor VIIa, heparin and derivatives, vitamin K antagonists, and anti-tissue factor antibodies. Examples of specific inhibitors of thrombin include hirudin, bivalirudin (Angiomax®), argatroban and lepirudin (Refludan®). Examples of heparin and derivatives include unfractionated heparin (UFH), low molecular weight heparin (LMWH), such as enoxaparin (Lovenox®), dalteparin (Fragmin®), and danaparoid (Organan®); and synthetic pentasaccharide, such as fondaparinux (Arixtra®). Examples of vitamin K antagonists include warfarin (Coumadin®), phenocoumarol, acenocoumarol (Sintrom®), clorindione, dicumarol, diphenadione, ethyl biscoumacetate, phenprocoumon, phenindione, and tioclomarol. In one embodiment, the anticoagulant is an inhibitor of factor Xa. In one embodiment, the anticoagulant is betrixaban.

"Anticoagulant therapy" refers to a therapeutic regime that is administered to a patient to prevent undesired blood clots or thrombosis. An anticoagulant therapy comprises administering one or a combination of two or more anticoagulant agents or other agents at a dosage and schedule suitable for treating or preventing the undesired blood clots or thrombosis in the patient.

The term "factor Xa inhibitors" or "inhibitors of factor Xa" refer to compounds that can inhibit, either directly or indirectly, the coagulation factor Xa's activity of catalyzing conversion of prothrombin to thrombin in vitro and/or in vivo. Examples of known fXa inhibitors include, without limitation, edoxaban, fondaparinux, idraparinux, biotinylated idraparinux, enoxaparin, fragmin, NAP-5, rNAPc2, tissue factor pathway inhibitor, DX-9065a (as described in, e.g., Herbert, J. M., et al, *J Pharmacol Exp Ther.* 1996 276(3):1030-8), YM-60828 (as described in, e.g., Taniuchi, Y., et al, *Thromb Haemost.* 1998 79(3):543-8), YM-150 (as described in, e.g., Eriksson, B. I. et. al, *Blood* 2005; 106 (11), Abstract 1865), apixaban, rivaroxaban, PD-348292 (as described in, e.g., Pipeline Insight: Antithrombotics—Reaching the Untreated Prophylaxis Market, 2007), otamixaban, razaxaban (DPC906), BAY 59-7939 (as described in, e.g., Turpie, A. G., et al, *J. Thromb. Haemost.* 2005, 3(11):2479-86), edoxaban (as described in, e.g., Hylek E M, Curr Opin Invest Drugs 2007 8(9):778-783), LY517717 (as described in, e.g., Agnelli, G., et al, *J. Thromb. Haemost.* 2007 5(4):746-53), GSK913893, betrixaban (as described below) and derivatives thereof. Low molecular weight heparin ("LMWH") is also considered a factor Xa inhibitor.

In one embodiment, the factor Xa inhibitor is selected from betrixaban, rivaroxaban, apixaban, edoxaban, LMWH, and combinations thereof.

The term "betrixaban" refers to the compound "[2-({4-[(dimethylamino)iminomethyl]phenyl}carbonylamino)-5-methoxyphenyl]-N-(5-chloro(2-pyridyl))carboxamide" or pharmaceutically acceptable salts thereof. "[2-({4-[(dimethylamino)iminomethyl]phenyl}carbonylamino)-5-methoxyphenyl]-N-(5-chloro(2-pyridyl))carboxamide" refers to the compound having the following structure:

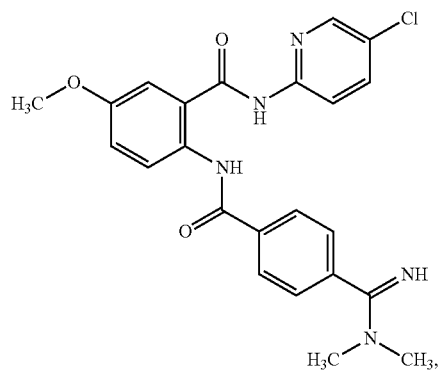 [SMILES: COc1ccc(NC(=O)c2ccc(C(=N)N(C)C)cc2)c(C(=O)Nc2ccc(Cl)cn2)c1]

or a tautomer or pharmaceutically acceptable salt thereof.

Betrixaban is described in U.S. Pat. Nos. 6,376,515 and 6,835,739 and U.S. Patent Application Publication No. 2007/0112039, filed on Nov. 7, 2006, the contents of which are incorporated herein by reference. Betrixaban is known to be a specific inhibitor of factor Xa.

As used herein, the term "antidote" or "antidote to a factor Xa inhibitor" refers to molecules, such as derivatives of fX or fXa, which can substantially neutralize or reverse the coagulation inhibitory activity of a fXa inhibitor by competing with active fXa to bind with available fXa inhibitors. Examples of the antidotes of this invention are fXa derivatives with reduced phospholipid membrane binding, such as des-Gla fXa or Gla-deficient fXa, and fXa derivatives with reduced catalytic activity, such as the active site modified fXa derivatives, and derivatives with reduced interaction with fVNa, or fVIII/fVIIIa. Examples of antidotes of the invention with reduced membrane binding and reduced catalytic activity include, but are not limited to, des-Gla anhydro-fXa by chymotryptic digestion of anhydro-fXa (as described in Example 1); des-Gla fXa-S379A (S195A in chymotrypsin numbering) by mutagenesis (as described in Example 6).

Other examples of antidotes of the invention include proteins or polypeptides containing serine protease catalytic domains which possess sufficient structural similarity to fXa catalytic domain and are therefore capable of binding small molecule fXa inhibitors. Examples include, but are not limited to, thrombin which binds to the fXa inhibitor GSK913893 (Young R., et al., *Bioorg. Med. Chem. Lett.* 2007, 17(10): 2927-2930); plasma kallikrein which binds to the fXa inhibitor apixaban (Luettgen J., et al., *Blood*, 2006, 108(11) abstract 4130); and trypsin (or its bacterial homolog subtilisin) which binds the fXa inhibitor C921-78 with subnanomolar affinity (Kd=500 pM) (Betz A, et al, *Biochem.*, 1999, 38(44):14582-14591).

In one embodiment, the derivative of the invention binds, either directly or indirectly to a factor Xa inhibitor. The terms "binding," "binds," "recognition," or "recognize" as used herein are meant to include interactions between molecules that may be detected using, for example, a hybridization assay. The terms are also meant to include "binding" interactions between molecules. Interactions may be, for example, protein-protein, protein-nucleic acid, protein-small molecule or small molecule-nucleic acid in nature. Binding may be "direct" or "indirect". "Direct" binding comprises direct physical contact between molecules. "Indirect" binding between molecules comprises the molecules having direct physical contact with one or more intermediate molecules simultaneously. For example, it is contemplated that derivatives of the invention indirectly bind and substantially neutralize low molecular weight heparin and other indirect inhibitors of factor Xa. This binding can result in the formation of a "complex" comprising the interacting molecules. A "complex" refers to the binding of two or more molecules held together by covalent or non-covalent bonds, interactions or forces.

"Neutralize," "reverse" or "counteract" the activity of an inhibitor of fXa or similar phrases refer to inhibit or block the factor Xa inhibitory or anticoagulant function of a fXa inhibitor. Such phrases refer to partial inhibition or blocking of the function, as well as to inhibiting or blocking most or all of fXa inhibitor activity, in vitro and/or in vivo. These terms also refer to corrections of at least about 20% of fXa inhibitor dependent pharmacodynamic or surrogate markers. Examples of markers include, but are not limited to INR, PR, aPTT, ACT, anti-fXa units, thrombin generation (Technothrombin TGA), thromboelastogrpahy, CAT (calibrated automated thrombogram) and the like.

In certain embodiments, the factor Xa inhibitor is neutralized substantially (or corrected as just described) meaning that its ability to inhibit factor Xa, either directly or indirectly, is reduced by at least about 5%, 10%, 15%, 20%, 25%, 30%, 35%, 40%, 45%, 50%, 55%, 60%, 65%, 70%, 75%, 80%, 85%, 90%, 95%, or 100%.

The term "phospholipid membrane binding" refers to an active fXa's ability to bind to the negatively charged phospholipid membrane or other cellular membrane, such as platelets, in the presence of $Ca^{2+}$ ions. This binding is mediated by the T-carboxyglutamic acid residues in the Gla domain of fXa.

The term "reduced interaction" refers to fXa derivative's diminished ability to bind or form a complex with ions or other co-factors which normally binds or complexes with wild fXa. Examples of such interaction include but are not limited to fXa's binding with $Ca^{q+}$ ions and phospholipid membrane, interaction with fV/fVa, or fVIII/f/VIIIa, etc. It is preferred that the interaction of a fXa derivative with the ions or other co-factors is reduced to 50% of that of a wild fXa. More preferably, the interaction is reduced to 10%, 1%, and 0.1% of that of a wild-type fXa. This refers to the derivatives' ability to "assemble into the prothrombinase complex."

"fXa inhibitor binding activity" refers to a molecule's ability to bind an inhibitor of fXa. An antidote of the present invention possesses fXa inhibitor binding activity, whether it is directly or indirectly.

The term "circulating half life" or "plasma half life" refers to the time required for the plasma concentration of an antidote that circulates in the plasma to reduce to half of its initial concentration after a single administration or following cessation of infusion.

The term "conjugated moiety" refers to a moiety that can be added to a fXa derivative by forming a covalent bond with a residue of the fXa derivative. The moiety may bond directly to a residue of the fXa derivative or may form a covalent bond with a linker which in turn forms a covalent bond with a residue of the fXa derivative.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The antibodies can be polyclonal or monoclonal and can be isolated from any suitable biological source, e.g., murine, rat, sheep and canine.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

"An effective amount" refers to the amount of derivative sufficient to induce a desired biological and/or therapeutic result. That result can be alleviation of the signs, symptoms, or causes of a disease, or any other desired alteration of a biological system. In the present invention, the result will typically involve one or more of the following: neutralization of a fXa inhibitor that has been administered to a patient, reversal of the anticoagulant activity of the fXa inhibitor, removal of the fXa inhibitor from the plasma, restoration of hemostasis, and reduction or cessation of bleeding. The effective amount will vary depending upon the specific antidote agent used, the specific fXa inhibitor the subject has been administered, the dosing regimen of the fXa inhibitor, timing of administration of the antidote, the subject and disease condition being treated, the weight and age of the subject, the severity of the disease condition, the manner of administration and the like, all of which can be determined readily by one of ordinary skill in the art.

Effective unit doses of the antidotes described herein are described in U.S. Provisional Application Ser. No. 61/225, 887, filed on Jul. 15, 2009 and entitled "Unit Dose Formulation of Antidotes for Factor Xa Inhibitors and Methods of Using the Same," which is hereby incorporated by reference in its entirety. Specifically, it is contemplated that the unit dose formulation comprising a pharmaceutically acceptable carrier and a two chain polypeptide comprising the amino acid sequence of SEQ ID NO. 13 or a polypeptide having at least 80% homology to SEQ ID NO. 13 is an amount from about 10 milligrams to about 2 grams or from about 100 milligrams to about 1.5 grams or from about 200 milligrams to about 1 gram or from about 400 milligrams to about 900 milligrams. It is further contemplated that other antidotes of the invention will be dosed in a similar manner.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

"Treating" also covers any treatment of a disorder in a mammal, and includes: (a) preventing a disorder from occurring in a subject that may be predisposed to a disorder, but may have not yet been diagnosed as having it, e.g., prevent bleeding in a patient with anticoagulant overdose; (b) inhibiting a disorder, i.e., arresting its development, e.g., inhibiting bleeding; or (c) relieving or ameliorating the disorder, e.g., reducing bleeding.

As used herein, to "treat" further includes systemic amelioration of the symptoms associated with the pathology and/or a delay in onset of symptoms. Clinical and subclinical evidence of "treatment" will vary with the pathology, the individual and the treatment. Further, the term "prevent" also refers to inhibiting.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art.

The agents and compositions of the present invention can be used in the manufacture of medicaments and for the treatment of humans and other animals by administration in accordance with conventional procedures, such as an active ingredient in pharmaceutical compositions.

An agent of the present invention can be administered for therapy by any suitable route, specifically by parental (including subcutaneous, intramuscular, intravenous and intradermal) administration. It will also be appreciated that the preferred route will vary with the condition and age of the recipient, and the disease being treated.

One can determine if the method, i.e., inhibition or reversal of a factor Xa inhibitor is achieved, by a number of in vitro assays, such as thrombin generation assay, and anti-fXa units, and clinical clotting assays such as aPTT, PT and ACT.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

As used herein, the term "equivalent thereof" when referring to a reference protein, polypeptide or nucleic acid, intends those having minimal homology while still maintaining desired functionality. It is contemplated that any modified protein mentioned herein also includes equivalents thereof. For example, the homology can be, at least 75% homology and alternatively, at least 80%, or alternatively at least 85%, or alternatively at least 90%, or alternatively at least 95%, or alternatively 98% percent homology and exhibit substantially equivalent biological activity to the reference polypeptide or protein. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. It should be noted that when only the heavy chain of fXa (or a related serine protease) is used, the overall homology might be lower than 75%, such as, for example, 65% or 50% however, the desired functionality remains. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the specified percent homology and encoding a polypeptide having the same or similar biological activity.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

"Liposomes" are microscopic vesicles consisting of concentric lipid bilayers. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, distearoylphosphatidylethanolamine (DSPE), dioleoylphosphatidylcholine (DOPC), dipalmitoylphosphatidylcholine (DPPC), palmitoyloleoyl-phosphatidylcholine (POPC), palmitoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol).

Negatively charged lipids include phosphatidic acid (PA), dipalmitoylphosphatidylglycerol (DPPG), dioleoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs).

A "micelle" is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody or composition described herein to facilitate efficient delivery to the target cell or tissue.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral particle that comprises a polynucleotide to be delivered into a host cell, either in vivo, ex vivo or in vitro.

Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., a cell surface marker found on stem cells or cardiomyocytes. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

The phrase "solid support" refers to non-aqueous surfaces such as "culture plates" "gene chips" or "microarrays." Such gene chips or microarrays can be used for diagnostic and therapeutic purposes by a number of techniques known to one of skill in the art. In one technique, oligonucleotides are arrayed on a gene chip for determining the DNA sequence by the hybridization approach, such as that outlined in U.S. Pat. Nos. 6,025,136 and 6,018,041. The polynucleotides of this invention can be modified to probes, which in turn can be used for detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarrays" and similar technologies are know in the art. Examples of such include, but are not limited to, LabCard (ACLARA Bio Sciences Inc.); GeneChip (Affymetrix, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarrying system that can dispense from 12 to 64 spots onto multiple glass slides (Intelligent Bio-Instruments); Molecular Biology Workstation and Nano-Chip (Nanogen, Inc.); a microfluidic glass chip (Orchid biosciences, Inc.); BioChip Arrayer with four PiezoTip piezoelectric drop-on-demand tips (Packard Instruments, Inc.); FlexJet (Rosetta Inpharmatic, Inc.); MALDI-TOF mass spectrometer (Sequnome); ChipMaker 2 and Chip-Maker 3 (TeleChem International, Inc.); and GenoSensor (Vysis, Inc.) as identified and described in Heller (2002) Annu Rev. Biomed. Eng. 4:129-153. Examples of "gene chips" or a "microarrays" are also described in U.S. Patent Publ. Nos. 2007-0111322, 2007-0099198, 2007-0084997, 2007-0059769 and 2007-0059765 and U.S. Pat. Nos. 7,138,506, 7,070,740, and 6,989,267.

In one aspect, "gene chips" or "microarrays" containing probes or primers homologous to a polynucleotide, polypeptide or antibody described herein are prepared. A suitable sample is obtained from the patient, extraction of genomic DNA, RNA, protein or any combination thereof is conducted and amplified if necessary. The sample is contacted to the gene chip or microarray panel under conditions suitable for hybridization of the gene(s) or gene product(s) of interest to the probe(s) or primer(s) contained on the gene chip or microarray. The probes or primers may be detectably labeled thereby identifying the gene(s) of interest. Alternatively, a chemical or biological reaction may be used to identify the probes or primers which hybridized with the DNA or RNA of the gene(s) of interest. The genotypes or phenotype of the patient is then determined with the aid of the aforementioned apparatus and methods.

Other non-limiting examples of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. A eukaryotic host, including, for example, yeast, higher plant, insect and mammalian cells, or alternatively from a prokaryotic cells as described above. Non-limiting examples include simian, bovine, porcine, murine, rats, avian, reptilian and human.

"Prokaryotic cells" that usually lack a nucleus or any other membrane-bound organelles and are divided into two domains, bacteria and archaea. Additionally, instead of having chromosomal DNA, these cells' genetic information is in a circular loop called a plasmid. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *bacillus* bacteria, *E. coli* bacterium, and *Salmonella* bacterium.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are described herein.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

As used herein, "isotype" refers to the antibody class (e.g., IgM or IgG1) that is encoded by heavy chain constant region genes.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

The terms "monoclonal antibody" or "monoclonal antibody composition" as used herein refer to a preparation of antibody molecules of single molecular composition. A monoclonal antibody composition displays a single binding specificity and affinity for a particular epitope.

As used herein, the term "label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

II. Antidotes

Factor X and Factor Xa Derivatives

One aspect of the present invention is the use of fX derivatives, such as Gla-domain deficient fX or fXa or des-Gla fX or fXa, as safe and effective antidotes to substantially neutralize the activity of an inhibitor of the coagulation fXa to prevent or stop bleeding. It is contemplated that the antidotes of the present invention will be useful in reversing the anticoagulant effect of a fXa inhibitor, especially an active site-directed small molecule inhibitor.

It is contemplated that an antidote to a fXa inhibitor has reduced or no procoagulant activity but is capable of binding with a fXa inhibitor. It is contemplated that such limited activity permits dosing of the antidote at a level greater than the circulating wild-type fXa. Certain fXa derivatives, such as des-Gla fXa and Gla-deficient fXa, are suitable antidotes of this invention. Besides having reduced or diminished procoagulant activity, antidotes of the present invention should also be substantially non-immunogenic to the subject. An antidote may contain a combination of two or more the above mutations and/or modifications. In addition, any of the above fXa derivatives may be administered alone or in combination with one another.

Factor Xa is a serine protease in the blood coagulation pathway responsible for converting prothrombin to thrombin. It is produced from the inactive factor X upon activation by either the intrinsic Xase (complex formed by factor IXa with its cofactor, factor VIIIa) or the extrinsic Xase (complex formed by factor VIIa with its cofactor, tissue factor). Activated fX (fXa) may undergo further autocatalytic cleavage at the C-terminal of its heavy chain, converting fXaα to the subform fXaβ (Jesty, J et al. *J. Biol. Chem.* 1975, 250(12):4497-4504). Both fXaα and fXaβ are suitable materials for the present invention. fXa itself converts prothrombin at slow rate that is not sufficient for supporting coagulation. Only when it forms a prothrombinase complex with cofactors $Ca^{2+}$, phospholipid, and factor Va, fXa can activate prothrombin at a rate rapid enough to support coagulation (Skogen, W. F., et al., *J. Biol. Chem.* 1984, 259(4):2306-10). The complex requires binding between the negatively charged phospholipid and +γ-carboxyglutamic acid residues in the Gla domain of fXa via $Ca^{2+}$ bridging.

Figure 7:
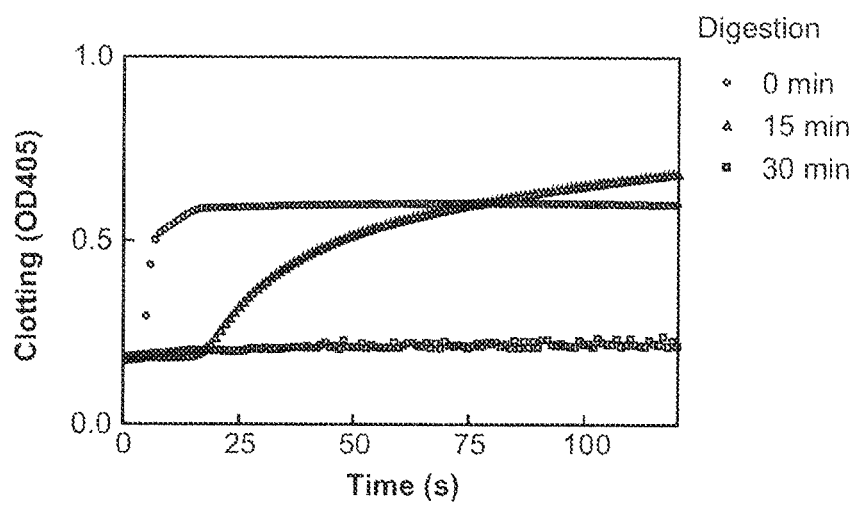
FIG. 7 shows the comparison of the clotting activity of active fXa in a 96-well plate format before chymotrypsin digestion, and after 15 minutes and 30 minutes of chymotrypsin digestion. As shown in this figure, clotting time (change of OD405) was significantly delayed after the fXa had been digested by chymotrypsin for 15 minutes and no clotting was observed for up to 20 minutes when the fXa was digested for 30 minutes. This result was also used to establish conditions for chymotrypsin digestion of anhydro-fXa because it has no activity that can be monitored during digestion. This is more thoroughly described in Example 3.

Therefore, although the Gla domain does not contain the active site of fXa, it enables fXa to form the prothrombinase complex through the γ-carboxyglutamic acid residues. This is demonstrated by selective removal of fXa Gla-domain by chymotrypsin digestion (see FIG. 7 and Example 1). Clotting assays were performed on fXa during the time course of cleavage of the Gla domain by chymotrypsin digestion. It has been reported (Skogen et al *J. Biol. Chem.* 1984, 259(4):2306-10) that a reconstituted prothrombinase complex comprising of Gla-domainless fXa, fVa, phospholipids and calcium ions produces thrombin at a significantly reduced rate (0.5% product generated compared to control complex containing native fXa). As shown in FIG. 7, fXa's activity in clot formation was partially reduced after the fXa was digested by chymotrypsin for 15 minutes and the activity was completely lost after 30 minute of digestion. Undercarboxylated or decarboxylated fXa, which lack the appropriate gamma-carboxyglutamic acid residues required for calcium ion dependent membrane binding, have thus been found to be incapable of membrane dependent coagulation complex assembly and not support blood clotting (Mann, K G et al, *Blood*, 1990, 76: 1-16).

Figure 8:
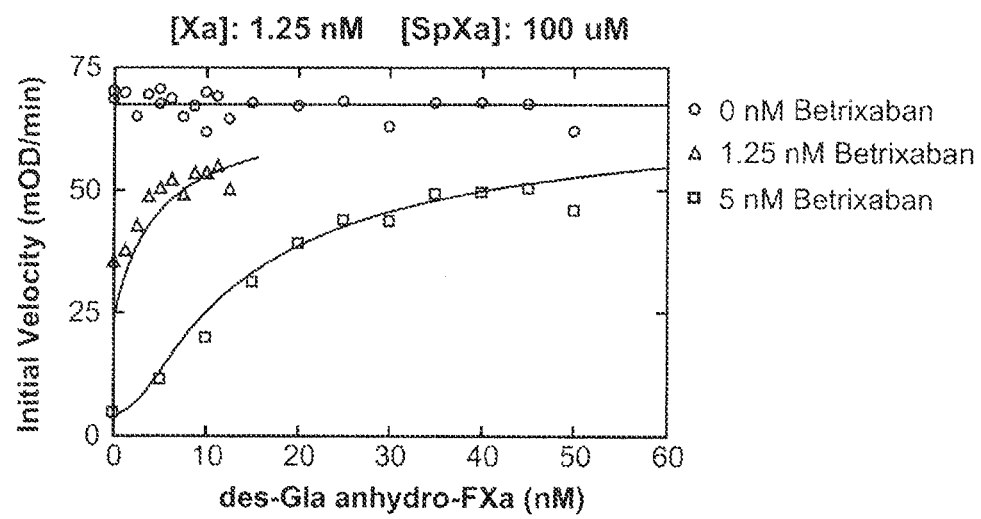
FIG. 8 shows the binding affinity of des-Gla anhydro-fXa to a factor Xa inhibitor betrixaban as described in Example 4. The data show that des-Gla anhydro-fXa, prepared by chymotryptic digestion of anhydro-fXa to remove the Gla-domain containing fragment (residues 1-44), is able to bind betrixaban with similar affinity as native fXa (fXa: Ki=0.12 nM, des-Gla anhydro-fXa: Kd=0.32 nM).

It has also been established that Gla-domain deficient fXa is capable of binding active site-directed inhibitors of fXa. (Brandstetter, H et al, *J. Bio. Chem.*, 1996, 271:29988-29992). There have been reports of crystallography of small molecule fXa inhibitor bound to des-Gla human fXa, which have provided structural description of the active site cleft (Brandstetter, *J. Bio. Chem.*, 1996, 271:29988-29992 and Roehrig, *J. Med. Chem.* 2005, 48(19):5900-8). FIG. 8 shows that a des-Gla anhydro-fXa exhibited a binding affinity of 0.319 nM with a fXa inhibitor betrixaban, comparable to that of a native fXa.

Figure 9:
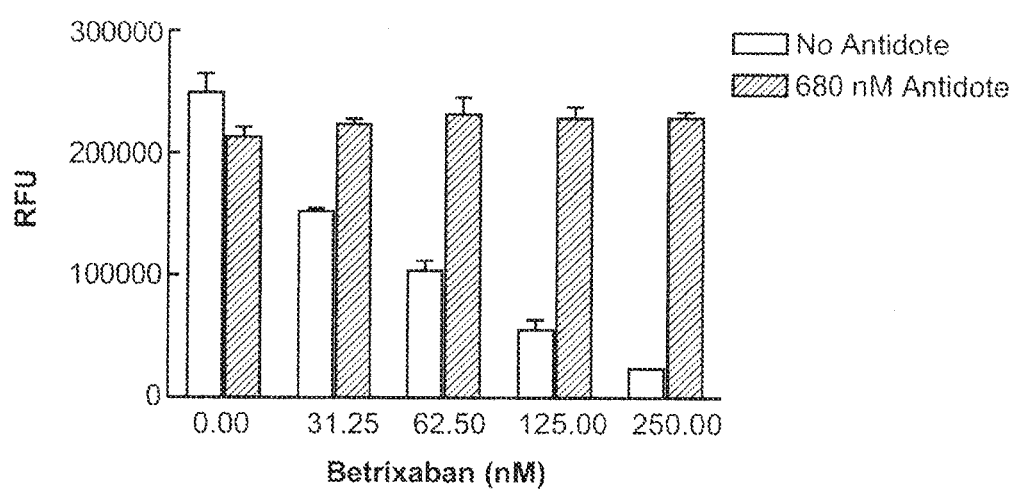
FIG. 9 shows reversal of the anticoagulant activity of varying concentrations of betrixaban by addition of a concentrate of 680 nM of the antidote (des-Gla anhydro-fXa) in a thrombin generation assay of Example 2. At the concentration of 680 nM, des-Gla anhydro-fXa was able to produce substantially complete restoration of fXa activity.

It has now been discovered that des-Gla fXa, and other fX derivatives that have reduced procoagulant activity but are capable of fXa inhibitor binding, can be used as an antidote to a fXa inhibitor. As shown in FIG. 9, the des-Gla anhydro-fXa exhibited complete reversion of betrixaban's anticoagulant activity at a concentration of 680 nM. As detailed in Example 2, the thrombin generation was initiated by adding TF-containing reagent (Innovin) and, thus, indicative of coagulation factors function in the extrinsic coagulation pathway. It has also been demonstrated in Examples 9-13, that the recombinant antidote is useful to reverse a wide variety of anticoagulants.

Figure 10:
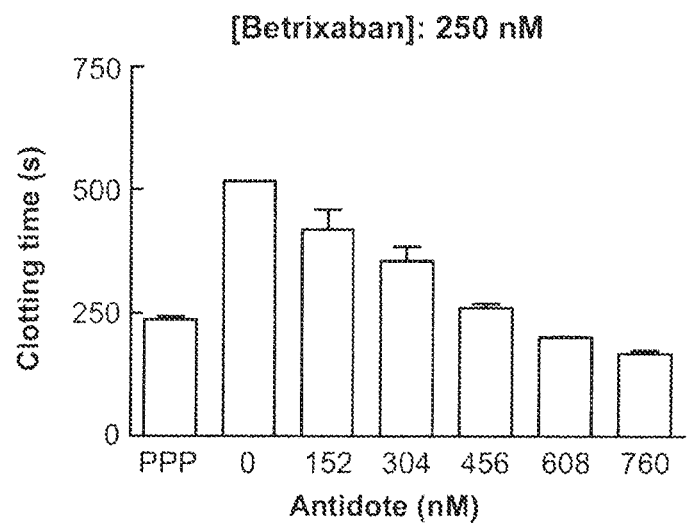
FIG. 10 shows reversal of the anticoagulant activity of 250 nM of betrixaban by varying concentrations of the antidote (des-Gla anhydro-fXa) in clotting prolongation assays using aPTT reagent in a 96-well plate format (as described in Example 3). The data show that clotting time was comparable to that of control platelet poor plasma (PPP) when about 608 nM of the antidote was used to neutralize 250 nM of the fXa inhibitor betrixaban.
Figure 11:
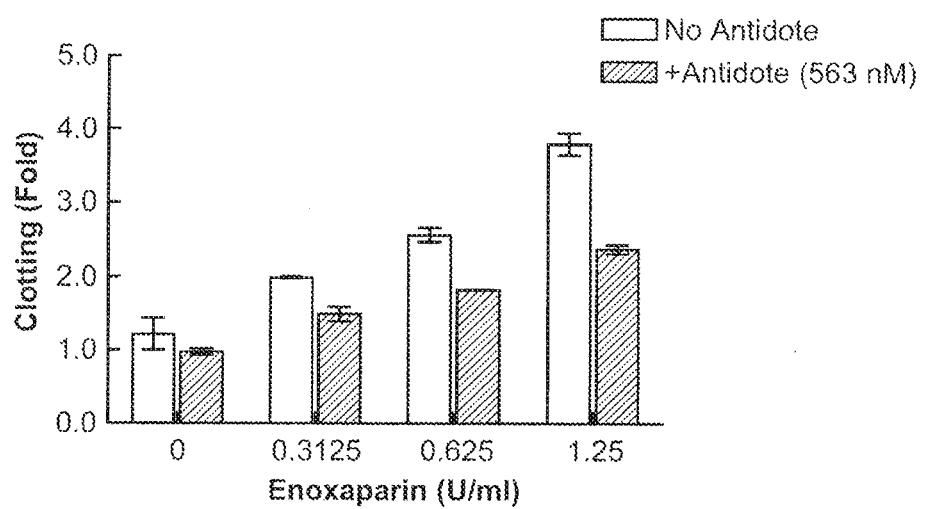
FIG. 11 shows the effect on the anticoagulant activity of enoxaparin (0.3125-1.25 U/mL) by 563 nM of the antidote (des-Gla anhydro-fXa) in clotting prolongation assays using aPTT reagent in a 96-well plate format, expressed as fold changes after normalization. The assay protocol is described in Example 3. The data show that addition of 563 nM of the antidote significantly neutralized the activity of a low molecular weight heparin enoxaparin.
Figure 12:
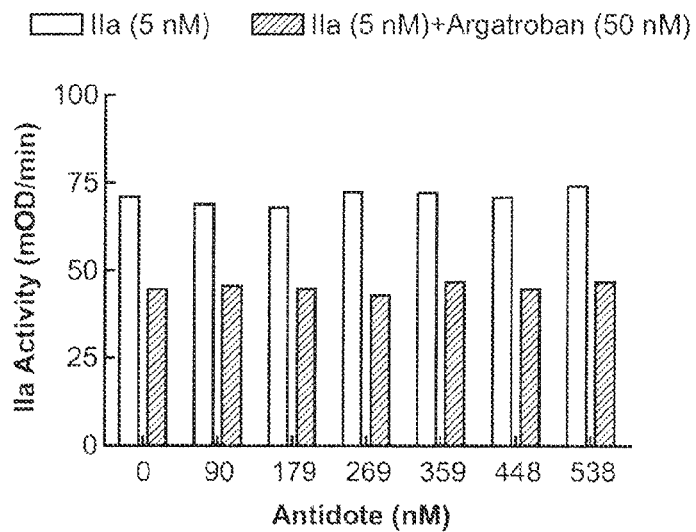
FIG. 12 shows the effect of the antidote, des-Gla anhydro-fXa, on the activity of thrombin (5 nM) and its inhibition by 50 nM of argatroban, a specific thrombin inhibitor, in a chromogenic assay. The antidote of fXa inhibitor does not detectably affect either thrombin activity or its inhibition by the specific inhibitor argatroban at concentrations up to 538 nM. This is more thoroughly described in Example 14.

Clotting prolongation assays with the activated partial thromboplastin time (aPTT) reagent (Actin FS) that determine the function of the coagulation factor in the intrinsic coagulation pathway also indicate that the des-Gla anhydro-fXa possess antidote activity. FIG. 10 shows the dose responsive antidote effect of des-Gla anhydro-fXa against 250 nM of betrixaban, with complete reversion at 600 nM. FIG. 11 shows that des-Gla anhydro-fXa was also capable of reversing the anticoagulant activity of another fXa inhibitor, enoxaparin. FIG. 12 shows that des-Gla anhydro-fXa did not exhibit significant antidote activity against a direct thrombin inhibitor argatroban. Thus, the des-Gla anhydro-fXa is a selective antidote for fXa inhibitors and is capable of restoring fXa procoagulant activity initiated either by the extrinsic or the intrinsic pathway.

Figure 13:
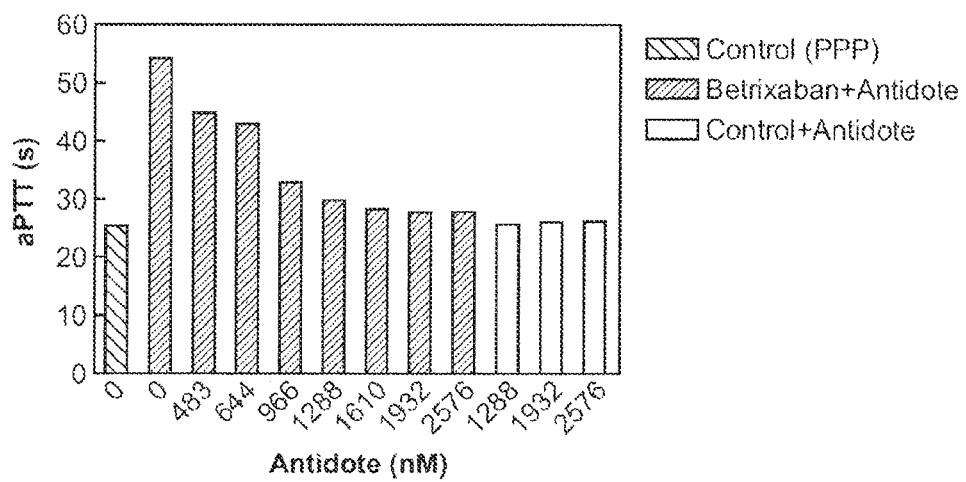
FIG. 13 shows the effect on the anticoagulant activity of 400 nM betrixaban by varying concentrations of the antidote, des-Gla anhydro-fXa, in an aPTT assay using a standard coagulation timer. The assay protocol is described in Example 3. The data shows that the antidote of fXa inhibitor substantially reverses the inhibition of fXa by 400 nM of betrixaban. The $EC_{50}$ of the antidote was estimated to be about 656 nM with 400 nM betrixaban.

Further, the antidote activity of des-Gla anhydro-fXa was demonstrated by the aPTT prolongation assays measured with a traditional coagulation timer. As shown in FIG. 13, des-Gla anhydro-fXa itself has no effect on aPTT of control plasma at the highest concentrations tested (2576 nM). 400 nM of betrixaban extended aPTT more than two folds. This anti-coagulant effect of betrixaban is reversed by des-Gla anhydro-fXa in a dose-responsive manner, with return of aPTT to near normal level of control plasma at antidote concentrations higher than 1610 nM.

It is contemplated that further truncations at the fXa light chain, for example, additional deletion of the EGF1 domain, EGF1 plus EGF2 domains, or fragments thereof, and inactive fXa with only the heavy chain may be useful antidotes of this invention. In one embodiment, the derivative comprises deletion of substantially all of the EGF1 domain, deletion of substantially all of an EGF2 domains, or both. In one embodiment, deletion of substantially all of the EGF1 domain comprises at least about 50% or least about 80% of amino acid residues 46 to 84 of SEQ ID NO. 3 or an equivalent thereof. In another embodiment, deletion of substantially all of the EGF2 domain comprises at least about 50% or at least about 80% of amino acid residues 85-128 of SEQ ID NO. 3.

Gla-domain deficient fXa does not support normal coagulation under physiologically relevant concentration. However, the protein has the ability of cleaving many substrates and causing clotting at higher concentrations. For example, Skogen et al (Skogen, W. F., et al., *J. Biol. Chem.* 1984, 259(4):2306-10) showed that bovine des-Gla fXa has about 0.5-1.0% prothrombinase complex activity relative to the wild type fXa. Thus, modifications that further reduce or completely eliminate a fXa derivative's procoagulant activity is contemplated by methods of the invention. Such modification may be, for example, in a fXa's catalytic domain.

Several ways of modifying the catalytic domain in the fXa heavy chain to reduce its procoagulant activity are contemplated. The active site residue 5379 of fXa (as shown in SEQ ID NO. 7), for example, can be selectively replaced by dehydro-alanine (see Example 1) or alanine (see Example 6) to reduce or eliminate the procoagulant activity. It is also known that complex formation between fXa and a reagent targeting fXa's exosite may block the macromolecular binding ability of fXa, thus reducing its procoagulant activity while retaining small molecule binding ability in the active site. This exosite targeting reagent includes, without limitation, monoclonal antibodies targeting a region removed from the active site (Wilkens, M and Krishnaswamy, S, *J. Bio. Chem.*, 2002, 277 (11), 9366-9374), or α-2-macroglobulin. It has been known that the α-2-macroglobulin-serine protease complex, such as with trypsin, thrombin or fXa, is capable of binding small molecule substrates (Kurolwa, K. et al, *Clin. Chem.* 1989, 35(11), 2169-2172).

Figure 6:
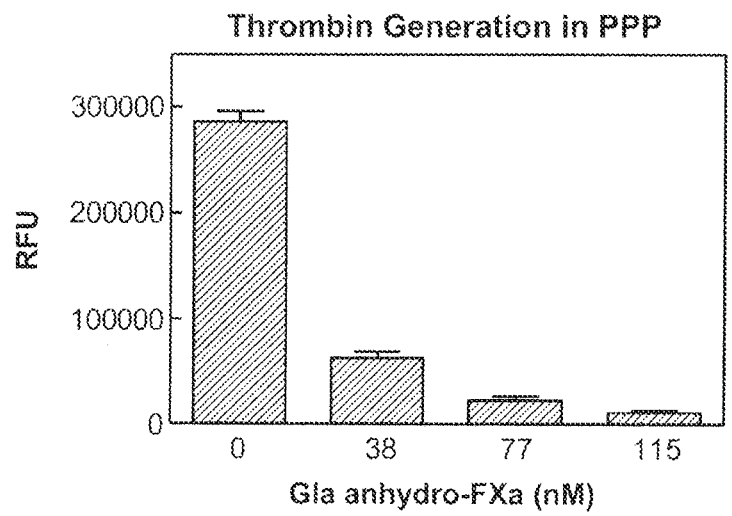
FIG. 6 shows that the anhydro-fXa with intact Gla domain in FIG. 5 is a potent inhibitor in plasma thrombin generation (expressed as relative fluorescence units (RFU)) assay (as described in Example 2). It almost completely inhibited thrombin generation at about 115 nM. The data show that anhydro-fXa without modification of the Gla-domain is not suitable for use as a fXa inhibitor antidote.

It is also known that an inactive fXa with modifications solely in the heavy chain while keeping its light chain unchanged would act as an inhibitor of prothrombinase (Hollenbach, S. et al., Thromb. Haemost., 1994, 71(3), 357-62) because it interferes with procoagulant activity of normal fXa as shown in FIG. 6. Therefore, in one embodiment, the fXa derivative has modifications both in the light chain and heavy chain. It has been discovered that these modifications reduce or eliminate both procoagulant and anticoagulant activities while retaining the inhibitors binding ability of the fXa derivative.

Several methods can be used to produce Gla-domain deficient fXa derivatives or other fXa derivatives described herein. For example, the Gla-domain may be completely removed via chymotryptic cleavage, producing Gla-domainless fXa. Alternatively, a Gla-domainless fX may be produced by chymotryptic cleavage of native fX. The Gla-domainless fX may then be converted to Gla-domainless fXa by a fX activator. fX may be isolated from plasma of the same or a different species as the subject to be treated. Bovine fX, for example, has been shown to be functional in human plasma assays. Examples of a fX activator include, without limitation, a snake venom, such as Russell's viper venom, and complexes of fVIIa/tissue factor or fIXa/fVIIIa. Such means is known to a person of skill in the art. For example, Rudolph A. E. et al has reported a recombinant fXa produced from a recombinant factor X (fX) with a single substitution of Arg347 by Glutamine (fXR347N) (*Biochem.* 2000, 39 (11): 2861-2867). In one embodiment, the fXa derivatives produced from non-human sources are non-immunogenic or substantially non-immunogenic. Example 7 also provides a method of producing a recombinant antidote having the amino acid sequence of SEQ ID NO. 12.

The fXa derivatives may also be purified from human plasma, or may be produced by recombinant DNA method where an appropriate gene for the fXa derivative is expressed in a suitable host organism. Expression and purification of recombinant fXa has been reported by several groups, see, e.g., Larson, P. J., et al, *Biochem.*, 1998, 37:5029-5038, and Camire, R. M., et al, *Biochem.*, 2000, 39, 14322-14329 for producing recombinant fX; Wolf, D. L. et al, *J. Bio. Chem.*, 1991, 266(21):13726-13730 for producing recombinant fXa. Modified fXa may be prepared according to these procedures using a genetically modified cDNA having a nucleotide sequence encoding the desired fXa mutant. Example 6 gives more details for direct expression of a Gla-domainless fXa-5379 mutant with functional activity as an antidote.

It is contemplated that active-site mutated or modified fXa with deficient Gla-domain, such as under-carboxylated fXa, may also be useful as fXa inhibitor antidote. Under-carboxylated fXa may be prepared by recombinant means by withholding vitamin K derivatives during protein expression (vitamin K derivatives are needed for post translational modification to form the Gla residues) or by adding vitamin K antagonists such as warfarin during tissue culture. Decarboxylated fXa can be prepared by heating (Bajaj P., *J. Biol. Chem.*, 1982, 257(7):3726-3731) or by proteolytic digestion by chymotrypsin (Morita T., et al., *J. Biol. Chem.*, 1986, 261(9):4015-4023). The antidote may also be generated in prokaryotic systems followed by in vitro refolding or constitution of the fXa inhibitor binding site.

The Gla residues can also be chemically modified to remove the carboxyl group responsible for calcium ion dependent membrane binding. For example, the carboxyl groups on the Gla residues may be selectively removed under decarboxylation conditions or may be capped, for example, by esterification or amination. It is desirable that such esterification or amination be resistant to in vivo hydrolysis so that the modified fXa is not readily converted to active fXa, which may cause thrombosis.

Other mutants or derivatives of fXa may also be useful antidotes of this invention. In one embodiment, this invention encompasses use of mutants described in Peter J. Larson et al, *Biochem.*, 1998, 37:5029-5038 as fXa inhibitor antidotes.

Additional modifications of the fX protein may be made to produce useful antidotes to fXa inhibitors. One such modification includes deleting all or part of the activation peptide at the N-terminus of the heavy chain. In one embodiment, this includes deletion of all of part of the activation peptide or amino acid residues 143-194 of SEQ ID NO. 3 or an equivalent thereof. This may be accomplished by procedures described in Sinha et al. *Protein Expression and Purification*, 3, 518-524 (1992) and Wolf et al. *J. Biol. Chem.* 266(21), 13726-13730 (1991), which are both incorporated herein by reference. Additional methods are described below.

In another embodiment, an amino acid modification prevents cleavage of a β-peptide wherein β-peptide refers to a portion of or the entire heavy chain. This modification can include deletion, substitution, or insertion of an amino acid. On such modification includes substitutions of one or more of Arg429 or Ser436. For example, there is a Arg 429Gln substitution and may also include a Thr443Ala substitution. Conversion of fXaα to fXaβ has been described by, for example, Pryzdial and Kessler (Pryzdial L G and Kessler G E, *Journal of Biological Chemistry*, 271(28), 16621-16626 (1996). U.S. Pat. No. 7,220,569(B2) described modifications in the fX activation peptide and β-peptide. This reference is incorporated by reference in its entirety.

In still another embodiment, the derivative comprises a deletion of a β-peptide. In one embodiment, the deletion of the β-peptide comprises a deletion of at least amino acid residues 430-448 of SEQ ID NO. 3 or an equivalent thereof.

In another embodiment, a native factor X signal peptide sequence or an alternative signal peptide sequence is used to express the derivatives. For example, the native factor X signal peptide (SEQ ID NO. 18) can be used as the signal sequence for SEQ ID NO. 12-15 and 19-25. The signal peptide may be selected from a factor X signal peptide (SEQ ID NO. 18), a transferrin signal peptide (amino acid residues SP1-SP19 of SEQ ID NO. 27) and a prothrombin signal peptide (amino acid residues SP1-SP24 of SEQ ID NO. 26). It is contemplated that the factor X signal peptide may be used in as the signal peptide of any of the sequences described herein. Use of prothrombin signal peptide in replacing native fX signal peptide has been described by Guarna et al (Guarna M M et al, *Protein Expression and Purification*, 20(2) 133-41(2000)) and Camire et al (Camire R M, et al, *Biochemistry*, 39, 14322-14329(2000)). Use of transferring signal peptide has been described by Rezaie and Esmon (Rezaie A R and Charles T. Esmon C T, *J. Biol. Chem.*, 267(36), 26104-26109(1992)). Both references are incorporated by reference in their entirety.

In yet another embodiment of the invention, the polypeptide has a precursor peptide which is a one chain polypeptide. In one embodiment, there is a RKR (SEQ ID NO. 40) linker at a C-terminus of a light chain or a RKRRKR (SEQ ID NO. 41) linker at the C-terminus of a light chain. In another embodiment, the derivative is a two-chain polypeptide. Expression of fXa mutant suitable as antidote or antidote precursor of the invention with RKRRKR linker (SEQ ID NO: 41) has been fully described in US patent publication 2009/0098119A1. Use of RKR (SEQ ID NO. 40) linker to connect fXa light chain and activation peptiden has been 49 discussed in U.S. Pat. No. 5,990,079. Both the patent and the patent application just listed are incorporated by reference in their entirety.

In another embodiment, this invention encompasses use of catalytically inactive fXa mutants to prepare fXa inhibitor antidotes. For example, mutants described in Sinha, U., et al, *Protein Expression and Purif.*, 1992, 3:518-524 rXai, mutants with chemical modifications, such as dehydroalanine (anhydro fXa), as described in Nogami, et al, *J. Biol. Chem.* 1999, 274(43):31000-7. FXa with active site serine (Ser379 in fX numbering as shown in SEQ ID NO. 7, and Ser195 in chymotrypsin numbering) replaced with alanine (fXa-S379A in fX numbering, or fXa-S195A in chymotrypsin numbering), where the procoagulant activity was eliminated, may also be used as fXa inhibitor antidotes. The invention also envisions fXa derivatives with the active site serine residue irreversibly acylated which is still capable of binding small molecule inhibitors. FXa with the active site serine reversibly acylated has been reported by Wolf, et al., *Blood*, 1995, 86(11):4153-7. Such reversible acylation, however, is capable of time dependent production of active fXa and may lead to an excess of active fXa over a time period. The deacylation rate may be reduced by strategies similar to those described in Lin P. H. et al, *Thrombosis Res.*, 1997, 88(4), 365-372. For example, fXa molecules with Ser379 (Ser195 in chymotrypsin numbering) acylated by 4-methoxybenzyl and 3-bromo-4-methoxybenzyl groups recover less than 50% of their original activity when incubated in a buffer having pH 7.5 at 37° C. for 4 hours.

One embodiment is directed to the use of fXa derivatives with mutations at fXa residues known to be important for fXa interaction with cofactor fV/fVa. Such residues include, without limitation, Arg306, Glu310, Arg347, Lys351, or Lys414 (SEQ ID NOS. 3 and 7, these amino acids correspond to Arg125, Glu129, Arg165, Lys169, Lys230 in the chymotrypsin numbering). Examples of such mutants are reported in Rudolph, A. E. et al, *J. Bio. Chem.*, 2001, 276:5123-5128. In addition, mutations at fXa residues known to be important for fVIII/fVIIIa interaction, such as Arg424 in SEQ ID NOS. 3 and 7 (Arg240 in chymotrypsin numbering), may also be used as fXa inhibitor antidotes. Examples of such mutants are described in Nogami, K. et al, *J. Biol. Chem.*, 2004, 279(32):33104-33113.

Other modification of active site residues of fXa or residues known to be important for serine protease interactions may also lead to useful antidotes of this invention, for example, replacement of Glu216, Glu218, and Arg332 in SEQ ID NOS. 3 and 7 (Glu37, Glu39, and Arg150 in chymotrypsin numbering, respectively) with other amino acid residues.

One embodiment is directed to mutations at the autolysis loop of FXa heavy chain to eliminate potential degradation. FXa, like other serine proteases of the family, has an exposed surface loop (autolysis loop) which is susceptible to cleavage by various proteases. This loop, including amino acids RTHEKGRQSTR (SEQ ID NO. 39), which are amino acids 366 to 376 of SEQ ID NO. 1, contains several positively charged residues (Arg366, Lys370, Arg372, Arg376) with Arg372 as the potential recognition site for cleavage (Brandstetter H., et. Al., J. Biol. Chem., 271(1996), 29988-29992). It is completed that these charged residues are mutated to Gln (Q) or Ala (A) to prohibit the possible cleavage. In one aspect, the mutation is Arg366Q/A. In another aspect, the mutation is Lys370Q/A. In yet another aspect, the mutation is Arg372Q/A. In yet another aspect, the mutation is Arg376Q/A. In some embodiments, a fXa derivative has one or more such mutations.

One embodiment of the invention is directed to an isolated polypeptide of SEQ ID NOs. 12, 13, 15, 19-25, or an isolated polypeptide having at least 80% homology to SEQ ID NOs. 12, 13, 15, 19-25, further comprising one or more mutations selected from the group consisting of Arg366Q/A, Lys370Q/A, Arg372Q/A, Arg376Q/A, and combinations thereof. The polypeptides encompassed by the invention include both the single chain polypeptide (i.e., before the polypeptide is excreted from the cell) as well as the two-chain polypeptide (i.e., after cleavage at the linker after it is secreted from the cell).

In one embodiment, the residual procoagulant activity of an antidote, as assessed by amidolytic substrate cleavage assay, be <1%, preferably <0.1%, more preferably <0.05% of human plasma derived native fXa. For example, there is no measurable procoagulant activity for recombinant fXa-S379A when the active site Ser379 (S195 in chymotrypsin numbering) is replaced by an alanine residue as measured by clotting assays.

The invention further relates to nucleic acid sequences, in particular DNA sequences, which code for the fXa derivatives described above. These can easily be determined by translating the polypeptide sequence back into the corresponding DNA sequence in accordance with the genetic code. Codons preferably used are those which lead to good expression in the required host organism. The nucleic acid sequences can be prepared either by site-specific mutagenesis starting from the natural fXa gene sequence or else by complete DNA synthesis.

Polypeptides of the Invention

In certain aspects, the invention is related to an isolated polypeptide comprising the amino acid sequence of SEQ ID NO. 12, 13, 15, or 19-25. Also encompassed by this invention are polypeptides having at least 80% homology to SEQ ID NO. 12, 13, 15, or 19-25.

Polypeptides comprising the amino acid sequences of the invention can be prepared by expressing polynucleotides encoding the polypeptide sequences of this invention in an appropriate host cell. This can be accomplished by methods of recombinant DNA technology known to those skilled in the art. Accordingly, this invention also provides methods for recombinantly producing the polypeptides of this invention in a eukaryotic or prokaryotic host cells. The proteins and polypeptides of this invention also can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

It is known to those skilled in the art that modifications can be made to any peptide to provide it with altered properties. Polypeptides of the invention can be modified to include unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices, β turns, β sheets, α-turns, and cyclic peptides can be generated. Generally, it is believed that α-helical secondary structure or random secondary structure is preferred.

In a further embodiment, subunits of polypeptides that confer useful chemical and structural properties will be chosen. For example, peptides comprising D-amino acids may be resistant to L-amino acid-specific proteases in vivo. Modified compounds with D-amino acids may be synthesized with the amino acids aligned in reverse order to produce the peptides of the invention as retro-inverse peptides. In addition, the present invention envisions preparing peptides that have better defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2NH$—$R_2$, where $R_1$, and $R_2$ are amino acid residues or sequences. A reduced peptide bond may be introduced as a dipeptide subunit. Such a molecule would be resistant to peptide bond hydrolysis, e.g., protease activity. Such molecules would provide ligands with unique function and activity, such as extended half-lives in vivo due to resistance to metabolic breakdown, or protease activity. Furthermore, it is well known that in certain systems constrained peptides show enhanced functional activity (Hruby (1982) Life Sciences 31:189-199 and Hruby et al. (1990) Biochem J. 268:249-262); the present invention provides a method to produce a constrained peptide that incorporates random sequences at all other positions.

The following non-classical amino acids may be incorporated in the peptides of the invention in order to introduce particular conformational motifs: 1,2,3,4-tetrahydroisoquinoline-3-carboxylate (Kazmierski et al. (1991) J. Am. Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby (1991) Tetrahedron Lett. 32(41):5769-5772); 2-aminotetrahydronaphthalene-2-carboxylic acid (Landis (1989) Ph.D. Thesis, University of Arizona); hydroxy-1,2,3,4-tetrahydroisoquinoline-3-carboxylate (Miyake et al. (1989) J. Takeda Res. Labs. 43:53-76) histidine isoquinoline carboxylic acid (Zechel et al. (1991) Int. J. Pep. Protein Res. 38(2):131-138); and HIC (histidine cyclic urea), (Dharanipragada et al. (1993) Int. J. Pep. Protein Res. 42(1):68-77) and (Dharanipragada et al. (1992) Acta. Crystallogr. C. 48:1239-1241).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al. (1985) J. Org. Chem. 50:5834-5838); β-sheet inducing analogs (Kemp et al. (1988) Tetrahedron Lett. 29:5081-5082); β-turn inducing analogs (Kemp et al. (1988) Tetrahedron Lett. 29:5057-5060); α-helix inducing analogs (Kemp et al. (1988) Tetrahedron Lett. 29:4935-4938); α-turn inducing analogs (Kemp et al. (1989) J. Org. Chem. 54:109:115); analogs provided by the following references: Nagai and Sato (1985) Tetrahedron Lett. 26:647-650; and DiMaio et al. (1989) J. Chem. Soc. Perkin Trans. p. 1687; a Gly-Ala turn analog (Kahn et al. (1989) Tetrahedron Lett. 30:2317); amide bond isostere (Clones et al. (1988) Tetrahedron Lett. 29:3853-3856); tetrazole (Zabrocki et al. (1988) J. Am. Chem. Soc. 110:5875-5880); DTC (Samanen et al. (1990) Int. J. Protein Pep. Res. 35:501:509); and analogs taught in Olson et al. (1990) J. Am. Chem. Sci. 112:323-333 and Garvey et al. (1990) J. Org. Chem. 56:436. Conformationally restricted mimetics of beta turns and beta bulges, and peptides containing them, are described in U.S. Pat. No. 5,440,013, issued Aug. 8, 1995 to Kahn.

It is known to those skilled in the art that modifications can be made to any peptide by substituting one or more amino acids with one or more functionally equivalent amino acids that does not alter the biological function of the peptide. In one aspect, the amino acid that is substituted by an amino acid that possesses similar intrinsic properties including, but not limited to, hydrophobicity, size, or charge. Methods used to determine the appropriate amino acid to be substituted and for which amino acid are known to one of skill in the art. Non-limiting examples include empirical substitution models as described by Dayhoff et al. (1978) In Atlas of Protein Sequence and Structure Vol. 5 suppl. 2 (ed. M. O. Dayhoff), pp. 345-352. National Biomedical Research Foundation, Washington D.C.; PAM matrices including Dayhoff matrices (Dayhoff et al. (1978), supra, or JTT matrices as described by Jones et al. (1992) Comput. Appl. Biosci. 8:275-282 and Gonnet et al. (1992) Science 256: 1443-1145; the empirical model described by Adach and Hasegawa (1996) J. Mol. Evol. 42:459-468; the block substitution matrices (BLOSUM) as described by Henikoff and Henikoff (1992) Proc. Natl. Acad. Sci. USA 89:10915-10919; Poisson models as described by Nei (1987) Molecular Evolutionary Genetics. Columbia University Press, New York; and the Maximum Likelihood (ML) Method as described by Müller et al. (2002) Mol. Biol. Evol. 19:8-13.

Polypeptide Conjugates

The polypeptides and polypeptide complexes of the invention can be used in a variety of formulations, which may vary depending on the intended use. For example, one or more can be covalently or non-covalently linked (complexed) to various other molecules, the nature of which may vary depending on the particular purpose. For example, a peptide of the invention can be covalently or non-covalently complexed to a macromolecular carrier, including, but not limited to, natural and synthetic polymers, proteins, polysaccharides, polypeptides (amino acids), polyvinyl alcohol, polyvinyl pyrrolidone, and lipids. A peptide can be conjugated to a fatty acid, for introduction into a liposome, see U.S. Pat. No. 5,837,249. A peptide of the invention can be complexed covalently or non-covalently with a solid support, a variety of which are known in the art and described herein. An antigenic peptide epitope of the invention can be associated with an antigen-presenting matrix such as an MHC complex with or without co-stimulatory molecules.

Examples of protein carriers include, but are not limited to, superantigens, serum albumin, tetanus toxoid, ovalbumin, thyroglobulin, myoglobulin, and immunoglobulin.

Peptide-protein carrier polymers may be formed using conventional cross-linking agents such as carbodiimides. Examples of carbodimides are 1-cyclohexyl-3-(2-morpholinyl-(4-ethyl) carbodiimide (CMC), 1-ethyl-3-(3-dimethyaminopropyl) carbodiimide (EDC) and 1-ethyl-3-(4-azonia-44-dimethylpentyl) carbodiimide.

Examples of other suitable cross-linking agents are cyanogen bromide, glutaraldehyde and succinic anhydride. In general, any of a number of homo-bifunctional agents including a homo-bifunctional aldehyde, a homo-bifunctional epoxide, a homo-bifunctional imido-ester, a homo-bifunctional N-hydroxysuccinimide ester, a homo-bifunctional maleimide, a homo-bifunctional alkyl halide, a homo-bifunctional pyridyl disulfide, a homo-bifunctional aryl halide, a homo-bifunctional hydrazide, a homo-bifunctional diazonium derivative and a homo-bifunctional photoreactive compound may be used. Also included are hetero-bifunctional compounds, for example, compounds having an amine-reactive and a sulfhydryl-reactive group, compounds with an amine-reactive and a photoreactive group and compounds with a carbonyl-reactive and a sulfhydryl-reactive group.

Specific examples of such homo-bifunctional cross-linking agents include the bifunctional N-hydroxysuccinimide esters dithiobis(succinimidylpropionate), disuccinimidyl suberate, and disuccinimidyl tartrate; the bifunctional imido-esters dimethyl adipimidate, dimethyl pimelimidate, and dimethyl suberimidate; the bifunctional sulfhydryl-reactive crosslinkers 1,4-di-[3'-(2'-pyridyldithio) propionamido]butane, bismaleimidohexane, and bis-N-maleimido-1, 8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), N1N'-hexamethylene-bis(iodoacetamide), N1N'-undecamethylene-bis(iodoacetamide), as well as benzylhalides and halomustards, such as a1a'-diiodo-p-xylene sulfonic acid and tri(2-chloroethyl)amine, respectively.

Examples of common hetero-bifunctional cross-linking agents that may be used to effect the conjugation of proteins to peptides include, but are not limited to, SMCC (succinimidyl-4-(N-maleimidomethyl)cyclohexane-1-carboxylate), MBS (m-maleimidobenzoyl-N-hydroxysuccinimide ester), SIAB (N-succinimidyl(4-iodoacteyl)aminobenzoate), SMPB (succinimidyl-4-(p-maleimidophenyl)butyrate), GMBS (N-(γ-maleimidobutyryloxy)succinimide ester), MPBH (4-(4-N-maleimidopohenyl) butyric acid hydrazide), M2C2H (4-(N-maleimidomethyl) cyclohexane-1-carboxyl-hydrazide), SMPT (succinimidyloxycarbonyl-α-methyl-α-(2-pyridyldithio)toluene), and SPDP (N-succinimidyl 3-(2-pyridyldithio)propionate).

Cross-linking may be accomplished by coupling a carbonyl group to an amine group or to a hydrazide group by reductive amination.

Peptides of the invention also may be formulated as non-covalent attachment of monomers through ionic, adsorptive, or biospecific interactions. Complexes of peptides with highly positively or negatively charged molecules may be done through salt bridge formation under low ionic strength environments, such as in deionized water. Large complexes can be created using charged polymers such as poly-(L-glutamic acid) or poly-(L-lysine) which contain numerous negative and positive charges, respectively. Adsorption of peptides may be done to surfaces such as microparticle latex beads or to other hydrophobic polymers, forming non-covalently associated peptide-superantigen complexes effectively mimicking cross-linked or chemically polymerized protein. Finally, peptides may be non-covalently linked through the use of biospecific interactions between other molecules. For instance, utilization of the strong affinity of biotin for proteins such as avidin or streptavidin or their derivatives could be used to form peptide complexes. These biotin-binding proteins contain four binding sites that can interact with biotin in solution or be covalently attached to another molecule. (See Wilchek (1988) Anal. Biochem. 171:1-32). Peptides can be modified to possess biotin groups using common biotinylation reagents such as the N-hydroxysuccinimidyl ester of D-biotin (NHS-biotin) which reacts with available amine groups on the protein. Biotinylated peptides then can be incubated with avidin or streptavidin to create large complexes. The molecular mass of such polymers can be regulated through careful control of the molar ratio of biotinylated peptide to avidin or streptavidin.

Also provided by this application are the peptides and polypeptides described herein conjugated to a label, e.g., a fluorescent or bioluminescent label, for use in the diagnostic methods. For example, detectably labeled peptides and polypeptides can be bound to a column and used for the detection and purification of antibodies. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in Haugland, Richard P. (1996) Molecular Probes Handbook.

The polypeptides of this invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils. When used to prepare antibodies, the carriers also can include an adjuvant that is useful to non-specifically augment a specific immune response. A skilled artisan can easily determine whether an adjuvant is required and select one. However, for the purpose of illustration only, suitable adjuvants include, but are not limited to, Freund's Complete Adjuvant, Freund's Incomplete Adjuvant and mineral salts.

Host Cells

Also provided are host cells comprising one or more of the polypeptides of this invention. In one aspect, the polypeptides are expressed and present on the cell surface (extracellularly). Suitable cells containing the inventive polypeptides include prokaryotic and eukaryotic cells, which include, but are not limited to bacterial cells, yeast cells, insect cells, animal cells, mammalian cells, murine cells, rat cells, sheep cells, simian cells and human cells. Examples of bacterial cells include *Escherichia coli, Salmonella enterica* and *Streptococcus gordonii*. The cells can be purchased from a commercial vendor such as the American Type Culture Collection (ATCC, Rockville Md., USA) or cultured from an isolate using methods known in the art. Examples of suitable eukaryotic cells include, but are not limited to 293T HEK cells, as well as the hamster cell line CHO, BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of insect cells include *Spodoptera frugiperda*. Examples of yeast useful for expression include, but are not limited to *Saccharomyces, Schizosaccharomyces, Hansenula, Candida, Torulopsis, Yarrowia,* or *Pichia*. See e.g., U.S. Pat. Nos. 4,812,405; 4,818,700; 4,929,555; 5,736,383; 5,955, 349; 5,888,768 and 6,258,559.

In addition to species specificity, the cells can be of any particular tissue type such as neuronal or alternatively a somatic or embryonic stem cell such as a stem cell that can or cannot differentiate into a neuronal cell, e.g., embryonic stem cell, adipose stem cell, neuronal stem cell and hematopoietic stem cell. The stem cell can be of human or animal origin, such as mammalian.

Isolated Polynucleotides and Compositions

This invention also provides the complementary polynucleotides to the sequences identified above or their complements. Complementarity can be determined using traditional hybridization under conditions of moderate or high stringency. As used herein, the term polynucleotide intends DNA and RNA as well as modified nucleotides. For example, this invention also provides the anti-sense polynucleotide stand, e.g. antisense RNA to these sequences or their complements.

Also provided are polynucleotides encoding substantially homologous and biologically equivalent polypeptides to the inventive polypeptides and polypeptide complexes. Substantially homologous and biologically equivalent intends those having varying degrees of homology, such as at least 65%, or alternatively, at least 70%, or alternatively, at least 75%, or alternatively at least 80%, or alternatively, at least 85%, or alternatively at least 90%, or alternatively, at least 95%, or alternatively at least 97% homologous as defined above and which encode polypeptides having the biological activity to bind factor Xa inhibitors and do not assemble into the prothrombinase complex as described herein. It should be understood although not always explicitly stated that embodiments to substantially homologous polypeptides and polynucleotides are intended for each aspect of this invention, e.g., polypeptides, polynucleotides and antibodies.

The polynucleotides of this invention can be replicated using conventional recombinant techniques. Alternatively, the polynucleotides can be replicated using PCR technology. PCR is the subject matter of U.S. Pat. Nos. 4,683,195; 4,800,159; 4,754,065; and 4,683,202 and described in PCR: The Polymerase Chain Reaction (Mullis et al. eds, Birkhauser Press, Boston (1994)) and references cited therein. Yet further, one of skill in the art can use the sequences provided herein and a commercial DNA synthesizer to replicate the DNA. Accordingly, this invention also provides a process for obtaining the polynucleotides of this invention by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can operatively link the polynucleotides to regulatory sequences for their expression in a host cell. The polynucleotides and regulatory sequences are inserted into the host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

RNA can be obtained by first inserting a DNA polynucleotide into a suitable prokaryotic or eukaryotic host cell. The DNA can be inserted by any appropriate method, e.g., by the use of an appropriate gene delivery vehicle (e.g., liposome, plasmid or vector) or by electroporation. When the cell replicates and the DNA is transcribed into RNA; the RNA can then be isolated using methods well known to those of skill in the art, for example, as set forth in Sambrook and Russell (2001) supra. For instance, mRNA can be isolated using various lytic enzymes or chemical solutions according to the procedures set forth in Sambrook and Russell (2001) supra or extracted by nucleic-acid-binding resins following the accompanying instructions provided by manufactures.

In one aspect, the RNA is short interfering RNA, also known as siRNA. Methods to prepare and screen interfering RNA and select for the ability to block polynucleotide expression are known in the art and non-limiting examples of which are shown below. These interfering RNA are provided by this invention.

siRNA sequences can be designed by obtaining the target mRNA sequence and determining an appropriate siRNA complementary sequence. siRNAs of the invention are designed to interact with a target sequence, meaning they complement a target sequence sufficiently to hybridize to that sequence. An siRNA can be 100% identical to the target sequence. However, homology of the siRNA sequence to the target sequence can be less than 100% as long as the siRNA can hybridize to the target sequence. Thus, for example, the siRNA molecule can be at least 70%, 75%, 80%, 85%, 90%, 95%, 96%, 97%, 98%, 99% or 100% identical to the target sequence or the complement of the target sequence. Therefore, siRNA molecules with insertions, deletions or single point mutations relative to a target may also be used. The generation of several different siRNA sequences per target mRNA is recommended to allow screening for the optimal target sequence. A homology search, such as a BLAST search, should be performed to ensure that the siRNA sequence does not contain homology to any known mammalian gene.

In general, it is preferable that the target sequence be located at least 100-200 nucleotides from the AUG initiation codon and at least 50-100 nucleotides away from the termination codon of the target mRNA (Duxbury (2004) J. Surgical Res. 117:339-344).

Researchers have determined that certain characteristics are common in siRNA molecules that effectively silence their target gene (Duxbury (2004) J. Surgical Res. 117:339-344; Ui-Tei et al. (2004) Nucl. Acids Res. 32:936-48). As a general guide, siRNAs that include one or more of the following conditions are particularly useful in gene silencing in mammalian cells: GC ratio of between 45-55%, no runs of more than 9 G/C residues, G/C at the 5' end of the sense strand; A/U at the 5' end of the antisense strand; and at least 5 A/U residues in the first 7 bases of the 5' terminal of the antisense strand.

siRNA are, in general, from about 10 to about 30 nucleotides in length. For example, the siRNA can be 10-30 nucleotides long, 12-28 nucleotides long, 15-25 nucleotides long, 19-23 nucleotides long, or 21-23 nucleotides long. When an siRNA contains two strands of different lengths, the longer of the strands designates the length of the siRNA. In this situation, the unpaired nucleotides of the longer strand would form an overhang.

The term siRNA includes short hairpin RNAs (shRNAs). shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides long. For example, the stem can be 10-30 nucleotides long, 12-28 nucleotides long, 15-25 nucleotides long, 19-23 nucleotides long, or 21-23 nucleotides long.

Tools to assist siRNA design are readily available to the public. For example, a computer-based siRNA design tool is available on the internet.

Synthesis of dsRNA and siRNA dsRNA and siRNA can be synthesized chemically or enzymatically in vitro as described in Micura (2002) Agnes Chem. Int. Ed. Emgl. 41:2265-2269; Betz (2003) Promega Notes 85:15-18; and Paddison and Hannon (2002) Cancer Cell. 2:17-23. Chemical synthesis can be performed via manual or automated methods, both of which are well known in the art as described in Micura (2002), supra. siRNA can also be endogenously expressed inside the cells in the form of shRNAs as described in Yu et al. (2002) Proc. Natl. Acad. Sci. USA 99:6047-6052; and McManus et al. (2002) RNA 8:842-850. Endogenous expression has been achieved using plasmid-based expression systems using small nuclear RNA promoters, such as RNA polymerase III U6 or H1, or RNA polymerase II U1 as described in Brummelkamp et al. (2002) Science 296:550-553 (2002); and Novarino et al. (2004) J. Neurosci. 24:5322-5330.

In vitro enzymatic dsRNA and siRNA synthesis can be performed using an RNA polymerase mediated process to produce individual sense and antisense strands that are annealed in vitro prior to delivery into the cells of choice as describe in Fire et al. (1998) Nature 391:806-811; Donze and Picard (2002) Nucl. Acids Res. 30(10):e46; Yu et al. (2002); and Shim et al. (2002) J. Biol. Chem. 277:30413-30416. Several manufacturers (Promega, Ambion, New England Biolabs, and Stragene) produce transcription kits useful in performing the in vitro synthesis.

In vitro synthesis of siRNA can be achieved, for example, by using a pair of short, duplex oligonucleotides that contain T7 RNA polymerase promoters upstream of the sense and antisense RNA sequences as the DNA template. Each oligonucleotide of the duplex is a separate template for the synthesis of one strand of the siRNA. The separate short RNA strands that are synthesized are then annealed to form siRNA as described in Protocols and Applications, Chapter 2: RNA interference, Promega Corporation, (2005).

In vitro synthesis of dsRNA can be achieved, for example, by using a T7 RNA polymerase promoter at the 5'-ends of both DNA target sequence strands. This is accomplished by using separate DNA templates, each containing the target sequence in a different orientation relative to the T7 promoter, transcribed in two separate reactions. The resulting transcripts are mixed and annealed post-transcriptionally. DNA templates used in this reaction can be created by PCR or by using two linearized plasmid templates, each containing the T7 polymerase promoter at a different end of the target sequence. Protocols and Applications, Chapter 2: RNA interference, Promega Corporation, (2005).

In order to express the proteins described herein, delivery of nucleic acid sequences encoding the gene of interest can be delivered by several techniques. Examples of which include viral technologies (e.g. retroviral vectors, adenovirus vectors, adeno-associated virus vectors, alphavirus vectors and the like) and non-viral technologies (e.g. DNA/liposome complexes, micelles and targeted viral protein-DNA complexes) as described herein. Once inside the cell of interest, expression of the transgene can be under the control of ubiquitous promoters (e.g. EF-1α) or tissue specific promoters (e.g. Calcium Calmodulin kinase 2 (CaMKI) promoter, NSE promoter and human Thy-1 promoter). Alternatively expression levels may controlled by use of an inducible promoter system (e.g. Tet on/off promoter) as described in Wiznerowicz et al. (2005) Stem Cells 77:8957-8961.

Non-limiting examples of promoters include, but are not limited to, the cytomegalovirus (CMV) promoter (Kaplitt et al. (1994) Nat. Genet. 8:148-154), CMV/human β 3-globin promoter (Mandel et al. (1998) J. Neurosci. 18:4271-4284), NCX1 promoter, aMHC promoter, MLC2v promoter, GFAP promoter (Xu et al. (2001) Gene Ther., 8:1323-1332), the 1.8-kb neuron-specific enolase (NSE) promoter (Klein et al. (1998) Exp. Neurol. 150:183-194), chicken beta actin (CBA) promoter (Miyazaki (1989) Gene 79:269-277) and the β-glucuronidase (GUSB) promoter (Shipley et al. (1991) Genetics 10:1009-1018), the human serum albumin promoter, the alpha-1-antitrypsin promoter. To improve expression, other regulatory elements may additionally be operably linked to the transgene, such as, e.g., the Woodchuck Hepatitis Virus Post-Regulatory Element (WPRE) (Donello et al. (1998) J. Virol. 72: 5085-5092) or the bovine growth hormone (BGH) polyadenylation site.

Also provided herein is a polynucleotide probe or primer comprising at least 10, or alternatively, at least 17 or alternatively at least 20, or alternatively, at least 50, or alternatively, at least 75 polynucleotides, or alternatively at least 100 polynucleotides encoding SEQ ID NOS: 12 through 15 or their complements. Suitable probes and primers are described supra. It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. A probe useful for detecting the aforementioned mRNA is at least about 80% identical to the homologous region of comparable size contained in the previously identified sequences (identified above) which correspond to previously characterized polynucleotides of this invention. Alternatively, the probe is 85% identical to the corresponding gene sequence after alignment of the homologous region; and yet further, it exhibits 90% identity, or still further, at least 95% identical.

These probes can be used in radioassays (e.g. Southern and Northern blot analysis) to detect or monitor expression of the polynucleotides or polypeptides of this invention. The probes also can be attached to a solid support or an array such as a chip for use in high throughput screening assays for the detection of expression of the gene corresponding to one or more polynucleotide(s) of this invention.

The polynucleotides and fragments of the polynucleotides of the present invention also can serve as primers for the detection of genes or gene transcripts that are expressed in neuronal cells, for example, to confirm transduction of the polynucleotides into host cells. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of $E.$ $coli$ DNA polymerase, and reverse transcriptase. Primer length is the same as that identified for probes, above.

The invention further provides the isolated polynucleotides of this invention operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are well known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)), which contains maps, functional properties, commercial suppliers and a reference to GenEMBL accession numbers for various suitable vectors. Preferable, these vectors are capable of transcribing RNA in vitro or in vivo.

Expression vectors containing these nucleic acids are useful to obtain host vector systems to produce proteins and polypeptides. It is implied that these expression vectors must be replicable in the host organisms either as episomes or as an integral part of the chromosomal DNA. Suitable expression vectors include plasmids, viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells as described above and constructed using well known methods. See Sambrook and Russell (2001), supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; DEAE-dextran; electroporation; or microinjection. See Sambrook and Russell (2001), supra for this methodology.

The present invention also provides delivery vehicles suitable for delivery of a polynucleotide of the invention into cells (whether in vivo, ex vivo, or in vitro). A polynucleotide of the invention can be contained within a gene delivery vehicle, a cloning vector or an expression vector. These vectors (especially expression vectors) can in turn be manipulated to assume any of a number of forms which may, for example, facilitate delivery to and/or entry into a cell.

These isolated host cells containing the polynucleotides of this invention are useful for the recombinant replication of the polynucleotides and for the recombinant production of peptides and for high throughput screening.

The polynucleotides of this invention can be conjugated to a detectable label or combined with a carrier such as a solid support or pharmaceutically acceptable carrier. Suitable solid supports are described above as well as have suitable labels. Methods for attaching a label to a polynucleotide are known to those skilled in the art. See Sambrook and Russell (2001), supra.

Therapeutic Antibody Compositions

This invention also provides an antibody capable of specifically forming a complex with a protein or polypeptide of this invention, which are useful in the therapeutic methods of this invention. The term "antibody" includes polyclonal antibodies and monoclonal antibodies, antibody fragments, as well as derivatives thereof (described above). The antibodies include, but are not limited to mouse, rat, and rabbit or human antibodies. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. The antibodies are also useful to identify and purify therapeutic polypeptides.

This invention also provides an antibody-peptide complex comprising antibodies described above and a polypeptide that specifically binds to the antibody. In one aspect the polypeptide is the polypeptide against which the antibody was raised. In one aspect the antibody-peptide complex is an isolated complex. In a further aspect, the antibody of the complex is, but not limited to, a polyclonal antibody, a monoclonal antibody, a humanized antibody or an antibody derivative described herein. Either or both of the antibody or peptide of the antibody-peptide complex can be detectably labeled. In one aspect, the antibody-peptide complex of the invention can be used as a control or reference sample in diagnostic or screening assays.

Polyclonal antibodies of the invention can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, which induces the B-lymphocytes to produce IgG immunoglobulins specific for the antigen. This IgG is purified from the mammals serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a slow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods described in U.S. Pat. Nos. 7,279,559; 7,119,179; 7,060,800; 6,709, 659; 6,656,746; 6,322,788; 5,686,073; and 5,670,153.

The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/0) or the like, or heteromyelomas, fusion products thereof, or any cell or fusion cell derived therefrom, or any other suitable cell line as known in the art, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

In one embodiment, the antibodies described herein can be generated using a Multiple Antigenic Peptide (MAP) system. The MAP system utilizes a peptidyl core of three or seven radially branched lysine residues, on to which the antigen peptides of interest can be built using standard solid-phase chemistry. The lysine core yields the MAP bearing about 4 to 8 copies of the peptide epitope depending on the inner core that generally accounts for less than 10% of total molecular weight. The MAP system does not require a carrier protein for conjugation. The high molar ratio and dense packing of multiple copies of the antigenic epitope in a MAP has been shown to produce strong immunogenic response. This method is described in U.S. Pat. No. 5,229, 490 and is herein incorporated by reference in its entirety.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsried/Planegg, Del.), Biovation (Aberdeen, Scotland, UK) Biolnvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al., Proc. Natl. Acad. Sci. USA (1996) 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134.

Antibody derivatives of the present invention can also be prepared by delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873, 316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody derivatives also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies of the present invention can be performed using any known method such as, but not limited to, those described in U.S. Pat. Nos.

5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits. (1998) Advanced Drug Delivery Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417): 255-258; Jakobovits et al. (1993) Proc. Natl. Acad. Sci. USA 90(6):2551-2555; and U.S. Pat. No. 6,075,181.)

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies of this invention can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological Interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al., (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen.)

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Fd segments ($V_H$-$C_H$1-VH-$C_H$1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

If a monoclonal antibody being tested binds with protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski, et al.

(1985) Proc. Natl. Acad. Sci. USA 82:8653 or Spira, et al. (1984) J. Immunol. Methods 74:307.

The isolation of other hybridomas secreting monoclonal antibodies with the specificity of the monoclonal antibodies of the invention can also be accomplished by one of ordinary skill in the art by producing anti-idiotypic antibodies. Herlyn, et al. (1986) Science 232:100. An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

In some aspects of this invention, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

Antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), bismuth-213 ($^{213}$Bi), technetium-99m ($^{99m}$Tc), rhenium-186 ($^{186}$Re) and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, *pseudomonas* exotoxin A, staphylococcal enterotoxin A, abrin-A toxin, ricin A (deglycosylated ricin A and native ricin A), TGF-alpha toxin, cytotoxin from Chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies of the invention also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

III. Methods of the Invention

One aspect of the present invention relates to a method of preventing or reducing bleeding in a subject undergoing anticoagulant therapy by administering to the subject an effective amount of a factor Xa protein derivative. In one embodiment, the derivative has a modified active site and/or a modified Gla-domain thereby having either reduced or no procoagulant activity. The derivative acts as an antidote and substantially neutralizes the anticoagulant activity of the inhibitor. In one embodiment, the derivative is either Gla-deficient or Gla-domainless. The subject may be a mammal or more particularly, a human.

In another embodiment, the invention is directed to a method for selectively binding and inhibiting an exogenously administered factor Xa inhibitor in a subject. The method comprises administering to the patient an effective amount of a derivative of a factor Xa derivative as described above. The subject may be a cell or a mammal, such as a human.

Patients suitable for this therapy have undergone prior anticoagulant therapy, for example, they have been administered one or more of an anticoagulant, such as an inhibitor of factor Xa. Examples of anticoagulants that are factor Xa inhibitors, include but are not limited to, fondaparinux, idraparinux, biotinylated idraparinux, enoxaparin, fragmin, NAP-5, rNAPc2, tissue factor pathway inhibitor, DX-9065a, YM-60828, YM-150, apixaban, rivaroxaban, PD-348292, otamixaban, edoxaban, LY517717, GSK913893, low molecular weight heparin, and betrixaban, or any combination thereof. The source of various anticoagulants is found throughout the description.

In one aspect, the derivative has a modified active site and/or a modified or removed Gla domain. In one aspect, the factor Xa derivative has or exhibits no procoagulant activity. In this aspect, the derivative comprises at least amino acid residues 40 to 448, 45 to 448, or 46 to 448 of SEQ ID NO. 3 or equivalents thereof. In another aspect, the derivative comprises at least amino acid residues 45 to 139 and 195 to 448 or 46 to 139 and 195-448 of SEQ ID NO. 3 or equivalents thereof.

In another aspect of the invention, the fXa derivative retains the three dimensional structure of the active site of the fXa protein. Information regarding the three-dimensional structure of the des-Gla fXa may be found in Brandstetter, H et al. *J. Bio. Chem.*, 1996, 271:29988-29992.

In another aspect of the invention, the fXa derivatives are completely lacking the light chain. Other modifications of the heavy chain may comprise the catalytic domain of related serine proteases which are capable of binding inhibitors. The related serine proteases have catalytic domains which possess sufficient structural similarity to fXa catalytic domain and are therefore capable of binding small molecule fXa inhibitors. Examples of related serine proteases include, but are not limited to, mammalian proteases such as plasma kallikrein, thrombin and trypsin or the bacterial protease subtilisin. These derivatives further include modifications at the amino acids residues equivalent to the active site serine (SER379) or aspartic acid (ASP282) residues described herein.

In some embodiments, the factor Xa protein with reduced procoagulant activity comprises a modified light chain, wherein the modification is substitution, addition or deletion of the Gla-domain to reduce the phospholipid membrane binding of fXa. In some embodiments, the prime amino acid sequence of fXa is not changed, but the side chain of certain amino acids has been changed. Examples of the modified Gla-domain that reduces the phospholipid membrane binding of fXa comprises polypeptides or proteins having the primary amino acid sequence of SEQ ID NO. 3 or an equivalent thereof, with at least one amino acid substitution, addition, or deletion as compared to the Gla-domain of a wild type human factor Xa protein. In some embodiments, at least one amino acid being substituted or deleted is a γ-carboxyglutamic acid (Gla). Gla residues are shown in SEQ ID NO. 3 at amino acid positions 6, 7, 14, 16, 19, 20, 25, 26, 29, 32, and 39. In some embodiments, the antidote's primary amino acid sequence is identical to SEQ ID NO. 3 or equivalent thereof, but is an uncarboxylated, undercarboxylated or decarboxylated factor Xa protein. In some embodiments, the antidote is a des-Gla anhydro-fXa or des-Gla fX-S379A. In some embodiments, the factor Xa protein with reduced phospholipid membrane binding further comprises modification or deletion of the EGF1 and/or EGF2 (shown in FIG. 3 as amino acids 46 to 84 and 85 to 128, respectively) or a part, i.e. fragment of the EGF1 and/or EGF2 domains. In some embodiments, the entire light chain or substantially the entire light chain is modified or removed. For example, the modified fXa protein with reduced phospholipid membrane binding may contain only the heavy chain or the modified fXa may contain the heavy chain and a fragment of the light chain that contains Cys132, the amino acid residue that forms the single disulfide bond with Cys302 of the heavy chain in SEQ ID NO. 3. In some embodiments, the derivative comprises the amino acid sequence of SEQ ID NO. 12. In some embodiments, the derivative is the two chain polypeptide comprising SEQ ID NO. 13. In other embodiments, the derivative is the polypeptide of SEQ ID NO. 15. In other embodiments, the derivative is the polypeptide of SEQ ID NOs. 19-25.

In some embodiments, the factor Xa protein derivative comprises a modified heavy chain that contains the catalytic domain of said factor Xa protein. In some embodiments, at least one amino acid substitution is present at one or more amino acid position of fXa selected from the group consisting of Glu216, Glu218, Arg332, Arg347, Lys351, and Ser379 in SEQ ID NOS. 3 and 7 (Glu37, Glu39, Arg150, Arg165, Lys169, and Ser195 in chymotrypsin numbering, respectively). In some embodiments, the antidote is a factor Xa protein with active site serine (Ser379 in SEQ ID NOS. 3 and 7, Ser195 in chymotrypsin numbering) residue modified to dehydro-alanine or alanine Such modifications may be made to wild type fXa protein or to any of the modified fXa proteins or fragments described above. For example, the des-Gla anhydro-fXa with active site serine residues replaced by dehydro-alanine described in Example 1 has shown antidote activity.

In other embodiments, the derivative has reduced interaction with ATIII, cofactors fV/fVa and fVIII/fVIIIa as compared to wild-type or naturally occurring factor Xa. In some embodiments, at least one amino acid substitution is present at amino acid position Arg306, Glu310, Arg347, Lys351, Lys414 or Arg424 in SEQ ID NOS. 3 and 7 (Arg125, Glu129, Arg165, Lys169, Lys230 or Arg240 in chymotrypsin numbering, respectively). Such modifications may be made to wild type fXa protein or to any of the modified fXa proteins or fragments described above.

In other embodiments, the antidote is a protein comprising the amino acid sequence of a serine protease catalytic domain which can mimic the inhibitor binding capability of the fXa heavy chain. Such proteins may include mammalian proteases such as plasma kallikrein, thrombin, trypsin (or its bacterial homolog subtilisin) which have been recombinantly modified to lack serine protease activity capable of cleaving protein substrates but still possess the structural characteristics of the active site cleft.

Also provided by this invention are pharmaceutical compositions containing one or more of the modified factor Xa derivatives and a pharmaceutically acceptable carrier. The compositions are administered to a subject in need thereof in an amount that will provide the desired benefit, a reduction or stopping of bleeding. The compositions can be co-administered with any suitable agent or therapy that complements or enhances the activity of the factor Xa derivative. An example of such is a second agent capable of extending the plasma half-life of the antidote. Examples of suitable second agents include but are not limited to an anti-fXa antibody recognizing the exosite of fXa heavy chain or an alpha-2-macroglobulin bound fXa derivative. Formation of the complex between fXa derivative and a second agent (exosite antibody or alpha-2-macroglobulin) would block macromolecular interactions but retains the ability of active site dependent inhibitor bindings. Examples of anti-fXa antibodies suitable for co-administration include but are not limited to those described in Yang Y. H., et al, *J. Immunol.* 2006, 1; 177(11):8219-25, Wilkens, M and Krishnaswamy, S., *J. Bio. Chem.*, 2002, 277 (11), 9366-9374, and Church W R, et al, *Blood,* 1988, 72(6), 1911-1921.

In some embodiments, a factor Xa protein is modified by chemical, enzymatic or recombinant means. For example, the active site Ser379 may be chemically modified to dehydroalanine, and the Gla domain may be enzymatically removed by chymotrypsin digestion as described in Example 1. A modified fXa described herein may also be produced by recombinant means by modifying the sequence of the cDNA encoding wild-type fX (SEQ ID NO. 2) described in more details in Example 7 for direct expression of recombinant antidote (r-Antidote) or alternatively, a fX protein with the desired modification may be produced by recombinant means followed by activation to the modified fXa by an activator, such as a snake venom, e.g. Russell's viper venom, and complexes of fVIIa/tissue factor or fIXa/fVIIIa.

Subjects that will benefit from the administration of the compositions described herein and the accompanying methods include those that are experiencing, or predisposed to a clinical major bleeding event or a clinically significant non-major bleeding event. Examples of clinical major bleeding events are selected from the group consisting of hemorrhage, bleeding into vital organs, bleeding requiring re-operation or a new therapeutic procedure, and a bleeding index of ≥2.0 with an associated overt bleed. (Turpie AGG, et al, *NEJM*, 2001, 344: 619-625.) Additionally, the subject may be experiencing or predisposed to a non-major bleeding event selected from the group consisting of epistaxis that is persistent or recurrent and in substantial amount or will not stop without intervention, rectal or urinary tract bleeding that does not rise to a level requiring a therapeutic procedure, substantial hematomas at injection sites or elsewhere that are spontaneous or occur with trivial trauma, substantial blood loss more than usually associated with a surgical procedure that does not require drainage, and bleeding requiring unplanned transfusion.

In some embodiments, the antidote is administered after the administration of an overdose of a fXa inhibitor or prior to a surgery, which may expose subjects to the risk of hemorrhage.

In any of the methods described herein, it should be understood, even if not always explicitly stated, that an effective amount of the derivative is administered to the subject. The amount can be empirically determined by the treating physician and will vary with the age, gender, weight and health of the subject. Additional factors to be considered by the treating physician include but are not limited to the identity and/or amount of factor Xa inhibitor, which may have been administered, the method or mode that the antidote will be administered to the subject, the formulation of the antidote, and the therapeutic end point for the patient. With these variables in mind, one of skill will administer a therapeutically effective amount to the subject to be treated. It is contemplated that a therapeutically effective amount of the antidotes described herein sufficient to counteract, or substantially neutralize, an anticoagulant in a subject may contain from about 0.01 milligram of antidote per kilogram of a subject's body weight to 1 gram of antidote per kilogram of a subject's body weight of antidote. It is further contemplated that the antidote may be provided to the subject in a concentration a range of from about 10 nanomolar to about 100 micromolar, or about 10 nanomolar to about 5 micromolar, or about 100 nanomolar to about 2.5 micromolar.

The compositions can be administered in amounts that are effective for the antidote to selectively recognize and bind, either directly or indirectly, the factor Xa inhibitor in the subject. They also can be administered in amounts to substantially inhibit or substantially neutralize exogenously administered factor Xa inhibitors in a subject.

In still another aspect, the invention relates to a pharmaceutical composition for reversing or neutralizing the anticoagulant activity of a factor Xa inhibitor administered to a subject, comprising administering an effective amount of an antidote to the factor Xa inhibitor and a pharmaceutically acceptable carrier, with the proviso that the antidote is not plasma derived factor VIIa, recombinant factor VIIa, fresh frozen plasma, prothrombin complex concentrates and whole blood.

In some embodiments, the antidote is any one of the antidotes as described above. In some embodiments, the antidote is conjugated with a moiety capable of extending the circulating half-life of the antidote. In some embodiments, the moiety is selected from the group consisting of polyethylene glycol, an acyl group, a liposome, a carrier protein, an artificial phospholipid membrane, and a nanoparticle. For example, a non-active site lysine or cysteine residue of a fXa derivative described herein may be chemically modified to attach to a polyethylene glycol molecule. Other methods provided in Werle, M. & Bernkop-Schnürch, A. Strategies to Improve Plasma Half Life Time of Peptide and Protein Drugs, *Amino Acids* 2006, 30(4):351-367 may be used to extend the plasma half life of the antidotes of this invention.

In other embodiments of the invention, the half-life of the fXa derivative is improved by coupling the antidote to Fc carrier domains. In one embodiment, the antidote is coupled to an Fc fragment, such as an immunoglobulin peptide portion or an IgG1 fragment. In one embodiment, a chimeric protein is contemplated which comprises the fXa derivative and the immunoglobulin peptide portion. In yet another embodiment, the fXa derivative and the immunoglobulin peptide is coupled by a chemical reaction, such as a disulfide bond with the human IgG heavy chain and kappa light chain constant regions.

In some embodiments, the pharmaceutical composition further comprises an agent capable of extending the plasma half-life of the antidote. In another aspect, the pharmaceutical composition has been co-formulated with an agent capable of extending the plasma half-life of the antidote. In some embodiments, the co-administered or co-formulated agent is an anti-fXa antibody recognizing the exosite of fXa or an alpha-2-macroglobulin bound fXa derivative.

IV. Therapies

The present invention relates to a therapeutic method of preventing or reducing bleeding in a subject undergoing anticoagulant therapy. It is contemplated that the antidotes or derivatives of the present invention may be short-duration drugs to be used in elective or emergency situations which can safely and specifically neutralize a fXa inhibitor's conventional anticoagulant properties without causing deleterious hemodynamic side-effects or exacerbation of the proliferative vascular response to injury.

In one embodiment, the therapeutically effective amount of an antidote exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. The antidotes or derivatives of this invention may be administered once or several times when needed to neutralize the effect of a fXa inhibitor present in a subject's plasma. Preferably, the antidotes of this invention is sufficient when administered in a single dose.

It is contemplated that a typical dosage of the antidotes of the invention will depend on the actual clinical setting and inhibitor concentration in plasma. In in vitro assay, such as thrombin generation, clinical clotting assays such as aPTT, PT and ACT, a therapeutically effective amount of an antidote is expected to produce a correction of ex vivo clotting activity of 10% or more. In vitro assays indicate that an antidote/inhibitor ratio>1.0 should show reversal effect. The maximum plasma concentration for antidote is expected to be in the micro molar range, probably at 10 micromolar or below.

In a clinical setting, one of the criteria in determining the effectiveness of an antidote is that it produces any change of actual measures of bleeding. In clinical trials, categories of major bleeds include fatal hemorrhage, bleeds into vital organs (intracranial, intraocular, retroperitoneal, spinal, pericardial), any bleed requiring re-operation or a new therapeutic procedure (e.g., aspiration of an operated knee, thoracotomy tube insertion for hemothorax, endoscopic electrocoagulation, etc) or a bleeding index of >2.0 if it is associated with an overt bleed. The bleeding index is defined as the number of units of packed red cells or whole blood transfused plus the hemoglobin values before the bleeding episode minus the hemoglobin values after the bleed has stabilized (in grams per deciliter).

Another criterion for antidote efficacy in clinical settings is that it reduces clinically significant non-major bleeding. This category of hemorrhages include bleeding that is not major but is more than usual and warrants clinical attention, including epistaxis that is persistent or recurrent and in substantial amount or will not stop without intervention; rectal or urinary tract bleeding that does not rise to a level requiring a therapeutic procedure (e.g., new insertion of a Foley catheter or cystoscopic inspection), substantial hematomas at injection sites or elsewhere that are spontaneous or occur with trivial trauma; substantial blood loss; bleeding requiring unplanned transfusion. As used herein, "substantial blood loss" refers to amount of blood loss that is more than that amount usually associated with surgical procedure. Substantial blood loss leads to swelling that is managed conservatively because it falls short of requiring drainage.

In one embodiment, the derivatives of this invention have sufficient plasma circulating half life for substantially neutralizing the fXa inhibitor present in plasma. Activated fXa has essentially no circulating half life in humans, as it is effectively inhibited by ATIII, TFPI and other plasma inhibitors (Fuchs, H. E. and Pizzo, S. V., *J. Clin. Invest.*, 1983, 72:2041-2049). Inactive fXa has been shown to have a circulating half-life of 2-3 hours in humans. In a baboon model, the half-life of a fXa blocked in the active site by DEGR ([5-(dimethylamino)1-naphthalenesulfonyl]-glutamylglycylarginyl chloromethyl ketone) was approximately 10 hours or 2 hours, as determined by isotopic or enzyme-linked immunosorbent assays, respectively (Taylor, F. B. et al, *Blood*, 1991, 78(2):364-368).

It may be desirable to extend the half life of an antidote fXa derivative to 24-48 hours. It is contemplated that conjugation or addition of one or more of the following moieties will increase the plasma half life of an antidote:
  a) polyethylene glycol;
  b) an acyl group;
  c) liposomes and encapsulating agents;
  d) carrier proteins;
  e) artificial phospholipid membrane;
  f) immunoglobulin; and
  g) nanoparticle.

The conjugation site may not be limited to special chain or residue so long as the conjugation does not mask the inhibitor binding site(s) of the antidote. The antidotes described herein may be administered in combination with any one or more than one of the compounds described above.

In general, administered antibodies have much longer half life than circulating blood coagulation proteins. It is possible to use a complex consisting of Gla-domain deficient fXa and an antibody bound to the exosite of fXa as an antidote with extended circulating half life. Formation of a complex between fXa and the antibody targeting the exosite may reduce interaction of an Gla-domain deficient fXa with macromolecular substrates and inhibitors, such as prothrombin and antithrombin III, while leaving the active site cleft unperturbed so that the complex can act as an antidote to bind active site directed small molecule inhibitor. Formation of α-2-macroglobulin-fXa complex can also be of useful as an antidote for fXa small molecule inhibitors.

Efficacy of the antidotes in reversal of the anticoagulant activity of fXa inhibitors as well as its procoagulant activity may be determined by in vitro assays and animal models by those of skill in the art. Examples of in vitro assays are thrombin generation, anti-fXa units, clinical clotting assays such as aPTT, PT and ACT. An antidote of this invention is contemplated to be capable of producing 10% or more correction of ex vivo clotting activity. Several in vivo animal models of bleeding time and/or blood loss in, for example, rodents, such as mice, dogs and primates, such as monkeys, may be used to measure efficacy.

V. Pharmaceutical Compositions

The present invention further provides compositions comprising a fXa derivative and a pharmaceutically acceptable carrier.

"Pharmaceutically acceptable carriers" refers to any diluents, excipients, or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like, and consistent with conventional pharmaceutical practices.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The compositions of this invention are formulated for pharmaceutical administration to a mammal, preferably a human being. Such pharmaceutical compositions of the invention may be administered in a variety of ways, preferably parenterally.

It is contemplated that in order to quickly reverse the anticoagulant activity of a fXa inhibitor present in a patient's plasma in a emergency situation, the antidote of this invention can or may be administered to the systemic circulation via parental administration. The term "parenteral" as used herein includes subcutaneous, intravenous, intramuscular, intra-articular, intra-synovial, intrasternal, intrathecal, intrahepatic, intralesional and intracranial injection or infusion techniques. However, in cases where the fXa inhibitor being neutralized has a long plasma half life, a continuous infusion or a sustained release formulation may be required to bind to the fXa inhibitor and such free up the active fXa prior to the clearance of the fXa inhibitor from the body.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

In addition to dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific antidote employed, the age, body weight, general health, sex and diet, renal and hepatic function of the patient, and the time of administration, rate of excretion, drug combination, judgment of the treating physician or veterinarian and severity of the particular disease being treated.

VI. Kits

The invention further provides kits or packages. In some embodiments, the kit of the present invention comprises: (a) a first container containing a fXa inhibitor for regular administration for the treatment of thrombosis, and (b) a second container containing an antidote of this invention to be used in cases when there is an overdose of the fXa inhibitor in (a) or when normal hemostasis needs to be restored to stop or prevent bleeding. In other embodiments, the kit further comprises a label explaining when these two agents in (a) and (b) should be used.

The first and second container can be a bottle, jar, vial, flask, syringe, tube, bag, or any other container used in the manufacture, storage, or distribution of a pharmaceutical product. The package insert can be a label, tag, marker, or the like, that recites information relating to the pharmaceutical composition of the kit. The information recited will usually be determined by the regulatory agency governing the area in which the pharmaceutical composition is to be sold, such as the United States Food and Drug Administration. Preferably, the package insert specifically recites the indications for which the pharmaceutical composition has been approved. The package insert may be made of any material on which a person can read information contained therein or thereon. Preferably, the package insert is a printable material, such as paper, adhesive-backed paper cardboard, foil, or plastic, and the like, on which the desired information has been printed or applied.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius. Also, in these examples and elsewhere, abbreviations have the following meanings:

| | |
|---|---|
| aa = | amino acid |
| ab = | antibody |
| ACT = | activated clotting time |
| aPTT = | activated partial thromboplastin time |
| CHO cell = | Chinese hamster ovary cell |
| CHO dhfr(−)cells = | CHO cells lacking dhfr gene |
| fXa = | factor Xa |
| hr = | hour |
| INR = | international normalized ratio |
| IV = | intravenous |
| kg = | kilogram |
| M = | molar |
| mg = | milligram |
| mg/kg = | milligram/kilogram |
| mg/mL = | milligram/milliliter |
| min = | minute |
| mL = | milliliter |
| mM = | millimolar |
| nm = | nanometer |
| nM = | nanomolar |
| PO = | oral |
| PRP = | platelet rich plasma |
| PT = | prothrombin time |
| RFU = | relative fluorescence unit |
| s = | second |
| TF = | tissue factor |
| U/mL = | units/milliliter |
| μL or uL = | microliter |
| μM = | micromolar |
| μg = | microgram |

Example 1

Preparation of Des-Gla Anhydro-fXa by Chymotrypsin Digestion

Des-Gla anhydro-fXa was prepared according to the procedure of Morita, T. et al., *J. Bio. Chem.,* 1986, 261(9): 4015-4023 by incubating anhydro-fXa, in which dehydroalanine replaces the active-site serine, with chymotrypsin in 0.05 M Tris-HCl, 0.1 M NaCl, at pH 7.5 and 22° C. for 60 minutes. In a typical experiment setting, 0.5 milligrams/milliliter (mg/mL) anhydro-fXa was incubated with 5 units/milliliter (U/mL) α-chymotrypsin-agarose beads with gentle agitation. At the end of the reaction, the α-chymotrypsin-agarose beads were removed by centrifugation or filtration. This was followed by incubation with excess amount of inhibitors 4-amidino-phenyl-methane-sulfonyl fluoride (APMSF), tosyl-L-lysine chloromethyl ketone (TLCK), and tosyl-L-phenylalanine chloromethyl ketone (TPCK) to quench the residual fXa activity or any activity of chymotrypsin possibly leached from the beads. Gla-domain fragment and inhibitors were removed from the final product, des-Gla anhydro-fXa, by an Amicon Ultra Centrifugal filter device (YM10 membrane) or by conventional dialysis. Concentrating or buffer exchange, if necessary, was also achieved at the same time.

Figure 5:
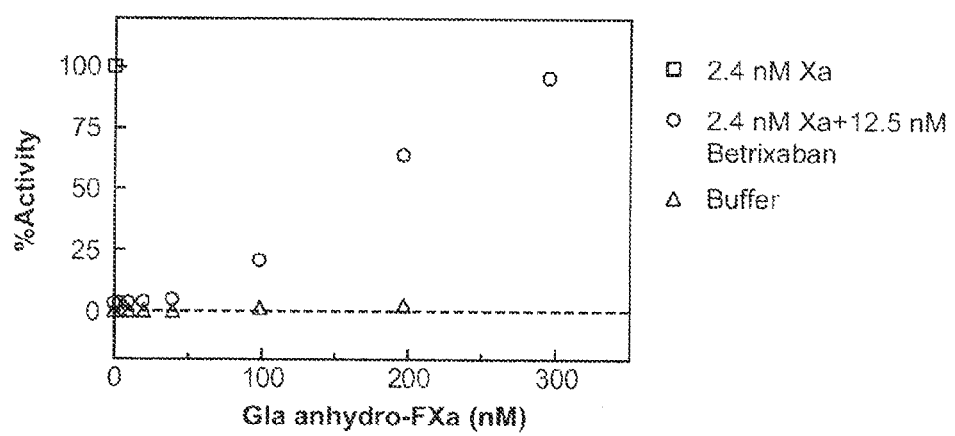
FIG. 5 shows that anhydro-fXa with its Gla-domain intact reverses fXa inhibition by betrixaban in a purified system containing active fXa and betrixaban (open circle), while anhydro-fXa alone has negligible procoagulant activity (open triangle) compared with active fXa. FXa chromogenic activity was normalized to active fXa in the absence of any inhibitor (open square). This is more thoroughly described in Example 4. The data show that anhydro-fXa is inactive toward fXa substrate yet retains the fXa inhibitor binding ability.

The Gla-containing anhydro-fXa was prepared according to the procedure reported by Nogami et al., *J. Biol. Chem.,* 1999, 274(43):31000-7. As shown in FIG. 5, the Gla-containing anhydro-fXa has diminished enzymatic activity but is capable of binding fXa inhibitors such as betrixaban. This is described in detail in Example 4.

Chymotrypsin digestion of active fXa can be carried out according to above procedure without using APMSF. Clotting activity of active fXa was determined before the chymotrypsin digestion, and after 15, 30 and 60 minutes of chymotrypsin digestion according to the procedure described in Example 3 below. FIG. 7 shows complete loss of clotting activity after 30 minutes of chymotrypsin digestion. The incubation time were extended to 60 minutes to ensure complete removal of the Gla domain.

Example 2

Thrombin Generation Assay in Platelet Poor Plasma (PPP) or Platelet Rich Plasma (PRP)

In this example, human platelet poor or platelet rich plasma samples were prepared from blood of healthy donors drawn into 0.32% citrate. PRP and PPP were prepared by spinning the anticoagulated blood at ~100× gravity or 1000× gravity for 20 minutes, respectively, at room temperature. 75-100 microliter (uL) plasma was mixed with $CaCl_2$ and Z-Gly-Gly-Arg-aminomethylcoumarin (Z-GGR-AMC, a thrombin fluorogenic substrate). Tissue factor (Innovin, Dade Behring) was added to initiate the generation of thrombin. For a typical experiment, the reaction mixture contained 15 millimolar (mM) $Ca^{2+}$, 100 micromolar (μM) Z-GGR-AMC, and 0.1 nanomolar (nM) tissue factor (TF) (Innovin). Thrombin formation was monitored continuously at 37° C. by a fluorometric plate reader (Molecular Devices) measuring the relative fluorescence units (RFU) Inhibitor and antidote, when present, were pre-incubated with plasma for 20 minutes at room temperature before initiation of thrombin generation.

The results of various experiments using this assay may be found in FIGS. 4, 6, and 9.

Example 3

Clotting Prolongation Assays

Two clotting assay formats were used to test the effects of factor Xa inhibitors and the antidote on clotting prolongation. In the first format, a 96-well plate was used to measure multiple samples at the same time. In the second assay format, aPTT was measured with a conventional coagulation instrument (MLA Electra 800 automatic coagulation timer).

In the 96-well plate format method, human platelet poor plasma or platelet rich plasma was prepared similarly as procedures in Example 2. 75-100 μL plasma was recalcified with $CaCl_2$, incubated at 37° C. for 3 minutes and clot formation was initiated by adding tissue factor (Innovin, Dade Behring) or an aPTT reagent (Actin FS, Dade Behring). Change of OD405 was monitored continuously by a plate reader (Molecular Devices). Clotting time was defined as the time (second) when the half maximal value of absorbance (OD405 nm) change was reached. Factor Xa inhibitor and antidote, when present, were pre-incubated with plasma at room temperature for 20 minutes before initiation of the reaction.

When an active fXa was tested for its clotting activity as shown in FIG. 7, 75-100 uL fX deficient plasma (George King Bio-Medical, Inc.) was recalcified with $CaCl_2$, incubated at 37° C. for 3 minutes and fXa products following chymotrypsin digestion was added to the plasma to initiate clot formation. Change of OD405 was continuously monitored by a plate reader as described before.

In FIG. 13, the effect of 400 nM betrixaban on aPTT prolongation of normal human plasma and the reversal of betrixaban inhibitory effect by antidote des-Gla anhydro-fXa was measured with a MLA Electra 800 Automatic coagulation timer. 100 μL pooled human plasma was mixed with 400 nM betrixaban and different concentration of antidote. aPTT reagent (Actin FS, Dade Behring) and $CaCl_2$ were added per manufacturer's instructions for measurement of clotting times.

Results of additional experiments using this assay may be found in FIGS. 10 and 11.

Example 4

Reversal of Inhibition of fXa by Betrixaban by Anhydro-fXa or Des-Gla Anhydro-fXa To measure the inhibition of fXa activity by betrixaban and reversal of its inhibitory effect, purified active fXa, different concentrations of betrixaban and anhydro-fXa or des-Gla anhydro-fXa were added to 20 mM Tris, 150 mM NaCl, 5 mM $Ca^{2+}$, and 0.1% Bovine Serum Albumin (BSA). After incubation at room temperature for 20 minutes, 100 μM Spectrozyme-fXa (a factor Xa chromogenic substrate, American Diagnostica) was added to the mixture and the rate of substrate cleavage was monitored continuously for 5 minutes at 405 nanometer (nm) by a plate reader. In FIG. 5, the chromogenic activity was normalized to active fXa in the absence of any inhibitor. Initial velocity of product formation as a function of inhibitor and antidote concentration was analyzed by nonlinear regression to estimate the affinity of betrixaban to the antidote (FIG. 8).

The effect of the antidote des-Gla anhydro-fXa on thrombin activity toward a chromogenic substrate 52288 (200 μM)

was measured similarly as before with or without Argatroban, a specific small molecule IIa inhibitor. As expected, the antidote (538 nM) does not affect the amidolytic activity of IIa (5 nM) or its inhibition by 50 nM Argatroban.

Example 5

Preparation of fXa with Decarboxylated γ-Carboxyglutamic Acid Residues

A fXa derivative with decarboxylated γ-carboxyglutamic acid residues can be prepared by treating fXa protein, for example, based on the procedure reported by Bajaj, et al. *J. Biol. Chem.*, 1982, 257(7):3726-3731. 2 to 5 mg of purified or recombinant fXa in 2 mL of 0.1 Molar ammonium bicarbonate at pH 8.0 is lyophilized. The resulting powder is sealed under a vacuum of less than 20 μm and heated at 110° C. for various periods of time to obtain decarboxylated fXa.

Example 6

Preparation of Recombinant des-Gla fXa-S379A

The fXa derivatives may be produced by recombinant DNA method with one of the following procedures based on fX cDNA (SEQ ID NO. 2) for expressing fX (SEQ ID NOS. 1, 3) or fXa derivatives (SEQ ID NOS. 4, 5, 9, and 11) in a suitable host organism according to general procedures of mutagenesis and molecular biology.

Recombinant fX and fX derivatives can be expressed in, for example, human embryonic kidney cells HEK293 based on procedures described in Larson, P. J., et al, *Biochem.*, 1998, 37:5029-5038, and Camire, R. M., et al, *Biochem.*, 2000, 39, 14322-14329. Recombinant fX can be activated to rfXa by factor X activator Russell's Viper Venom (RVV). rfXa can be further processed to des-Gla anhydro-fXa based on procedures described in Example 1.

Recombinant fX-S379A (S195A in chymotrypsin numbering) with the active site serine residue being replaced by alanine, and preferably the activated fXa mutant, rfXa-S379A, may be expressed, for example, in Chinese Hamster Ovary (CHO) cells based on procedures described by Sinha et al., *Protein Expression and Purif.* 1992, 3: 518-524; Wolf, D. L. et al, *J. Biol. Chem.*, 1991, 266(21):13726-13730.

Des-Gla fXa-S379A may be prepared by chymotrypsin digestion of fXa-S379A according to procedures described in Example 1.

More preferably, Des-Gla fXa-S379A may be expressed directly according to previous procedures with deletion of Gla-domain fragment by mutagenesis procedures. For example, recombinant protein expression can be used to express: des-Gla(1-39)-fXa-S379A, after removal of Gla-domain fragment 1-39 of SEQ ID NO. 3; des-Gla(1-44)-fXa-S379A, equivalent to SEQ ID NO. 10 with dehydroalanine being replaced by alanine; and des-Gla(1-45)-fXa-S379A with entire Gla-domain being removed (SEQ ID NO. 11).

Further truncations at EGF1 or EGF1 plus EGF2 domain (FIG. 2) can also be made to express des(1-84)-fXa-S379A or des(1-128)-fXa-S379A derivatives.

Example 7

Expression of Recombinant fXa Mutant in CHO Cell

This example describes the recombinant protein expression construct and the cell line for the direct expression of a Gla-domainless fXa-S379A (S195A in chymotrypsin numbering) variant. The recombinant antidote does not require activation or chemical modification steps necessary to produce the pd-Antidote and has comparable affinity to the plasma derived protein in the in vitro assays discussed herein.

In this example, a fXa mutant (SEQ ID NO. 13, Table 13) was directly expressed in CHO cell (see FIG. 14 for expression vector) and functional protein was purified from conditioned medium as described below. Recombinant antidote (r-Antidote) functional activity was tested in vitro and in animal model (Example 8).

PCR was used to mutate the cDNA sequence of fX (SEQ ID NO. 2) in three regions. The first mutation was the deletion of 6-39 aa in the Gla-domain of FX (SEQ ID NO. 3, FIG. 3). The second mutation was replacing the activation peptide sequence 143-194 aa with -RKR- (SEQ ID NO: 40). This produced a -RKRRKR- linker (SEQ ID NO: 41) connecting the light chain and the heavy chain. Upon secretion, this linker is removed in CHO resulting in a two-chain fXa molecule. The third mutation is mutation of active site residue S379 to an Ala residue.

The polypeptide produced by the cDNA (SEQ ID NO. 16) just described is described in Table 12 (SEQ ID NO. 12). The alignment of the cDNA to the polypeptide is shown in Table 17. The two-chain fXa molecule produced after secretion is a light chain fragment described in Table 14 (SEQ ID NO. 14) and a heavy chain fragment described in Table 15 (SEQ ID NO. 15).

The first 1-5 aa in fX sequence was reserved and used to connect the polypeptide of fXa mutant to the prepro peptide of fX (SEQ ID NO. 1, FIG. 1), ensuring proper processing of the prepro peptide in fXa mutant.

Figure 14:
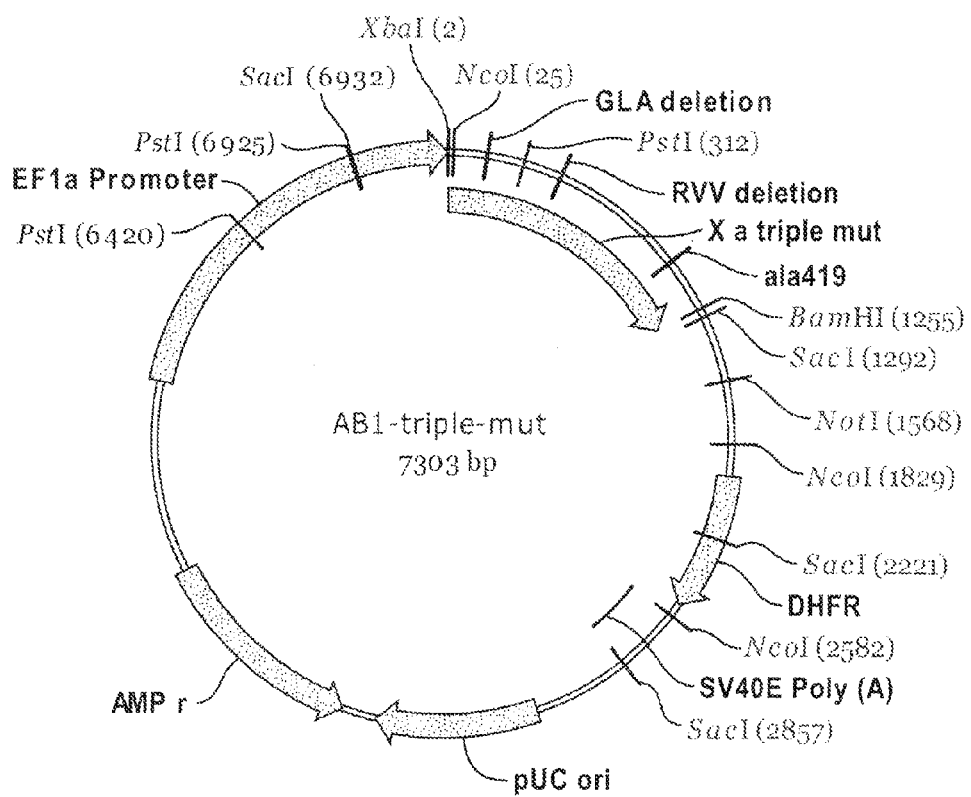
FIG. 14 shows the map of the DNA construct for expression of the fXa triple mutant (SEQ ID NO. 12) in CHO cells. Plasmid DNA was linearized and transfected into CHO dhfr(−) cells. Cells were selected using tetrahydrofolate (HT) deficient media plus methotrexate (MTX). Stable clones were screened for high protein expression by ELISA. The fXa triple mutant was produced in serum free medium and purified by combination of ion exchange and affinity columns. The numbering in the map was based on polynucleotide sequence encoding human fX SEQ ID NO. 1. For example, an alanine mutation at the active site S419 (SEQ ID NO. 1) is equivalent to the mutation at S379 (SEQ ID NO.3) of mature human fX discussed throughout the application and more particularly, Example 7. Primers used to construct the polynucleotide encoding the r-Antidote triple mutant are listed in Table 28.

DNA sequence encoding the polypeptide of fXa mutant described above was sequenced and inserted to the expression vector shown in FIG. 14. The polynucleotide of the expression vector is shown in SEQ ID NO. 17. Plasmid DNA was linearized and transfected into CHO dhfr(−) cells. Cells were selected using tetrahydrofolate (HT) deficient media plus methotrexate (MTX). Stable clones were screened for high protein expression using a fX ELISA kit (Enzyme Research Laboratories, Catalogue Number FX-EIA). FXa mutant protein was expressed in serum free medium and conditioned medium was harvested and processed for purification.

Target protein in the conditioned medium can be isolated by ion exchange chromatography and subsequently purified by single step affinity chromatography (such as an anti-fXa antibody coupled to a matrix) or by a combination of several chromatography steps such as hydrophobic and size exclusion matrices. The affinity purifications may include chromatographic material that selectively binds to fXa active site cleft, such as benzamidine-sepharose or soybean trypsin inhibitor-agarose (STI-Agarose).

Figure 15:
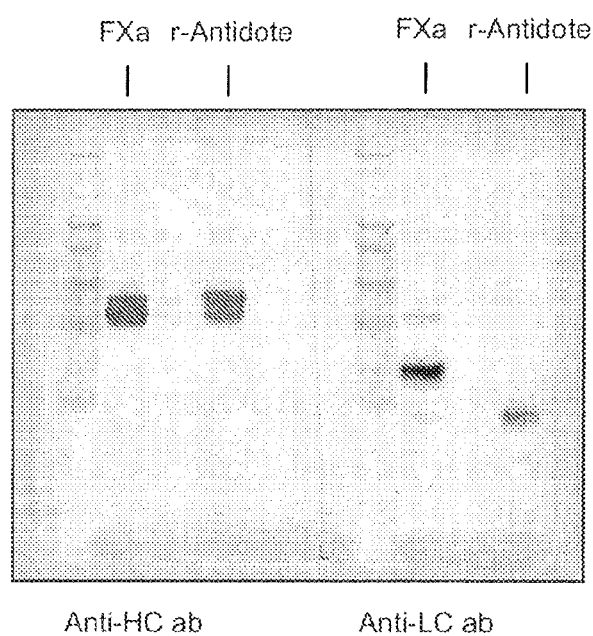
FIG. 15 shows a Western blot of purified r-Antidote by ion exchange and affinity purification. Upon reduction of the disulfide bond which connects the light and heavy chains, the r-Antidote heavy chain migrates at expected molecular weight similar to that of plasma derived fXa. Deletion of 6-39 aa in the Gla-domain of fXa mutant results in a lower molecular weight band of the r-Antidote light chain compared to normal FXa.

FIG. 15 shows the Western blots of affinity (STI-Agarose, Sigma Catalog # T0637) purified fXa mutant using monoclonal antibodies (Enzyme Research Laboratories, FX-EIA) recognizing fX heavy and light chain, respectively. Upon reduction of the disulfide bond which connects the light and heavy chain, r-Antidote shows the heavy chain band of expected mobility (similar to plasma derived fXa) in the Western blot. Deletion of amino acid residues 6-39 in the Gla-domain of fX mutant results in a lower molecular weight band for the light chain of r-Antidote compared to plasma derived fXa. Position of the molecular weight marks can also be seen on the blot.

FIGS. B and 15C shows a SDS-PAGE and Western blot of purified r-Antidote by ion exchange and affinity purification followed by size exclusion chromatography using a Superdex 75 10/300 GL column (GE Healthcare, Cat#17-5174-01).

Example 8

In Vivo Mouse Model

The pharmacokinetic and pharmacodynamic (PK-PD) profile of betrixaban in male C57Bl/6 mice with or without administrating antidote were tested. Single oral administration of betrixaban was dosed at 0, 15, 25, and 75 mg/kg for controls groups. 15 mg/kg was used for antidote treated group. A single intravenous (IV) injection of antidote (300 ug/200 μL) or vehicle (normal saline, 200 μL) was administered 5 minutes prior to the 1.5 hr. time point.

At 1.5, 2.0, and 4.0 hrs following oral administration of betrixaban, mice were anesthetized with a ketamine cocktail (SC) and exsanguinated via cardiac puncture. Blood samples (0.5 mL) were obtained in 50 μL trisodium citrate. Whole blood INR was measured using Hemochron Jr. cartridges (International Technidyne Corporation) per the manufacturer's instructions. Mouse platelet poor plasma was prepared by centrifugation for betrixaban and antidote (ELISA) plasma concentration determinations.

For recombinant antidote (r-Antidote) experiment, mice were orally dosed with betrixaban at 0, 15, 25, and 75 mg/kg for control groups. 15 mg/kg was used for antidote (300 μg/200 μL) treated group. Samples were taken at 1.5 hr after oral administration of betrixaban (5 min. following antidote injection).

Figure 16:
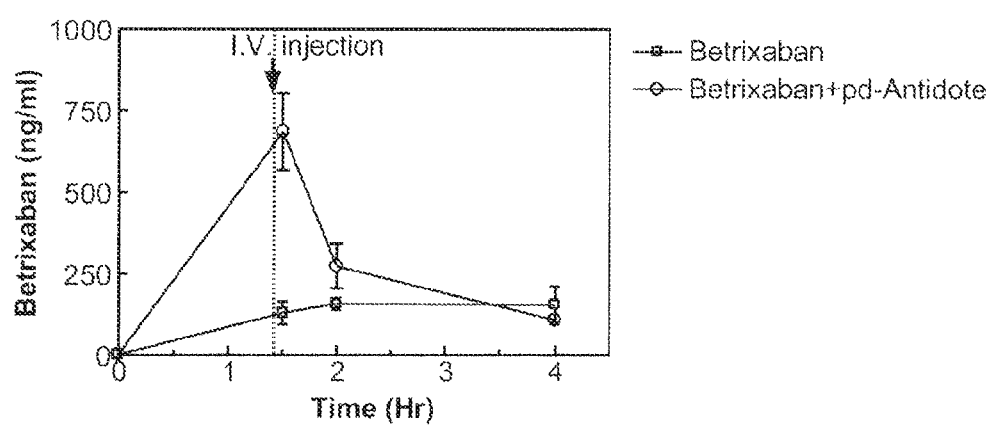
FIG. 16 shows betrixaban plasma level in mice (n=7-10 per group) after oral administration of betrixaban alone (15 mg/kg), or betrixaban (15 mg/kg) followed by intravenous injection (300 μg, IV) of plasma derived antidote (pd-Antidote) prepared according to Example 1. pd-Antidote was administered 5 minutes prior to the 1.5 hr. time point, and mouse blood samples (0.5 mL) were taken at 1.5, 2.0, and 4.0 hrs following oral administration of betrixaban. Whole blood INR, betrixaban and antidote plasma levels were analyzed. Betrixaban level (Mean±SEM) in mouse plasma was plotted as a function of time for mice after 15 mg/kg (open square) and 15 mg/kg followed by antidote injection (open circle). The PK-PD correlation of antidote treated group at 1.5 hr time point (5 min after antidote injection) was summarized in Table A. Single injection of the antidote resulted in >50% reduction of functional betrixaban based on INR measurements. This is more thoroughly described in Example 8.
Figures 17A, 17B:
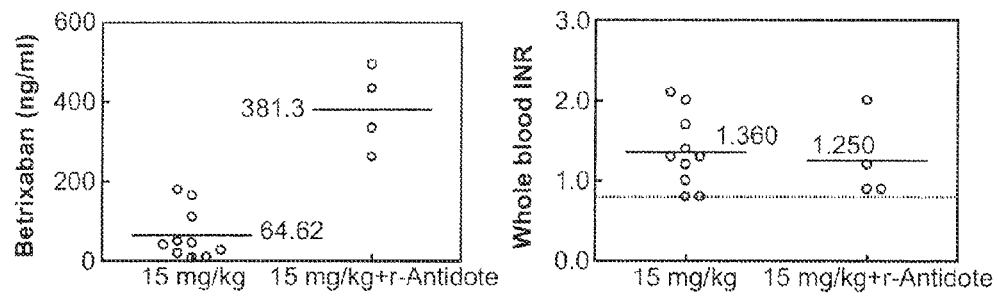
FIGS. 17A and B shows the results of a mouse experiment with purified r-Antidote (n=4-10 per group). Betrixaban level in mouse plasma (FIG. 17A) and whole blood INR (FIG. 17B) were compared after oral administration of betrixaban alone (15 mg/kg) or betrixaban (15 mg/kg) followed by intravenous injection (300 μg) of r-antidote. Mean values for each treated group were indicated. As summarized in Table B, single IV injection of the r-antidote resulted in >50% correction of ex vivo whole blood INR, justifying effective neutralization of fXa inhibitors by the antidote via a single or multiple injections or other regimes. These results demonstrate that the fXa variants of this invention have potential of acting as universal antidotes to reverse the anticoagulant effect of fXa inhibitors in patients with bleeding or other medical emergencies. This is more thoroughly described in Example 8.

As shown in FIGS. 16 and 17 and Tables A and B, single injection (300 μg, IV) of plasma derived antidote (pd-Antidote) or recombinant fXa mutant (r-Antidote) to mice following administration of betrixaban (15 mg/kg, PO) effectively captured the inhibitor in vivo. PK-PD correlation of whole blood INR and antidote plasma concentration (Tables A and B) indicated >50% reduction of functional betrixaban based on INR measurements, and justified effective neutralization of fXa inhibitors by the antidote via multiple injections or other regimes. It is contemplated that these results demonstrate that the fXa derivatives of this invention have potential of acting as universal antidotes to reverse the anticoagulant effect of fXa inhibitors in patients with bleeding or other medical emergencies.

TABLE A

PK-PD correlation in pd-Antidote treated mice at 1.5 hr after 15 mg/kg Betrixaban oral administration (5 min after antidote injection)

| | pd-Antidote treated animal | | | | | | | |
|---|---|---|---|---|---|---|---|---|
| | 1 | 2 | 3 | 4 | 5 | 6 | 7 | Mean |
| Betrixaban (ng/mL) | 673 | 793 | 1170 | 415 | 217 | 664 | 879 | 687 |
| Expected INR | 4.2 | 4.5 | 5.2 | 3.3 | 2.3 | 4.1 | 4.7 | 4.0 |
| Measured INR | 2.3 | 2.3 | 3.3 | 0.8 | 0.8 | 1.5 | 2.0 | 1.9 |
| % Correction | 63.9 | 66.6 | 52.3 | 100 | 100 | 83.1 | 74.4 | 77.2 |

TABLE B

PK-PD correlation in r-Antidote treated mice at 1.5 hr after 15 mg/kg Betrixaban oral administration (5 min after antidote injection)

| | r-Antidote treated animal | | | | |
|---|---|---|---|---|---|
| | 1 | 2 | 3 | 4 | Mean |
| Betrixaban (ng/mL) | 434 | 262 | 335 | 494 | 381 |
| Expected INR | 3.2 | 2.5 | 2.8 | 3.5 | 3.0 |
| Measured INR | 2.0 | 0.9 | 1.2 | 0.9 | 1.3 |
| % Correction | 50.0 | 94.1 | 80.0 | 93.6 | 77.3 |

Figure 22A:
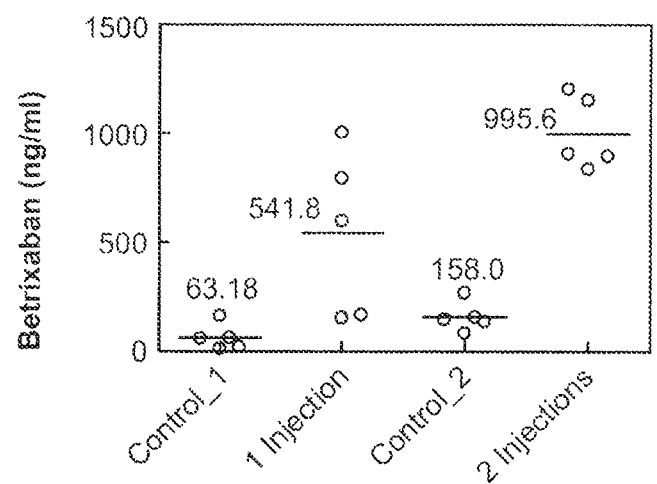
FIGS. 22A and B shows the results of a mouse experiment with a single IV injection (1 injection) or two injections (2 injections) of the r-antidote (n=5 per group, 312 ug/200 ul r-Antidote). Betrixaban level in plasma (FIG. 22A) were compared after oral administration of betrixaban (15 mg/kg) followed by intravenous injection of vehicle or r-Antidote (see Example 8 for details).
Figure 22B:
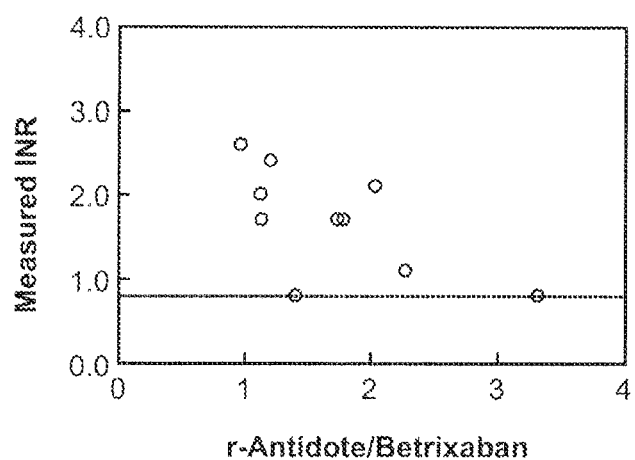
FIG. 22B demonstrates that measured INR decreases as the ratio of antidote/betrixaban increases in mouse plasma following single and double injections of the antidote.

FIG. 22 shows mouse experiment with a single IV injection (1 injection) or two injections (2 injections) of the r-antidote (n=5 per group, 312 ug/200 ul r-Antidote) following oral administration of betrixaban (15 mg/kg). For the single injection group, mouse blood samples were taken at 1 hr. following oral administration of betrixaban. Vehicle (control_1) or r-Antidote (1 injection) was administered 5 min prior to the 1 hr. time point. For the double injection group, vehicle or r-Antidote was injected at 55 min and repeated at 115 min following oral administration of betrixaban. Mouse blood samples were taken at 2 hr. for vehicle (control_2) and r-Antidote (2 injections) treated mice. Measured INR as a function of antidote/betrixaban ratio in mouse plasma following single or double injections of the antidote was shown in FIG. 22 B.

Example 9

In Vitro Reversal of Rivaroxaban and Apixaban by Antidote

As expected, the antidotes contemplated by this invention were also able to bind and neutralize other active site directed fXa inhibitors. Tables C and D show in vitro correction of inhibition by betrixaban, rivaroxaban and apixaban by pd-Antidote and r-Antidote. Purified fXa (3.0 nM), inhibitor (7.5 nM), and different concentrations of antidote were incubated for 10 min at 22° C. in a buffer with 20 mM Tris, 150 mM NaCl, 0.1% BSA, pH7.4. fXa activity was assayed similar to Example 4.

TABLE C

| % Correction of inhibition by fXa inhibitors | | | |
|---|---|---|---|
| pd-Antidote (nM) | Betrixaban | Rivaroxaban | Apixaban |
| 0 | 0 | 0 | 0 |
| 10.2 | 13.1 | 10.6 | 6.5 |
| 20.4 | 34.8 | 37.4 | 11.4 |
| 40.7 | 47.1 | 46.8 | 15.0 |
| 61.1 | 68.4 | 55.7 | 40.3 |
| 101.8 | 67.5 | 69.4 | 52.3 |
| 162.9 | 80.5 | 74.0 | 56.0 |
| 203.7 | 82.6 | 72.6 | 60.2 |

TABLE D

| % Correction of inhibition by fXa inhibitors | | | |
|---|---|---|---|
| r-Antidote (nM) | Betrixaban | Rivaroxaban | Apixaban |
| 0 | 0 | 0 | 0 |
| 9.3 | 21.5 | 23.2 | 13.3 |
| 18.6 | 52.7 | 54.2 | 33.5 |
| 37.2 | 75.5 | 72.6 | 49.9 |
| 55.8 | 86.5 | 79.9 | 59.2 |
| 93.1 | 94.9 | 89.1 | 64.4 |

TABLE D-continued

% Correction of inhibition by fXa inhibitors

| r-Antidote (nM) | Betrixaban | Rivaroxaban | Apixaban |
|---|---|---|---|
| 148.9 | 99.3 | 96.7 | 74.8 |
| 186.1 | 99.5 | 94.8 | 72.6 |

As shown in Table C, 204 nM pd-Antidote produces at least 60% correction of the inhibitory effects of tested inhibitors, while in Table D >95% correction of inhibition was achieved by the r-Antidote (186 nM) for betrixaban and rivaroxaban, and >70% reversal of apixaban.

Example 10

In Vitro Reversal of Betrixaban by r-Antidote

In Table E, the effect of recombinant antidote protein on reversal of anticoagulation by betrixaban was tested in a human plasma clotting assay. The effect of 300 nM and 400 nM betrixaban on aPTT prolongation of plasma and the reversal of inhibitory effect was measured by a MLA Electra 800 Automatic coagulation timer. 100 µL pooled citrate anticoagulated human plasma was mixed with 300 nM or 400 nM betrixaban and different concentrations of antidote. aPTT reagent (Actin FS, Dade Behring) and CaCl$_2$ were added per manufacturer's instructions.

TABLE E r-Antidote reversal of anticoagulant activity of betrixaban

| | aPTT (sec) | Fold Change | % Correction of anti-coagulation |
|---|---|---|---|
| Control human plasma | 35.2 | 1.00 | — |
| 300 nM Betrixaban | 61.8 | 1.76 | — |
| 300 nM Betrixaban + 570 nM r-Antidote | 38.3 | 1.09 | 88 |
| 300 nM Betrixaban + 760 nM r-Antidote | 38.2 | 1.09 | 88 |
| 300 nM Betrixaban + 1140 nM r-Antidote | 38.1 | 1.08 | 90 |
| 400 nM Betrixaban | 66.3 | 1.88 | — |
| 400 nM Betrixaban + 380 nM rAntidote | 47.1 | 1.34 | 61 |
| 400 nM Betrixaban + 570 nM rAntidote | 39.9 | 1.13 | 85 |
| 400 nM Betrixaban + 760 nM rAntidote | 39.9 | 1.13 | 85 |
| 400 nM Betrixaban + 1140 nM rAntidote | 37.8 | 1.07 | 92 |
| 400 nM Betrixaban + 1520 nM rAntidote | 39.4 | 1.12 | 86 |
| 1140 nM rAntidote | 38.9 | 1.11 | — |
| 1520 nM rAntidote | 38.8 | 1.10 | — |

Example 11

In Vitro Reversal of Low Molecular Weight Heparin ("LMWH") by r-Antidote

Figure 18:
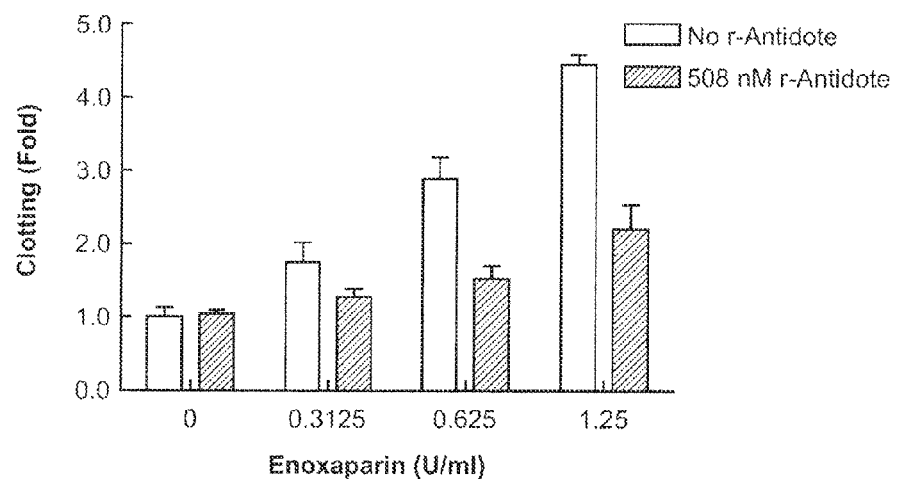
FIG. 18 shows r-Antidote reversal of the inhibitory effect of enoxaparin in a 96-well turbidity change clotting assay. The results are essentially similar to pd-Antidote (FIG. 11) indicating both fXa derivatives have comparable functional antidote activity. 50 nM r-Antidote substantially corrected (>75%) the inhibitory effect of 1.25 U/mL enoxaparin. The assay protocol is presented in Example 11.

In FIG. 18, the effect of r-Antidote to reverse the inhibitory effect of LMWH enoxaparin (Sanofi-Aventis) was tested by turbidity changes in human plasma. Enoxaparin (0-1.25 U/mL) was incubated at 22° C. for 20 min with or without 508 nM r-Antidote. Turbidity changes were measured according to procedures described in Example 3. 508 nM r-Antidote substantially corrected (>75%) the inhibitory effect of 0.3125-1.25 U/mL Enoxaparin.

Figure 19:
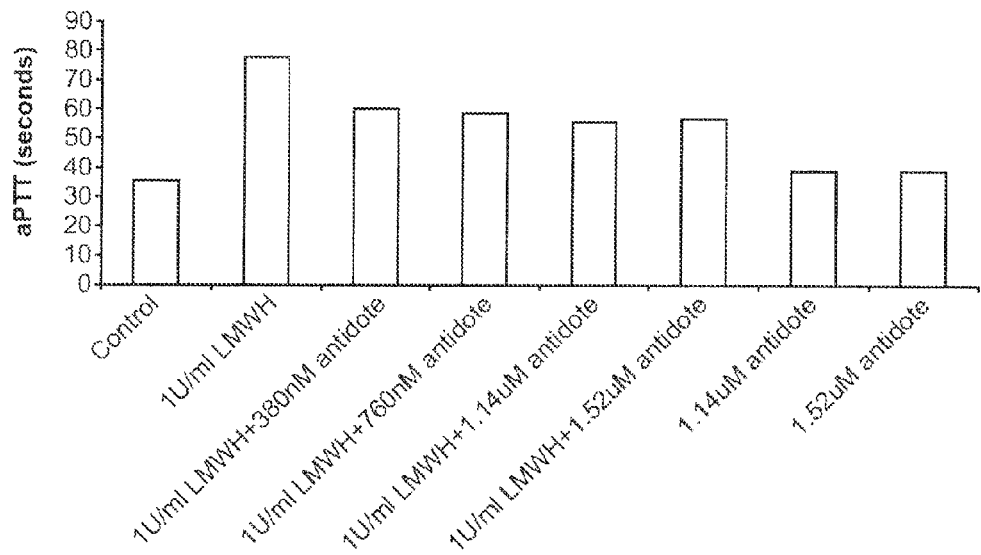
FIG. 19 shows r-Antidote reversal of the inhibitory effect of low molecular weight heparin (LMWH) as tested in human plasma clotting assay. Both

In FIG. 19, the effect of r-Antidote on reversal of anticoagulation by a low molecular weight heparin (LMWH enoxaparin, Sanofi-Aventis) was tested in a human plasma clotting assay. The effect of 1 antiXa Unit/mL LMWH on aPTT prolongation of plasma and the reversal of inhibitory effect was measured by a MLA Electra 800 Automatic coagulation timer. 100 µL pooled citrate anticoagulated human plasma was mixed with enoxaparin and different concentrations of antidote. Prior to measurement of clotting time, aPTT reagent (Actin FS, Dade Behring) and CaCl$_2$ were added per manufacturer's instructions. Addition of 1.14 µM recombinant antidote produced a 52% correction of anticoagulation produced by 1 Unit/mL enoxaparin.

Example 12

In Vitro Reversal of Rivaroxaban by r-Antidote

Figure 20:
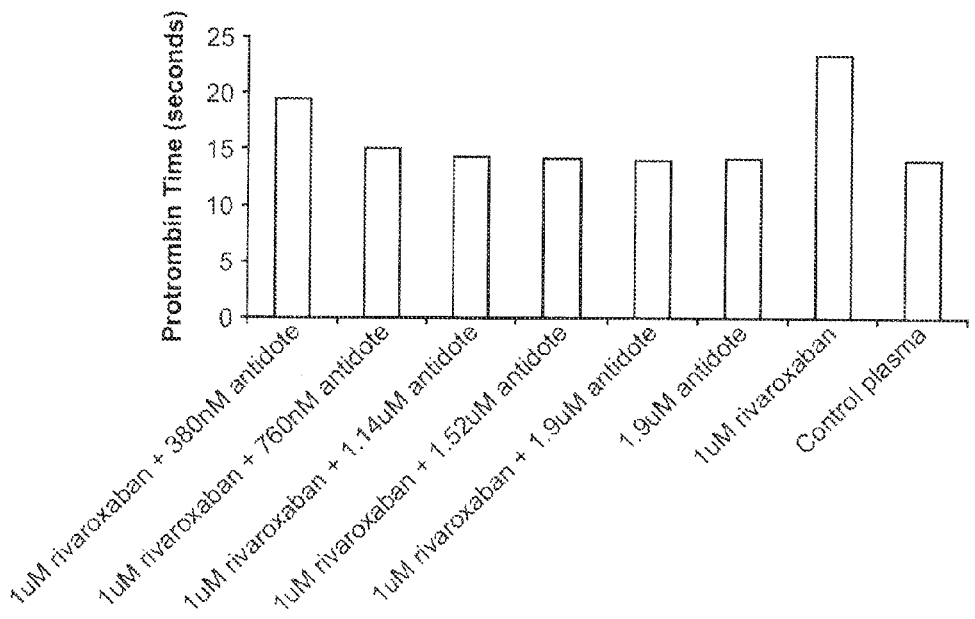
FIG. 20 shows the r-Antidote reversal of the anticoagulation effect of rivaroxaban. This is more thoroughly discussed in Example 12.

In FIG. 20, the effect of recombinant antidote protein on reversal of anticoagulation by a small molecule factor Xa inhibitor (rivaroxaban, Bay 59-7939) was tested in a human plasma clotting assay. As reported by Perzborn et al, *J. Thromb. Haemost.* 3:514-521, 2005; prothrombin time measurements are an accurate method for evaluating the anticoagulant effect of rivaroxaban. The effect of 1 µM rivaroxaban on prothrombin time (PT) prolongation of pooled human plasma and the reversal of inhibitory effect was measured by a MLA Electra 800 Automatic coagulation timer. 100 µL pooled citrate anticoagulated human plasma was mixed with rivaroxaban and different concentrations of antidote. Prior to measurement of clotting time, rabbit brain Thromboplastin C Plus reagent (Dade Behring) was added to plasma samples per manufacturer's instructions. Addition of 1.9 µM recombinant antidote produced a 100% correction of anticoagulation produced by 1 µM rivaroxaban.

Example 13

In Vitro Reversal of Apixaban by r-Antidote

In Table F, the effect of recombinant antidote protein on reversal of anticoagulation by apixaban was tested in a human plasma clotting assay. As reported by Pinto et al., *J. Med. Chem.* 55(22):5339-5356, 2007; prothrombin time (PT) measurements are an accurate method of evaluating the ex vivo anticoagulant effects of apixaban. The effect of 1 µM and 1.5 µM apixaban on prothrombin time (PT) prolongation of pooled human plasma and the reversal of inhibitory effect was measured by a MLA Electra 800 Automatic coagulation timer. 100 µL pooled citrate anticoagulated human plasma was mixed with apixaban and different concentrations of antidote. Prior to measurement of clotting time, rabbit brain Thromboplastin C Plus reagent (Dade Behring) was added to plasma samples per manufacturer's instructions. Addition of 1.9 µM recombinant antidote produced a 97% correction of anticoagulation produced by 1.5 µM apixaban.

TABLE F r-Antidote reversal of anticoagulant activity of Apixaban

| | PT (sec) | Fold Change |
|---|---|---|
| Control human plasma | 14.1 | — |
| 1 µM apixaban | 16.4 | 1.16 |
| 1 µM apixaban + 380 nM rAntidote | 15.3 | 1.09 |
| 1 µM apixaban + 760 nM rAntidote | 14.9 | 1.06 |
| 1 µM apixaban + 1.14 µM rAntidote | 14.2 | 1.01 |
| 1 µM apixaban + 1.52 µM rAntidote | 14.2 | 1.01 |
| 1.5 µM apixaban | 18.4 | 1.31 |
| 1.5 µM apixaban + 1.52 µM rAntidote | 14.6 | 1.04 |
| 1.5 µM apixaban + 1.90 µM rAntidote | 14.3 | 1.01 |

TABLE F-continued r-Antidote reversal of anticoagulant activity of Apixaban

|  | PT (sec) | Fold Change |
|---|---|---|
| 1.52 μM rAntidote | 14 | — |
| 1.90 μM rAntidote | 14.2 | — |

Example 14

In Vitro Inhibition of Argatroban by Des-Gla Anhydro-fXa

To measure the inhibition of thrombin activity by argatroban and reversal of its inhibitory effect, purified human thrombin (5 nM), argatroban (50 nM) and different concentrations of antidote des-Gla anhydro fXa were added to a buffer containing 20 mM Tris, 0.15 M NaCl, 5 mM Calcium chloride, 0.1% bovine serum albumin, pH 7.4. After incubation at room temperature for 20 min, an amidolytic substrate 52288 (200 uM) was added to the mixture and the rate of p-nitroanilide substrate cleavage was monitored by absorbance at 405 nm. The results are presented in FIG. 12.

Example 15

Methods for Extending Plasma Half Life of Circulation of Antidote Upon Human Dosing Recent pharmacokinetic data in animals have shown that recombinant antidote expressed in CHO DuxB11 cells have a plasma half life of clearance ($T_{1/2}$) of 19 minutes in SD rats and 30 minutes in rhesus monkeys. A longer half life of clearance may be desirable for human use. Extension of $T_{1/2}$ in humans may require modification of the protein by a conjugated moiety capable of extending circulating half life of the fXa derivative. The conjugated moiety such as an antibody may include whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein. The antibodies can be polyclonal or monoclonal and can be isolated from any suitable biological source, e.g., murine, rat, sheep and canine A conjugated moiety may also be selected from a group consisting of polyethylene glycol, an acyl group, a liposome, an encapsulating agent, a carrier protein, an artificial phospholipid membrane, a nanoparticle, and combinations thereof.

Pharmacokinetics of Antidote in Rat

Figure 23:
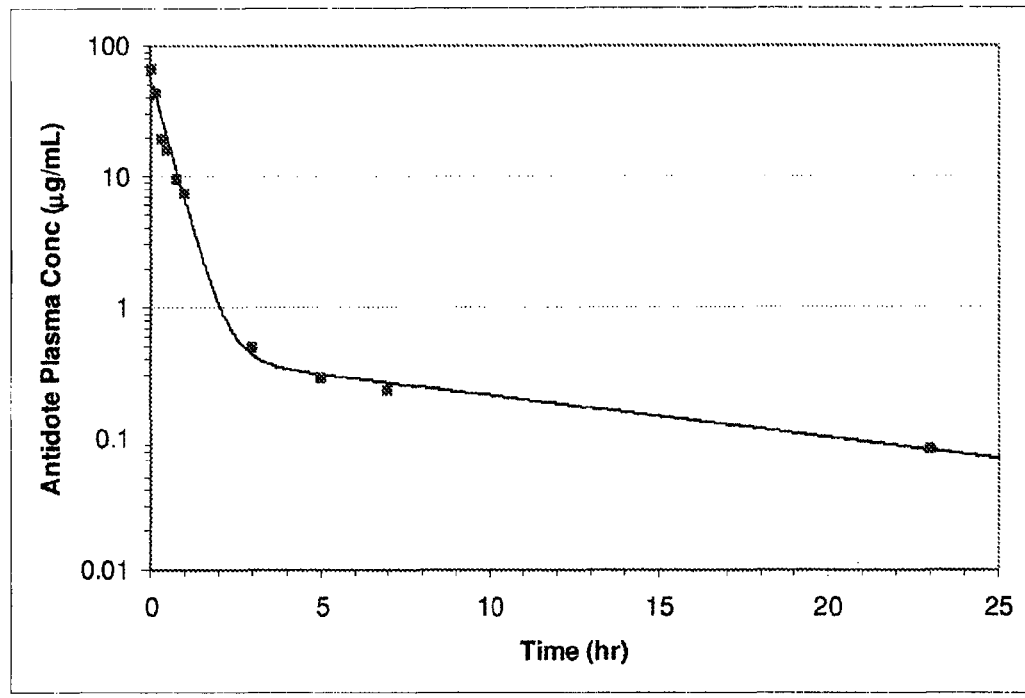
FIG. 23 shows the plasma concentration-time profile of the r-Antidote in Sprague-Dawley rats based on the data collected in Example 15.

One milligram of antidote was administered as a short intravenous infusion over five minutes to four Sprague-Dawley rats. Serial plasma samples were collected and analyzed for antidote concentration using an enzyme-linked immunosorbent assay (ELISA). Plasma concentration-time profiles of the antidote can be described by a two compartment model. Systemic clearance of the antidote was low (1.65 mL/min/kg) and volume of distribution was small (0.27 L/kg). The distribution half-life was 19 minutes followed by a much longer terminal half-life of 10 hours. Because of the need to immediately maintain antidote plasma concentration above that of a factor Xa inhibitor (the anticoagulant), the distribution half-life is expected to have a much bigger impact than the terminal half-life on the dose selection during an overdose treatment. The data is presented in FIG. 23.

Pharmacokinetics of Antidote in Rhesus Monkey

Figure 24:
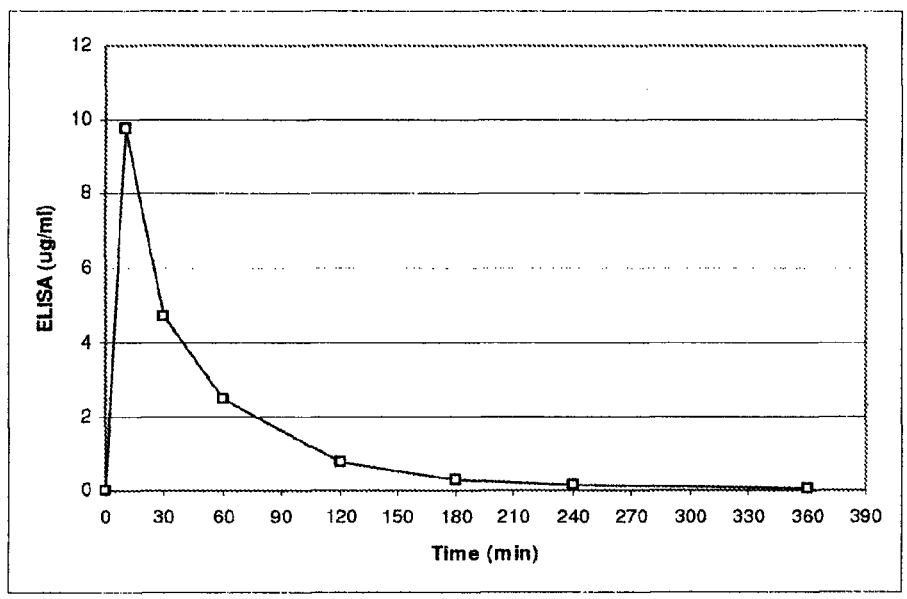
FIG. 24 shows the plasma concentration-time profile of the r-Antidote in rhesus monkeys based on the data collected in Example 15.

Two animals were each dosed with 10 mg antidote by intravenous dosing over a ten minute period. Plasma samples for determination of $T_{1/2}$ were carried out in a manner similar to that in the rat study. Plasma half life of clearance ($T_{1/2}$) was approximately 30 minutes. The data is presented in FIG. 24.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

TABLE 1

Sequence ID NO. 1—Polypeptide Sequence of Human Factor X

```
  1 MGRPLHLVLL  SASLAGLLLL  GESLFIRREQ  ANNILARVTR  ANSFLEEMKK  GHLERECMEE

61 TCSYEEAREV  FEDSDKTNEF  WNKYKDGDQC  ETSPCQNQGK  CKDGLGEYTC  TCLEGFEGKN

121 CELFTRKLCS  LDNGDCDQFC  HEEQNSVVCS  CARGYTLADN  GKACIPTGPY  PCGKQTLERR

181 KRSVAQATSS  SGEAPDSITW  KPYDAADLDP  TENPFDLLDF  NQTQPERGDN  NLTRIVGGQE

241 CKDGECPWQA  LLINEENEGF  CGGTILSEFY  ILTAAHCLYQ  AKRFKVRVGD  RNTEQEEGGE

301 AVHEVEVVIK  HNRFTKETYD  FDIAVLRLKT  PITFRMNVAP  ACLPERDWAE  STLMTQKTGI

361 VSGFGRTHEK  GRQSTRLKML  EVPYVDRNSC  KLSSSFIITQ  NMFCAGYDTK  QEDACQGDSG

421 GPHVTRFKDT  YFVTGIVSWG  EGCARKGKYG  IYTKVTAFLK  WIDRSMKTRG  LPKAKSHAPE

481 VITSSPLK
```

TABLE 2

| Sequence ID NO. 2—A polynucleotide Sequence Encoding Factor X |
|---|
| 1 gactttgctc cagcagcctg tcccagtgag gacagggaca cagtactcgg ccacaccatg |
| 61 gggcgcccac tgcacctcgt cctgctcagt gcctccctgg ctggcctcct gctgctcggg |
| 121 gaaagtctgt tcatccgcag ggagcaggcc aacaacatcc tggcgagggt cacgagggcc |
| 181 aattcctttc ttgaagagat gaagaaagga caccctcgaaa gagagtgcat ggaagagacc |
| 241 tgctcatacg aagaggcccg cgaggtcttt gaggacagcg acaagacgaa tgaattctgg |
| 301 aataaataca agatggcga ccagtgtgag accagtcctt gccagaacca gggcaaatgt |
| 361 aaagacggcc tcggggaata cacctgcacc tgtttagaag gattcgaagg caaaaactgt |
| 421 gaattattca cacggaagct ctgcagcctg gacaacgggg actgtgacca gttctgccac |
| 481 gaggaacaga actctgtggt gtgctcctgc gcccgcgggt acaccctggc tgacaacggc |
| 541 aaggcctgca ttcccacagg gccctacccc tgtgggaaac agaccctgga acgcaggaag |
| 601 aggtcagtgg cccaggccac cagcagcagc ggggaggccc ctgacagcat cacatggaag |
| 661 ccatatgatg cagccgacct ggaccccacc gagaacccct tcgacctgct tgacttcaac |
| 721 cagacgcagc ctgagagggg cgacaacaac ctcaccagga tcgtggggag ccaggaatgc |
| 781 aaggacgggg agtgtccctg gcaggccctg ctcatcaatg aggaaaacga gggtttctgt |
| 841 ggtggaacca ttctgagcga gttctacatc ctaacggcag cccactgtct ctaccaagcc |
| 901 aagagattca aggtgagggt aggggaccgg aacacggagc aggaggaggg cggtgaggcg |
| 961 gtgcacgagg tggaggtggt catcaagcac aaccggttca caaaggagac ctatgacttc |
| 1021 gacatcgccg tgctccggct caagacccc atcaccttcc gcatgaacgt ggcgcctgcc |
| 1081 tgcctccccg agcgtgactg ggccgagtcc acgctgatga cgcagaagac ggggattgtg |
| 1141 agcggcttcg gcgcaccca cgagaaggc cggcagtcca ccaggctcaa gatgctggag |
| 1201 gtgccctacg tggaccgcaa cagctgcaag ctgtccagca gcttcatcat cacccagaac |
| 1261 atgttctgtg ccggctacga caccaagcag gaggatgcct gccaggggga cagcgggggc |
| 1321 ccgcacgtca cccgcttcaa ggacacctac ttcgtgacag catcgtcag ctggggagag |
| 1381 ggctgtgccc gtaaggggaa gtacgggatc tacaccaagg tcaccgcctt cctcaagtgg |
| 1441 atcgacaggt ccatgaaaac caggggcttg cccaaggcca agagccatgc cccggaggtc |
| 1501 ataacgtcct ctccattaaa gtgagatccc actcaaaaaa aaaaaaaaa aaaaaaaaa |

TABLE 3

| Sequence ID NO. 3—Polypeptide Sequence of Mature Human Factor X |
|---|
| 1ANSFLEEMKK GHLERECMEE TCSYEEAREV FEDSDKTNEF WNKYKDGDQC ETSPCQNQGK |
| 61CKDGLGEYTC TCLEGFEGKN CELFTRKLCS LDNGDCDQFC HEEQNSVVCS CARGYTLADN |
| 121GKACIPTGPY PCGKQTLERR KRSVAQATSS SGEAPDSITW KPYDAADLDP TENPFDLLDF |
| 181NQTQPERGDN NLTRIVGGQE CKDGECPWQA LLINEENEGF CGGTILSEFY ILTAAHCLYQ |
| 241AKRFKVRVGD RNTEQEEGGE AVHEVEVVIK HNRFTKETYD FDIAVLRLKT PITFRMNVAP |
| 301ACLPERDWAE STLMTQKTGI VSGFGRTHEK GRQSTRLKML EVPYVDRNSC KLSSSFIITQ |
| 361NMFCAGYDTK QEDACQGDSG GPHVTRFKDT YFVTGIVSWG EGCARKGKYG IYTKVTAFLK |
| 421WIDRSMKTRG LPKAKSHAPE VITSSPLK |

TABLE 4

Sequence ID NO. 4—Polypeptide Sequence of the Gla-domainless Factor
Xa lacking 1 to 44 amino acid residues Light Chain
```
  1                                           KDGDQC ETSPCQNQGK
 61   CKDGLGEYTC TCLEGFEGKN CELFTRKLCS LDNGDCDQFC HEEQNSVVCS CARGYTLADN
121   GKACIPTGPY PCGKQTLER
```

Heavy Chain
```
181               IVGGQE CKDGECPWQA LLINEENEGF CGGTILSEFY ILTAAHCLYQ
241   AKRFKVRVGD RNTEQEEGGE AVHEVEVVIK HNRFTKETYD FDIAVLRLKT PITFRMNVAP
301   ACLPERDWAE STLMTQKTGI VSGFGRTHEK GRQSTRLKML EVPYVDRNSC KLSSSFIITQ
361   NMFCAGYDTK QEDACQGDSG GPHVTRFKDT YFVTGIVSWG EGCARKGKYG IYTKVTAFLK
421   WIDRSMKTRG LPKAKSHAPE VITSSPLK
```

TABLE 5

Sequence ID NO. 5—Polypeptide Sequence of the Gla-domainless Factor Xa
lacking 1 to 45 amino acid residues Light Chain
```
  1                                            DGDQC ETSPCQNQGK
 61   CKDGLGEYTC TCLEGFEGKN CELFTRKLCS LDNGDCDQFC HEEQNSVVCS CARGYTLADN
121   GKACIPTGPY PCGKQTLER
```

Heavy Chain
```
181               IVGGQE CKDGECPWQA LLINEENEGF CGGTILSEFY ILTAAHCLYQ
241   AKRFKVRVGD RNTEQEEGGE AVHEVEVVIK HNRFTKETYD FDIAVLRLKT PITFRMNVAP
301   ACLPERDWAE STLMTQKTGI VSGFGRTHEK GRQSTRLKML EVPYVDRNSC KLSSSFIITQ
361   NMFCAGYDTK QEDACQGDSG GPHVTRFKDT YFVTGIVSWG EGCARKGKYG IYTKVTAFLK
421   WIDRSMKTRG LPKAKSHAPE VITSSPLK
```

TABLE 6

Sequence ID NO. 6—Polypeptide Sequence of Activated Human Factor Xa
prior to Post-Translation of Glutamic Acid to γ-Carboxyglutamic acid Light Chain
```
  1   ANSFLEEMKK GHLERECMEE TCSYEEAREV FEDSDKTNEF WNKYKDGDQC ETSPCQNQGK
 61   CKDGLGEYTC TCLEGFEGKN CELFTRKLCS LDNGDCDQFC HEEQNSVVCS CARGYTLADN
121   GKACIPTGPY PCGKQTLER
```

Heavy Chain
```
181               IVGGQE CKDGECPWQA LLINEENEGF CGGTILSEFY ILTAAHCLYQ
241   AKRFKVRVGD RNTEQEEGGE AVHEVEVVIK HNRFTKETYD FDIAVLRLKT PITFRMNVAP
301   ACLPERDWAE STLMTQKTGI VSGFGRTHEK GRQSTRLKML EVPYVDRNSC KLSSSFIITQ
361   NMFCAGYDTK QEDACQGDSG GPHVTRFKDT YFVTGIVSWG EGCARKGKYG IYTKVTAFLK
421   WIDRSMKTRG LPKAKSHAPE VITSSPLK
```

TABLE 7

Sequence ID NO. 7—Polypeptide Sequence of Activated Human Factor
Xa with Post-Translation of Glutamic Acid to γ-Carboxyglutamic acid
(γ represents γ-Carboxyglutamic Acid Residue)

Light Chain
```
  1   ANSFLγγMKK GHLγRγCMγγ TCSYγγARγV FγDSDKTNγF WNKYKDGDQC ETSPCQNQGK

61   CKDGLGEYTC TCLEGFEGKN CELFTRKLCS LDNGDCDQFC HEEQNSVVCS CARGYTLADN

121   GKACIPTGPY PCGKQTLER
```

Heavy Chain
```
181               IVGGQE CKDGECPWQA LLINEENEGF CGGTILSEFY ILTAAHCLYQ

241   AKRFKVRVGD RNTEQEEGGE AVHEVEVVIK HNRFTKETYD FDIAVLRLKT PITFRMNVAP

301   ACLPERDWAE STLMTQKTGI VSGFGRTHEK GRQSTRLKML EVPYVDRNSC KLSSSFIITQ

421   WIDRSMKTRG LPKAKSHAPE VITSSPLK
```

TABLE 8

Sequence ID NO. 8—Polypeptide Sequence of Activated Human Factor
Xa-Light Chain with Post-Translation of Glutamic Acid to γ-
Carboxyglutamic acid Light Chain
```
  1   ANSFLγγMKK GHLγRγCMγγ TCSYγγARγV FγDSDKTNγF WNKYKDGDQC ETSPCQNQGK

61   CKDGLGEYTC TCLEGFEGKN CELFTRKLCS LDNGDCDQFC HEEQNSVVCS CARGYTLADN

121   GKACIPTGPY PCGKQTLER
```

TABLE 9

Sequence ID NO. 9—Polypeptide Sequence of Activated Human Factor
Xa-Heavy Chain

```
181              IVGGQE CKDGECPWQA LLINEENEGF CGGTILSEFY ILTAAHCLYQ

241  AKRFKVRVGD RNTEQEEGGE AVHEVEVVIK HNRFTKETYD FDIAVLRLKT PITFRMNVAP

301  ACLPERDWAE STLMTQKTGI VSGFGRTHEK GRQSTRLKML EVPYVDRNSC KLSSSFIITQ

361  NMFCAGYDTK QEDACQGDSG GPHVTRFKDT YFVTGIVSWG EGCARKGKYG IYTKVTAFLK

421  WIDRSMKTRG LPKAKSHAPE VITSSPLK
```

TABLE 10

Sequence ID NO. 10—Polypeptide Sequence of the Des-Gla Anhydro
Factor Xa (Ã represents dehydroalanine)

Light Chain
```
  1                                          KDGDQC ETSPCQNQGK

61   CKDGLGEYTC TCLEGFEGKN CELFTRKLCS LDNGDCDQFC HEEQNSVVCS CARGYTLADN

121   GKACIPTGPY PCGKQTLER
```

Heavy Chain
```
181               IVGGQE CKDGECPWQA LLINEENEGF CGGTILSEFY ILTAAHCLYQ

241   AKRFKVRVGD RNTEQEEGGE AVHEVEVVIK HNRFTKETYD FDIAVLRLKT PITFRMNVAP

301   ACLPERDWAE STLMTQKTGI VSGFGRTHEK GRQSTRLKML EVPYVDRNSC KLSSSFIITQ

361   NMFCAGYDTK QEDACQGDÃG GPHVTRFKDT YFVTGIVSWG EGCARKGKYG IYTKVTAFLK

421   WIDRSMKTRG LPKAKSHAPE VITSSPLK
```

TABLE 11

Sequence ID NO. 11—Polypeptide Sequence of the Des-Gla fXa-S379A

Light Chain
```
  1                                             DGDQC ETSPCQNQGK
 61  CKDGLGEYTC TCLEGFEGKN CELFTRKLCS LDNGDCDQFC HEEQNSVVCS CARGYTLADN
121  GKACIPTGPY PCGKQTLER
```

Heavy Chain
```
181              IVGGQE CKDGECPWQA LLINEENEGF CGGTILSEFY ILTAAHCLYQ
241  AKRFKVRVGD RNTEQEEGGE AVHEVEVVIK HNRFTKETYD FDIAVLRLKT PITFRMNVAP
301  ACLPERDWAE STLMTQKTGI VSGFGRTHEK GRQSTRLKML EVPYVDRNSC KLSSSFIITQ
361  NMFCAGYDTK QEDACQGDAG GPHVTRFKDT YFVTGIVSWG EGCARKGKYG IYTKVTAFLK
421  WIDRSMKTRG LPKAKSHAPE VITSSPLK
```

TABLE 12

Sequence ID NO. 12—Polypeptide Sequence of a Human Factor Xa triple mutant prior to removal of the -RKRRKR-linker (SEQ ID NO: 41)

Light Chain
```
  1  ANSFL                            F WNKYKDGDQC ETSPCQNQGK
 61  CKDGLGEYTC TCLEGFEGKN CELFTRKLCS LDNGDCDQFC HEEQNSVVCS CARGYTLADN
121  GKACIPTGPY PCGKQTLER
```

Linker
```
     RKRRKR
```

Heavy Chain
```
181              IVGGQE CKDGECPWQA LLINEENEGF CGGTILSEFY ILTAAHCLYQ
241  AKRFKVRVGD RNTEQEEGGE AVHEVEVVIK HNRFTKETYD FDIAVLRLKT PITFRMNVAP
301  ACLPERDWAE STLMTQKTGI VSGFGRTHEK GRQSTRLKML EVPYVDRNSC KLSSSFIITQ
361  NMFCAGYDTK QEDACQGDAG GPHVTRFKDT YFVTGIVSWG EGCARKGKYG IYTKVTAFLK
421  WIDRSMKTRG LPKAKSHAPE VITSSPLK
```

TABLE 13

Sequence ID NO. 13—Polypeptide Sequence of a Human Factor Xa triple mutant after removal of the -RKRRKR-linker (SEQ ID NO: 41)

Light Chain
```
  1  ANSFL                            F WNKYKDGDQC ETSPCQNQGK
 61  CKDGLGEYTC TCLEGFEGKN CELFTRKLCS LDNGDCDQFC HEEQNSVVCS CARGYTLADN
121  GKACIPTGPY PCGKQTLER
```

Heavy Chain
```
181              IVGGQE CKDGECPWQA LLINEENEGF CGGTILSEFY ILTAAHCLYQ
241  AKRFKVRVGD RNTEQEEGGE AVHEVEVVIK HNRFTKETYD FDIAVLRLKT PITFRMNVAP
301  ACLPERDWAE STLMTQKTGI VSGFGRTHEK GRQSTRLKML EVPYVDRNSC KLSSSFIITQ
361  NMFCAGYDTK QEDACQGDAG GPHVTRFKDT YFVTGIVSWG EGCARKGKYG IYTKVTAFLK
421  WIDRSMKTRG LPKAKSHAPE VITSSPLK
```

TABLE 14

Sequence ID NO. 14—Polypeptide Sequence of Light Chain Fragment of Human Factor Xa triple mutant after secretion

```
  1 ANSFL                    F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

TABLE 15

Sequence ID NO. 15—Polypeptide Sequence of Heavy Chain Fragment of Human Factor Xa triple mutant after secretion

```
Heavy Chain
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

TABLE 16

Sequence ID NO. 16—A polynucleotide Sequence Encoding r-Antidote (a Factor X triple mutant)

```
   1 ATGGGGCGCC CACTGCACCT CGTCCTGCTC AGTGCCTCCC TGGCTGGCCT CCTGCTGCTC GGGGAAAGTC TGTTCATCCG CAGGGAGCAG
     GCCAACAACA
 101 TCCTGGCGAG GGTCACGAGG GCCAATTCCT TTCTTTTCTG GAATAAATAC AAAGATGGCG ACCAGTGTGA GACCAGTCCT TGCCAGAACC
     AGGGCAAATG
 201 TAAAGACGGC CTCGGGGAAT ACACCTGCAC CTGTTTAGAA GGATTCGAAG GCAAAAACTG TGAATTATTC ACACGGAAGC TCTGCAGCCT
     GGACAACGGG
 301 GACTGTGACC AGTTCTGCCA CGAGGAACAG AACTCTGTGG TGTGCTCCTG CGCCCGCGGG TACACCCTGG CTGACAACGG CAAGGCCTGC
     ATTCCCACAG
 401 GGCCCTACCC CTGTGGGAAA CAGACCCTGG AACGCAGGAA GAGGAGGAAG AGGATCGTGG GAGGCCAGGA ATGCAAGGAC GGGGAGTGTC
     CCTGGCAGGC
 501 CCTGCTCATC AATGAGGAAA ACGAGGGTTT CTGTGGTGGA ACCATTCTGA GCGAGTTCTA CATCCTAACG GCAGCCCACT GTCTCTACCA
     AGCCAAGAGA
 601 TTCAAGGTGA GGGTAGGGGA CCGGAACACG GAGCAGGAGG AGGGCGGTGA GGCGGTGCAC GAGGTGGAGG TGGTCATCAA GCACAACCGG
     TTCACAAAGG
 701 AGACCTATGA CTTCGACATC GCCGTGCTCC GGCTCAAGAC CCCCATCACC TTCCGCATGA ACGTGGCGCC TGCCTGCCTC CCCGAGCGTG
     ACTGGGCCGA
 801 GTCCACGCTG ATGACGCAGA AGACGGGGAT TGTGAGCGGC TTCGGGCGCA CCCACGAGAA GGGCCGGCAG TCCACCAGGC
     TCAAGATGCT GGAGGTGCCC
 901 TACGTGGACC GCAACAGCTG CAAGCTGTCC AGCAGCTTCA TCATCACCCA GAACATGTTC TGTGCCGGCT ACGACACCAA
     GCAGGAGGAT GCCTGCCAGG
1001 GGGACGCAGG GGGCCCGCAC GTCACCCGCT TCAAGGACAC CTACTTCGTG ACAGGCATCG TCAGCTGGGG AGAGGGCTGT GCCCGTAAGG
     GGAAGTACGG
1101 GATCTACACC AAGGTCACCG CCTTCCTCAA GTGGATCGAC AGGTCCATGA AAACCAGGGG CTTGCCCAAG GCCAAGAGCC ATGCCCCGGA
     GGTCATAACG
1201 TCCTCTCCAT TAAAGTGA
```

TABLE 17

| Sequence ID. NO. 17—Polynucleotide Sequence of the r-Antidote Expression Vector |
|---|

```
   1 TCTAGACACA GTACTCGGCC ACACCATGGG GCGCCCACTG CACCTCGTCC TGCTCAGTGC CTCCCTGGCT GGCCTC-
     CTGC
     TGCTCGGGGA AAGTCTGTTC

101 ATCCGCAGGG AGCAGGCCAA CAACATCCTG GCGAGGGTCA CGAGGGCCAA TTCCTTTCTT TTCTGGAATA AATA-
     CAAAGA
     TGGCGACCAG TGTGAGACCA

201 GTCCTTGCCA GAACCAGGGC AAATGTAAAG ACGGCCTCGG GGAATACACC TGCACCT-
     GTT TAGAAGGATT CGAAGGCAAA
     AACTGTGAAT TATTCACACG

301 GAAGCTCTGC AGCCTGGACA ACGGGGACTG TGACCAGTTC TGCCACGAGG AACAGAACTC TGTGGTGTGC TCCT-
     GCGCCC
     GCGGGTACAC CCTGGCTGAC

401 AACGGCAAGG CCTGCATTCC CACAGGGCCC TACCCCTGTG GAAACAGAC CCTGGAACGC AGGAAGAGGA GGAAGAG-
     GAT
     CGTGGGAGGC CAGGAATGCA

501 AGGACGGGGA GTGTCCCTGG CAGGCCCTGC TCATCAATGA GGAAAACGAG GGTTTCTGTG GTGGAACCAT TCTGAGC-
     GAG
     TTCTACATCC TAACGGCAGC

601 CCACTGTCTC TACCAAGCCA AGAGATTCAA GGTGAGGGTA GGGGACCGGA ACACGGAGCA GGAGGAGGGC GGTGAG-
     GCGG
     TGCACGAGGT GGAGGTGGTC

701 ATCAAGCACA ACCGGTTCAC AAAGGAGACC TATGACTTCG ACATCGCCGT GCTCCGGCTC AAGACCCCCA TCACCT-
     TCCG
     CATGAACGTG GCGCCTGCCT

801 GCCTCCCCGA GCGTGACTGG GCCGAGTCCA CGCTGATGAC GCAGAAGACG GGGATTGTGA GCGGCTTCGG GCGCAC-
     CCAC
     GAGAAGGGCC GGCAGTCCAC

901 CAGGCTCAAG ATGCTGGAGG TGCCCTACGT GGACCGCAAC AGCTGCAAGC TGTCCAGCAG CTTCATCATC ACCCA-
     GAACA
     TGTTCTGTGC CGGCTACGAC

1001 ACCAAGCAGG AGGATGCCTG CCAGGGGGAC GCAGGGGGCC CGCACGTCAC CCGCTTCAAG GACACCTACT TCGT-
     GACAGG
     CATCGTCAGC TGGGGAGAGG

1101 GCTGTGCCCG TAAGGGGAAG TACGGGATCT ACACCAAGGT CACCGCCTTC CTCAAGTGGA TCGACAGGTC CAT-
     GAAAACC
     AGGGGCTTGC CCAAGGCCAA

1201 GAGCCATGCC CCGGAGGTCA TAACGTCCTC TCCATTAAAG TGAGATCCCA CTCGGATCCC TATTCTATAG TGTCAC-
     CTAA
     ATGCTAGAGC TCGCTGATCA

1301 GCCTCGACTG TGCCTTCTAG TTGCCAGCCA TCTGTTGTTT GCCCCTCCCC CGTGCCTTCC TTGACCCTGG AAGGTGC-
     CAC
     TCCCACTGTC CTTTCCTAAT

1401 AAAATGAGGA AATTGCATCG CATTGTCTGA GTAGGTGTCA TTCTATTCTG GGGGGTGGGG TGGGGCAGGA CAG-
     CAAGGGG
     GAGGATTGGG AAGACAATAG

1501 CAGGCATGCT GGGGATGCGG TGGGCTCTAT GGCTTCTGAG GCGGAAAGAA CCAGCTGGGG CTCGAGCGGC CGCCCCT-
     TCT
     GAGGCGGAAA GAACCAGCTG

1601 TGGAATGTGT GTCAGTTAGG GTGTGGAAAG TCCCCAGGCT CCCCAGCAGG CAGAAGTATG CAAAGCATGC ATCT-
     CAATTA
     GTCAGCAACC AGGTGTGGAA

1701 AGTCCCCAGG CTCCCCAGCA GGCAGAAGTA TGCAAAGCAT GCATCTCAAT TAGTCAG-
     CAA CCATAGTCCC GCCCCTAACT
     CCGCCCATCC CGCCCCTAAC

1801 TCCGCCCAGT TCCGCCCATT CTCCGCCCCA TGGCTGACTA ATTTTTTTA TTTATGCAGA GGCCGAGGCC GCCTCG-
     GCCT
     CTGAGCTATT CCAGAAGTAG

1901 TGAGGAGGCT TTTTTGGAGG CCTAGGCTTT TGCAAAAAAG CTAGCTTCCC GCTGCCATCA TGGTTCGACC ATT-
     GAACTGC
     ATCGTCGCCG TGTCCCAAAA
```

TABLE 17-continued

Sequence ID. NO. 17—Polynucleotide Sequence of the r-Antidote Expression Vector

```
2001 TATGGGGATT GGCAAGAACG GAGACCTACC CTGGCCTCCG CTCAGGAACG AGTTCAAGTA CTTCCAAAGA ATGACCA-
     CAA
     CCTCTTCAGT GGAAGGTAAA

2101 CAGAATCTGG TGATTATGGG TAGGAAAACC TGGTTCTCCA TTCCTGAGAA GAATCGACCT TTAAAGGACA GAAT-
     TAATAT
     AGTTCTCAGT AGAGAACTCA

2201 AAGAACCACC ACGAGGAGCT CATTTTCTTG CCAAAAGTTT GGATGATGCC TTAAGACTTA TTGAACAACC GGAATTG-
     GCA
     AGTAAAGTAG ACATGGTTTG

2301 GATAGTCGGA GGCAGTTCTG TTTACCAGGA AGCCATGAAT CAACCAGGCC ACCTTAGACT CTTTGTGACA AGGAT-
     CATGC
     AGGAATTTGA AAGTGACACG

2401 TTTTTCCCAG AAATTGATTT GGGGAAATAT AAACTTCTCC CAGAATACCC AGGCGTCCTC TCTGAGGTCC AGGAG-
     GAAAA
     AGGCATCAAG TATAAGTTTG

2501 AAGTCTACGA GAAGAAAGAC TAACAGGAAG ATGCTTTCAA GTTCTCTGCT CCCCTCCTAA AGCTATGCAT TTT-
     TATAAGA
     CCATGGGACT TTTGCTGGCT

2601 TTAGATCCCG CGGAGATCCA GACATGATAA GATACATTGA TGAGTTTGGA CAAACCACAA CTAGAAT-
     GCA GTGAAAAAAA
     TGCTTTATTT GTGAAATTTG

2701 TGATGCTATT GCTTTATTTG TAACCATTAT AAGCTGCAAT AAACAAGTTA ACAACAACAA TTGCATTCAT TTTAT-
     GTTTC
     AGGTTCAGGG GGAGGTGTGG

2801 GAGGTTTTTT AAAGCAAGTA AAACCTCTAC AAATGTGGTA TGGCTGATTA TGAGCTCCAG CTTTTGTTCC CTTTAGT-
     GAG
     GGTTAATTGC GCGCTTGGCG

2901 TAATCATGGT CATAGCTGTT TCCTGTGTGA AATTGTTATC CGCTCACAAT TCCACACAAC ATAC-
     GAGCCG GAAGCATAAA
     GTGTAAAGCC TGGGGTGCCT

3001 AATGAGTGAG CTAACTCACA TTAATTGCGT TGCGCTCACT GCCCGCTTTC CAGTCGGGAA ACCTGTCGTG CCAGCTG-
     CAT
     TAATGAATCG GCCAACGCGC

3101 GGGGAGAGGC GGTTTGCGTA TTGGGCGCTC TTCCGCTTCC TCGCTCACTG ACTCGCTGCG CTCGGTCGTT CGGCT-
     GCGGC
     GAGCGGTATC AGCTCACTCA

3201 AAGGCGGTAA TACGGTTATC CACAGAATCA GGGGATAACG CAGGAAAGAA CATGTGAGCA AAAGGCCAGC AAAAGGC-
     CAG
     GAACCGTAAA AAGGCCGCGT

3301 TGCTGGCGTT TTTCCATAGG CTCCGCCCCC CTGACGAGCA TCACAAAAAT CGACGCTCAA GTCAGAGGTG GCGAAAC-
     CCG
     ACAGGACTAT AAAGATACCA

3401 GGCGTTTCCC CCTGGAAGCT CCCTCGTGCG CTCTCCTGTT CCGACCCTGC CGCTTACCGG ATACCT-
     GTCC GCCTTTCTCC
     CTTCGGGAAG CGTGGCGCTT

3501 TCTCATAGCT CACGCTGTAG GTATCTCAGT TCGGTGTAGG TCGTTCGCTC CAAGCTGGGC TGTGTGCACG AAC-
     CCCCCGT
     TCAGCCCGAC CGCTGCGCCT

3601 TATCCGGTAA CTATCGTCTT GAGTCCAACC CGGTAAGACA CGACTTATCG CCACTGGCAG CAGCCACTGG TAACAG-
     GATT
     AGCAGAGCGA GGTATGTAGG

3701 CGGTGCTACA GAGTTCTTGA AGTGGTGGCC TAACTACGGC TACACTAGAA GGACAGTATT TGGTATCTGC GCTCT-
     GCTGA
     AGCCAGTTAC CTTCGGAAAA

3801 AGAGTTGGTA GCTCTTGATC CGGCAAACAA ACCACCGCTG GTAGCGGTGG TTTTTTTGTT TGCAAGCAGC AGAT-
     TACGCG
     CAGAAAAAAA GGATCTCAAG

3901 AAGATCCTTT GATCTTTTCT ACGGGGTCTG ACGCTCAGTG GAACGAAAAC TCACGTTAAG GGATTTTGGT CAT-
     GAGATTA
     TCAAAAAGGA TCTTCACCTA
```

TABLE 17-continued

Sequence ID. NO. 17—Polynucleotide Sequence of the r-Antidote Expression Vector

```
4001 GATCCTTTTA AATTAAAAAT GAAGTTTTAA ATCAATCTAA AGTATATATG AGTAAACTTG GTCTGACAGT TACCAAT-
     GCT
     TAATCAGTGA GGCACCTATC

4101 TCAGCGATCT GTCTATTTCG TTCATCCATA GTTGCCTGAC TCCCCGTCGT GTAGATAACT ACGATACGGG AGGGCT-
     TACC
     ATCTGGCCCC AGTGCTGCAA

4201 TGATACCGCG AGACCCACGC TCACCGGCTC CAGATTTATC AGCAATAAAC CAGCCAGCCG GAAGGGCCGA GCGCA-
     GAAGT
     GGTCCTGCAA CTTTATCCGC

4301 CTCCATCCAG TCTATTAATT GTTGCCGGGA AGCTAGAGTA AGTAGTTCGC CAGTTAATAG TTTGCGCAAC GTTGTT-
     GCCA
     TTGCTACAGG CATCGTGGTG

4401 TCACGCTCGT CGTTTGGTAT GGCTTCATTC AGCTCCGGTT CCCAACGATC AAGGCGAGTT ACATGATCCC CCATGTT-
     GTG
     CAAAAAAGCG GTTAGCTCCT

4501 TCGGTCCTCC GATCGTTGTC AGAAGTAAGT TGGCCGCAGT GTTATCACTC ATGGTTATGG CAGCACTGCA TAAT-
     TCTCTT
     ACTGTCATGC CATCCGTAAG

4601 ATGCTTTTCT GTGACTGGTG AGTACTCAAC CAAGTCATTC TGAGAATAGT GTATGCGGCG ACCGAGTTGC TCTTGC-
     CCGG
     CGTCAATACG GGATAATACC

4701 GCGCCACATA GCAGAACTTT AAAAGTGCTC ATCATTGGAA AACGTTCTTC GGGGCGAAAA CTCTCAAGGA TCTTAC-
     CGCT
     GTTGAGATCC AGTTCGATGT

4801 AACCCACTCG TGCACCCAAC TGATCTTCAG CATCTTTTAC TTTCACCAGC GTTTCTGGGT GAG-
     CAAAAAC AGGAAGGCAA
     AATGCCGCAA AAAAGGGAAT

4901 AAGGGCGACA CGGAAATGTT GAATACTCAT ACTCTTCCTT TTTCAATATT ATTGAAGCAT TTATCAGGGT TATT-
     GTCTCA
     TGAGCGGATA CATATTTGAA

5001 TGTATTTAGA AAAATAAACA AATAGGGGTT CCGCGCACAT TTCCCCGAAA AGTGCCACCT GGGAAATTGT AAACGT-
     TAAT
     ATTTTGTTAA AATTCGCGTT

5101 AAATTTTTGT TAAATCAGCT CATTTTTTAA CCAATAGGCC GAAATCGGCA AAATCCCTTA TAAATCAAAA GAATA-
     GACCG
     AGATAGGGTT GAGTGTTGTT

5201 CCAGTTTGGA ACAAGAGTCC ACTATTAAAG AACGTGGACT CCAACGTCAA AGGGCGAAAA ACCGTCTATC AGGGC-
     GATGG
     CCCACTACGT GAACCATCAC

5301 CCTAATCAAG TTTTTTGGGG TCGAGGTGCC GTAAAGCACT AAATCGGAAC CCTAAAGGGA GCCCCCGATT TAGAGCT-
     TGA
     CGGGGAAAGC CGGCGAACGT

5401 GGCGAGAAAG GAAGGGAAGA AAGCGAAAGG AGCGGGCGCT AGGGCGCTGG CAAGTGTAGC GGTCACGCTG CGCG-
     TAACCA
     CCACACCCGC CGCGCTTAAT

5501 GCGCCGCTAC AGGGCGCGTC GCGCCATTCG CCATTCAGGC TGCGCAACTG TTGGGAAGGG CGATCGGTGC GGGC-
     CTCTTC
     GCTATTACGC CAGCTGGCGA

5601 AAGGGGGATG TGCTGCAAGG CGATTAAGTT GGGTAACGCC AGGGTTTTCC CAGTCACGAC GTTGTAAAAC GACGGC-
     CAGT
     GAGCGCGCGT AATACGACTC

5701 ACTATAGGGC GAATTGGAAT TAATTCGCTG GGCTGAGACC CGCAGAGGAA GACGCTCTAG GGATTT-
     GTCC CGGACTAGCG
     AGATGGCAAG GCTGAGGACG

5801 GGAGGCTGAT TGAGAGGCGA AGGTACACCC TAATCTCAAT ACAACCCTTG GAGCTAAGCC AGCAATG-
     GTA GAGGGAAGAT
     TCTGCACGTC CCTTCCAGGC

5901 GGCCTCCCCG TCACCACCCA CCCCAACCCG CCCCGACCGG AGCTGAGAGT AATTCATACA AAAGGACTCG CCCCTGC-
     CTT
     GGGGAATCCC AGGGACCGTC
```

TABLE 17-continued

Sequence ID. NO. 17—Polynucleotide Sequence of the r-Antidote Expression Vector

```
6001 GTTAAACTCC CACTAACGTA GAACCCAGAG ATCGCTGCGT TCCCGCCCCC TCACCCGCCC GCTCTCGTCA TCACT-
     GAGGT
     GGAGAAGAGC ATGCGTGAGG

6101 CTCCGGTGCC CGTCAGTGGG CAGAGCGCAC ATCGCCCACA GTCCCCGAGA AGTTGGGGGG AGGGGTCGGC AATT-
     GAACCG
     GTGCCTAGAG AAGGTGGCGC

6201 GGGGTAAACT GGGAAAGTGA TGTCGTGTAC TGGCTCCGCC TTTTTCCCGA GGGTGGGGGA GAACCGTATA TAAGT-
     GCAGT
     AGTCGCCGTG AACGTTCTTT

6301 TTCGCAACGG GTTTGCCGCC AGAACACAGG TAAGTGCCGT GTGTGGTTCC CGCGGGCCTG GCCTCTTTAC GGGT-
     TATGGC
     CCTTGCGTGC CTTGAATTAC

6401 TTCCACGCCC CTGGCTGCAG TACGTGATTC TTGATCCCGA GCTTCGGGTT GAAAGTGGGT GGGAGAGTTC GAGGCCT-
     TGC
     GCTTAAGGAG CCCCTTCGCC

6501 TCGTGCTTGA GTTGAGGCCT GGCTTGGGCG CTGGGCCGC CGCGTGCGAA TCTGGTGGCA CCT-
     TCGCGCC TATCTCGCTG
     CTTTCGATAA GTCTCTAGCC

6601 ATTTAAAATT TTTGATGACC TGCTGCGACG CTTTTTTTCT GGCAAGATAG TCTTGTAAAT GCGGGCCAAG ATCTGCA-
     CAC
     TGGTATTTCG GTTTTTGGGG

6701 CCGCGGGCGG CGACGGGGCC CGTGCGTCCC AGCGCACATG TTCGGCGAGG CGGGGCCTGC GAGCGCGGCC ACCGA-
     GAATC
     GGACGGGGGT AGTCTCAAGC

6801 TGGCCGGCCT GCTCTGGTGC CTGGCCTCGC GCCGCCGTGT ATCGCCCCGC CCTGGGCGGC AAGGCTGGCC CGGTCG-
     GCAC
     CAGTTGCGTG AGCGGAAAGA

6901 TGGCCGCTTC CCGGCCCTGC TGCAGGGAGC TCAAAATGGA GGACGCGGCG CTCGGGAGAG CGGGCGGGTG AGTCAC-
     CCAC
     ACAAAGGAAA AGGGCCTTTC

7001 CGTCCTCAGC CGTCGCTTCA TGTGACTCCA CGGAGTACCG GGCGCCGTCC AGGCACCTCG ATTAGT-
     TCTC GAGCTTTTGG
     AGTACGTCGT CTTTAGGTTG

7101 GGGGGAGGGG TTTTATGCGA TGGAGTTTCC CCACACTGAG TGGGTGGAGA CTGAAGTTAG GCCAGCTTGG CACTT-
     GATGT
     AATTCTCCTT GGAATTTGCC

7201 CTTTTTGAGT TTGGATCTTG GTTCATTCTC AAGCCTCAGA CAGTGGTTCA AAGTTTTTTT CTTCCATTTC AGGT-
     GTCGTG
     AAAACTACCC CTAAAAGCCA

7301 AAT
```

TABLE 18

| Sequence ID NO. 18—Signal Sequence for SEQ ID NOs. 12-15 and 19-25 |
|---|
| Signal Sequence |
| SP1  MGRPLHLVLL SASLAGLLLL GESLFIRREQ ANNILARVTR |

TABLE 19

| Sequence ID NO. 19—DesGla Xi (with activation peptide) with 2 RKR linkers ("RKR" disclosed as SEQ ID NO: 40 and "RKRRKR" disclosed as SEQ ID NO: 41) |
|---|
| Light Chain |
| 1    ANSFL                                        F WNKYKDGDQC ETSPCQNQGK |
| 61   CKDGLGEYTC TCLEGFEGKN CELFTRKLCS LDNGDCDQFC HEEQNSVVCS CARGYTLADN |
| 121  GKACIPTGPY PCGKQTLER |

TABLE 19-continued

Sequence ID NO. 19—DesGla Xi (with activation peptide) with 2 RKR linkers ("RKR" disclosed as SEQ ID NO: 40 and "RKRRKR" disclosed as SEQ ID NO: 41)

Linker
       RKRRKR

Heavy Chain
121                       SVAQATSS SGEAPDSITW KPYDAADLDP TENPFDLLDF

181    NQTQPERGDN NLTRIVGGQE CKDGECPWQA LLINEENEGF CGGTILSEFY ILTAAHCLYQ

241    AKRFKVRVGD RNTEQEEGGE AVHEVEVVIK HNRFTKETYD FDIAVLRLKT PITFRMNVAP

301    ACLPERDWAE STLMTQKTGI VSGFGRTHEK GRQSTRLKML EVPYVDRNSC KLSSSFIITQ

361    NMFCAGYDTK QEDACQGDAG GPHVTRFKDT YFVTGIVSWG EGCARKGKYG IYTKVTAFLK

421    WIDRSMKTRG LPKAKSHAPE VITSSPLK

TABLE 20

Sequence ID NO. 20—DesGla Xai-beta form only-truncate at R

Light Chain
  1    ANSFL                                F WNKYKDGDQC ETSPCQNQGK

61    CKDGLGEYTC TCLEGFEGKN CELFTRKLCS LDNGDCDQFC HEEQNSVVCS CARGYTLADN

121    GKACIPTGPY PCGKQTLER

Linker
       RKRRKR

Heavy Chain
181              IVGGQE CKDGECPWQA LLINEENEGF CGGTILSEFY ILTAAHCLYQ

241    AKRFKVRVGD RNTEQEEGGE AVHEVEVVIK HNRFTKETYD FDIAVLRLKT PITFRMNVAP

301    ACLPERDWAE STLMTQKTGI VSGFGRTHEK GRQSTRLKML EVPYVDRNSC KLSSSFIITQ

361    NMFCAGYDTK QEDACQGDAG GPHVTRFKDT YFVTGIVSWG EGCARKGKYG IYTKVTAFLK

421    WIDRSMKTR

TABLE 21

Sequence ID NO. 21—DesGlaXai alpha form only

Light Chain
  1    ANSFL                                F WNKYKDGDQC ETSPCQNQGK

61    CKDGLGEYTC TCLEGFEGKN CELFTRKLCS LDNGDCDQFC HEEQNSVVCS CARGYTLADN

121    GKACIPTGPY PCGKQTLER

Linker
       RKRRKR

Heavy Chain
181              IVGGQE CKDGECPWQA LLINEENEGF CGGTILSEFY ILTAAHCLYQ

241    AKRFKVRVGD RNTEQEEGGE AVHEVEVVIK HNRFTKETYD FDIAVLRLKT PITFRMNVAP

301    ACLPERDWAE STLMTQKTGI VSGFGRTHEK GRQSTRLKML EVPYVDRNSC KLSSSFIITQ

361    NMFCAGYDTK QEDACQGDAG GPHVTRFKDT YFVTGIVSWG EGCARKGKYG IYTKVTAFLK

421    WIDRSMKTQG LPKAKSHAPE VITSSPLK

TABLE 22

Sequence ID NO. 22—DesGla Xai alpha form with glycosylation site removed

Light Chain
```
  1     ANSFL                          F WNKYKDGDQC ETSPCQNQGK
 61     CKDGLGEYTC TCLEGFEGKN CELFTRKLCS LDNGDCDQFC HEEQNSVVCS CARGYTLADN
121     GKACIPTGPY PCGKQTLER
```

Linker
```
        RKRRKR
```

Heavy Chain
```
181                IVGGQE CKDGECPWQA LLINEENEGF CGGTILSEFY ILTAAHCLYQ
241     AKRFKVRVGD RNTEQEEGGE AVHEVEVVIK HNRFTKETYD FDIAVLRLKT PITFRMNVAP
301     ACLPERDWAE STLMTQKTGI VSGFGRTHEK GRQSTRLKML EVPYVDRNSC KLSSSFIITQ
361     NMFCAGYDTK QEDACQGDAG GPHVTRFKDT YFVTGIVSWG EGCARKGKYG IYTKVTAFLK
421     WIDRSMKTQG LPKAKSHAPE VIASSPLK
```

TABLE 23

Sequence ID NO. 23—DesGla δEGF1 Xai

Light Chain
```
  1     ANSFL
 61                      TRKLCS LDNGDCDQFC HEEQNSVVCS CARGYTLADN
121     GKACIPTGPY PCGKQTLER
```

Linker
```
        RKRRKR
```

Heavy Chain
```
181                IVGGQE CKDGECPWQA LLINEENEGF CGGTILSEFY ILTAAHCLYQ
241     AKRFKVRVGD RNTEQEEGGE AVHEVEVVIK HNRFTKETYD FDIAVLRLKT PITFRMNVAP
301     ACLPERDWAE STLMTQKTGI VSGFGRTHEK GRQSTRLKML EVPYVDRNSC KLSSSFIITQ
361     NMFCAGYDTK QEDACQGDAG GPHVTRFKDT YFVTGIVSWG EGCARKGKYG IYTKVTAFLK
421     WIDRSMKTRG LPKAKSHAPE VITSSPLK
```

45

TABLE 24

Sequence ID NO. 24—DesGla Xi-RKR-alpha only form ("RKR" disclosed as SEQ ID NO: 40)

Light Chain
```
  1     ANSFL                          F WNKYKDGDQC ETSPCQNQGK
 61     CKDGLGEYTC TCLEGFEGKN CELFTRKLCS LDNGDCDQFC HEEQNSVVCS CARGYTLADN
121     GKACIPTGPY PCGKQTLER
```

Linker
```
        RKR
```

Heavy Chain
```
121                SVAQATSS SGEAPDSITW KPYDAADLDP TENPFDLLDF
181     NQTQPERGDN NLTRIVGGQE CKDGECPWQA LLINEENEGF CGGTILSEFY ILTAAHCLYQ
241     AKRFKVRVGD RNTEQEEGGE AVHEVEVVIK HNRFTKETYD FDIAVLRLKT PITFRMNVAP
301     ACLPERDWAE STLMTQKTGI VSGFGRTHEK GRQSTRLKML EVPYVDRNSC KLSSSFIITQ
```

TABLE 24-continued

Sequence ID NO. 24—DesGla Xi-RKR-alpha only form ("RKR" disclosed as SEQ ID NO: 40)

```
361    NMFCAGYDTK QEDACQGDAG GPHVTRFKDT YFVTGIVSWG EGCARKGKYG IYTKVTAFLK

421    WIDRSMKTQG LPKAKSHAPE VITSSPLK
```

TABLE 25

Sequence ID NO. 25—triple mutant factor Xa construct with single RKR linker (SEQ ID NO: 40)

```
Light Chain
  1        ANSFL                              F WNKYKDGDQC ETSPCQNQGK

61    CKDGLGEYTC TCLEGFEGKN CELFTRKLCS LDNGDCDQFC HEEQNSVVCS CARGYTLADN

121        GKACIPTGPY PCGKQTLER

Linker
        RKR

Heavy Chain
181                  IVGGQE CKDGECPWQA LLINEENEGF CGGTILSEFY ILTAAHCLYQ

241    AKRFKVRVGD RNTEQEEGGE AVHEVEVVIK HNRFTKETYD FDIAVLRLKT PITFRMNVAP

301    ACLPERDWAE STLMTQKTGI VSGFGRTHEK GRQSTRLKML EVPYVDRNSC KLSSSFIITQ

361    NMFCAGYDTK QEDACQGDAG GPHVTRFKDT YFVTGIVSWG EGCARKGKYG IYTKVTAFLK

421    WIDRSMKTRG LPKAKSHAPE VITSSPLK
```

TABLE 26

Sequence ID NO. 26—Des Gla Xai with the prepropeptide of human prothrombin fused to ANSFL (SEQ ID NO: 42)

```
Signal Sequence
SP1    MAHVRGLQLP GCLALAALCS LVHS

Light Chain
  1        ANSFL                              F WNKYKDGDQC ETSPCQNQGK

61    CKDGLGEYTC TCLEGFEGKN CELFTRKLCS LDNGDCDQFC HEEQNSVVCS CARGYTLADN

121        GKACIPTGPY PCGKQTLER

Linker
        RKRRKR

Heavy Chain
181                  IVGGQE CKDGECPWQA LLINEENEGF CGGTILSEFY ILTAAHCLYQ

241    AKRFKVRVGD RNTEQEEGGE AVHEVEVVIK HNRFTKETYD FDIAVLRLKT PITFRMNVAP

301    ACLPERDWAE STLMTQKTGI VSGFGRTHEK GRQSTRLKML EVPYVDRNSC KLSSSFIITQ

361    NMFCAGYDTK QEDACQGDAG GPHVTRFKDT YFVTGIVSWG EGCARKGKYG IYTKVTAFLK

421    WIDRSMKTRG LPKAKSHAPE VITSSPLK
```

TABLE 27

Sequence ID NO. 27—Alternate signal sequences, Des Gla Xai with transferrin signal peptide replacing native Xa signal peptide

```
Signal Sequence
SP1    MRLAVGALLV CAVLGLCLA

Light Chain
  1                                           ANSFL          F WNKYKDGDQC ETSPCQNQGK
 61    CKDGLGEYTC TCLEGFEGKN CELFTRKLCS LDNGDCDQFC HEEQNSVVCS CARGYTLADN
121    GKACIPTGPY PCGKQTLER Linker
       RKRRKR Heavy Chain
181               IVGGQE CKDGECPWQA LLINEENEGF CGGTILSEFY ILTAAHCLYQ
241    AKRF -continued Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys

```
                435                 440                 445
Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485
```

<210> SEQ ID NO 2
<211> LENGTH: 1560
<212> TYPE: DNA
<213> ORGANISM: Homo sapiens

<400> SEQUENCE: 2

| | | | | | |
|---|---|---|---|---|---|
| gactttgctc | cagcagcctg | tcccagtgag | gacagggaca | cagtactcgg | ccacaccatg | 60 |
| gggcgcccac | tgcacctcgt | cctgctcagt | gcctccctgg | ctggcctcct | gctgctcggg | 120 |
| gaaagtctgt | tcatccgcag | ggagcaggcc | aacaacatcc | tggcgagggt | cacgagggcc | 180 |
| aattcctttc | ttgaagagat | gaagaaagga | cacctcgaaa | gagagtgcat | ggaagagacc | 240 |
| tgctcatacg | aagaggcccg | cgaggtcttt | gaggacagcg | acaagacgaa | tgaattctgg | 300 |
| aataaataca | agatggcgga | ccagtgtgag | accagtcctt | gccagaacca | gggcaaatgt | 360 |
| aaagacggcc | tcgggggaata | cacctgcacc | tgtttagaag | gattcgaagg | caaaaactgt | 420 |
| gaattattca | cacggaagct | ctgcagcctg | acaacggggg | actgtgacca | gttctgccac | 480 |
| gaggaacaga | actctgtggt | gtgctcctgc | gcccgcgggt | acaccctggc | tgacaacggc | 540 |
| aaggcctgca | ttcccacagg | gccctacccc | tgtgggaaac | agaccctgga | acgcaggaag | 600 |
| aggtcagtgg | cccaggccac | cagcagcagc | ggggaggccc | ctgacagcat | cacatggaag | 660 |
| ccatatgatg | cagccgacct | ggaccccacc | gagaacccct | cgacctgctg | tgacttcaac | 720 |
| cagacgcagc | tgagaggggc | cgacaacaac | ctcaccagga | tcgtgggagg | ccaggaatgc | 780 |
| aaggacgggg | agtgtccctg | gcaggccctg | ctcatcaatg | aggaaaacga | gggtttctgt | 840 |
| ggtggaacca | ttctgagcga | gttctacatc | ctaacggcag | cccactgtct | ctaccaagcc | 900 |
| aagagattca | aggtgagggt | aggggaccgg | aacacggagc | aggaggaggg | cggtgaggcg | 960 |
| gtgcacgagg | tggaggtggt | catcaagcac | aaccggttca | caaaggagac | ctatgacttc | 1020 |
| gacatcgccg | tgctccggct | caagacccc | atcaccttcc | gcatgaacgt | ggcgcctgcc | 1080 |
| tgcctccccg | agcgtgactg | ggccgagtcc | acgctgatga | cgcagaagac | ggggattgtg | 1140 |
| agcggcttcg | ggcgcaccca | cgagaagggc | cggcagtcca | ccaggctcaa | gatgctggag | 1200 |
| gtgccctacg | tggaccgcaa | cagctgcaag | ctgtccagca | gcttcatcat | cacccagaac | 1260 |
| atgttctgtg | ccggctacga | caccaagcag | gaggatgcct | gccaggggga | cagcgggggc | 1320 |
| ccgcacgtca | cccgcttcaa | ggacacctac | ttcgtgacag | gcatcgtcag | ctggggagag | 1380 |
| ggctgtgccc | gtaaggggaa | gtacgggatc | tacaccaagg | tcaccgcctt | cctcaagtgg | 1440 |
| atcgacaggt | ccatgaaaac | caggggcttg | cccaaggcca | agagccatgc | cccggaggtc | 1500 |
| ataacgtcct | ctccattaaa | gtgagatccc | actcaaaaaa | aaaaaaaaaa | aaaaaaaaa | 1560 |

<210> SEQ ID NO 3
<211> LENGTH: 448
<212> TYPE: PRT
<213> ORGANISM: Homo sapiens

<400> SEQUENCE: 3

-continued

```
Ala Asn Ser Phe Leu Glu Glu Met Lys Lys Gly His Leu Glu Arg Glu
 1               5                  10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
```

420                 425                 430
Lys Ala Lys Ser His Ala Pro Glu Val Ile Thr Ser Ser Pro Leu Lys
            435                 440                 445

<210> SEQ ID NO 4
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Lys Asp Gly Asp Gln Cys Glu Thr Ser Pro Cys Gln Asn Gln Gly Lys
1               5                   10                  15

Cys Lys Asp Gly Leu Gly Glu Tyr Thr Cys Thr Cys Leu Glu Gly Phe
            20                  25                  30

Glu Gly Lys Asn Cys Glu Leu Phe Thr Arg Lys Leu Cys Ser Leu Asp
        35                  40                  45

Asn Gly Asp Cys Asp Gln Phe Cys His Glu Glu Gln Asn Ser Val Val
    50                  55                  60

Cys Ser Cys Ala Arg Gly Tyr Thr Leu Ala Asp Asn Gly Lys Ala Cys
65                  70                  75                  80

Ile Pro Thr Gly Pro Tyr Pro Cys Gly Lys Gln Thr Leu Glu Arg Ile
                85                  90                  95

Val Gly Gly Gln Glu Cys Lys Asp Gly Glu Cys Pro Trp Gln Ala Leu
            100                 105                 110

Leu Ile Asn Glu Glu Asn Glu Gly Phe Cys Gly Gly Thr Ile Leu Ser
        115                 120                 125

Glu Phe Tyr Ile Leu Thr Ala Ala His Cys Leu Tyr Gln Ala Lys Arg
    130                 135                 140

Phe Lys Val Arg Val Gly Asp Arg Asn Thr Glu Gln Glu Glu Gly Gly
145                 150                 155                 160

Glu Ala Val His Glu Val Glu Val Val Ile Lys His Asn Arg Phe Thr
                165                 170                 175

Lys Glu Thr Tyr Asp Phe Asp Ile Ala Val Leu Arg Leu Lys Thr Pro
            180                 185                 190

Ile Thr Phe Arg Met Asn Val Ala Pro Ala Cys Leu Pro Glu Arg Asp
        195                 200                 205

Trp Ala Glu Ser Thr Leu Met Thr Gln Lys Thr Gly Ile Val Ser Gly
    210                 215                 220

Phe Gly Arg Thr His Glu Lys Gly Arg Gln Ser Thr Arg Leu Lys Met
225                 230                 235                 240

Leu Glu Val Pro Tyr Val Asp Arg Asn Ser Cys Lys Leu Ser Ser Ser
                245                 250                 255

Phe Ile Ile Thr Gln Asn Met Phe Cys Ala Gly Tyr Asp Thr Lys Gln
            260                 265                 270

Glu Asp Ala Cys Gln Gly Asp Ser Gly Gly Pro His Val Thr Arg Phe
        275                 280                 285

Lys Asp Thr Tyr Phe Val Thr Gly Ile Val Ser Trp Gly Glu Gly Cys
    290                 295                 300

Ala Arg Lys Gly Lys Tyr Gly Ile Tyr Thr Lys Val Thr Ala Phe Leu
305                 310                 315                 320

Lys Trp Ile Asp Arg Ser Met Lys Thr Arg Gly Leu Pro Lys Ala Lys
                325                 330                 335

```
Ser His Ala Pro Glu Val Ile Thr Ser Ser Pro Leu Lys
        340                 345

<210> SEQ ID NO 5
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Gly Asp Gln Cys Glu Thr Ser Pro Cys Gln Asn Gln Gly Lys Cys
1               5                   10                  15

Lys Asp Gly Leu Gly Glu Tyr Thr Cys Thr Cys Leu Glu Gly Phe Glu
            20                  25                  30

Gly Lys Asn Cys Glu Leu Phe Thr Arg Lys Leu Cys Ser Leu Asp Asn
        35                  40                  45

Gly Asp Cys Asp Gln Phe Cys His Glu Glu Gln Asn Ser Val Val Cys
    50                  55                  60

Ser Cys Ala Arg Gly Tyr Thr Leu Ala Asp Asn Gly Lys Ala Cys Ile
65                  70                  75                  80

Pro Thr Gly Pro Tyr Pro Cys Gly Lys Gln Thr Leu Glu Arg Ile Val
                85                  90                  95

Gly Gly Gln Glu Cys Lys Asp Gly Glu Cys Pro Trp Gln Ala Leu Leu
            100                 105                 110

Ile Asn Glu Glu Asn Glu Gly Phe Cys Gly Gly Thr Ile Leu Ser Glu
        115                 120                 125

Phe Tyr Ile Leu Thr Ala Ala His Cys Leu Tyr Gln Ala Lys Arg Phe
    130                 135                 140

Lys Val Arg Val Gly Asp Arg Asn Thr Glu Gln Glu Glu Gly Gly Glu
145                 150                 155                 160

Ala Val His Glu Val Glu Val Val Ile Lys His Asn Arg Phe Thr Lys
                165                 170                 175

Glu Thr Tyr Asp Phe Asp Ile Ala Val Leu Arg Leu Lys Thr Pro Ile
            180                 185                 190

Thr Phe Arg Met Asn Val Ala Pro Ala Cys Leu Pro Glu Arg Asp Trp
        195                 200                 205

Ala Glu Ser Thr Leu Met Thr Gln Lys Thr Gly Ile Val Ser Gly Phe
    210                 215                 220

Gly Arg Thr His Glu Lys Gly Arg Gln Ser Thr Arg Leu Lys Met Leu
225                 230                 235                 240

Glu Val Pro Tyr Val Asp Arg Asn Ser Cys Lys Leu Ser Ser Ser Phe
                245                 250                 255

Ile Ile Thr Gln Asn Met Phe Cys Ala Gly Tyr Asp Thr Lys Gln Glu
            260                 265                 270

Asp Ala Cys Gln Gly Asp Ser Gly Gly Pro His Val Thr Arg Phe Lys
        275                 280                 285

Asp Thr Tyr Phe Val Thr Gly Ile Val Ser Trp Gly Glu Gly Cys Ala
    290                 295                 300

Arg Lys Gly Lys Tyr Gly Ile Tyr Thr Lys Val Thr Ala Phe Leu Lys
305                 310                 315                 320

Trp Ile Asp Arg Ser Met Lys Thr Arg Gly Leu Pro Lys Ala Lys Ser
                325                 330                 335

His Ala Pro Glu Val Ile Thr Ser Ser Pro Leu Lys
            340                 345
```

```
<210> SEQ ID NO 6
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Ile Val Gly Gly Gln
130                 135                 140

Glu Cys Lys Asp Gly Glu Cys Pro Trp Gln Ala Leu Leu Ile Asn Glu
145                 150                 155                 160

Glu Asn Glu Gly Phe Cys Gly Gly Thr Ile Leu Ser Glu Phe Tyr Ile
                165                 170                 175

Leu Thr Ala Ala His Cys Leu Tyr Gln Ala Lys Arg Phe Lys Val Arg
            180                 185                 190

Val Gly Asp Arg Asn Thr Glu Gln Glu Glu Gly Gly Glu Ala Val His
        195                 200                 205

Glu Val Glu Val Val Ile Lys His Asn Arg Phe Thr Lys Glu Thr Tyr
    210                 215                 220

Asp Phe Asp Ile Ala Val Leu Arg Leu Lys Thr Pro Ile Thr Phe Arg
225                 230                 235                 240

Met Asn Val Ala Pro Ala Cys Leu Pro Glu Arg Asp Trp Ala Glu Ser
                245                 250                 255

Thr Leu Met Thr Gln Lys Thr Gly Ile Val Ser Gly Phe Gly Arg Thr
            260                 265                 270

His Glu Lys Gly Arg Gln Ser Thr Arg Leu Lys Met Leu Glu Val Pro
        275                 280                 285

Tyr Val Asp Arg Asn Ser Cys Lys Leu Ser Ser Phe Ile Ile Thr
    290                 295                 300

Gln Asn Met Phe Cys Ala Gly Tyr Asp Thr Lys Gln Glu Asp Ala Cys
305                 310                 315                 320

Gln Gly Asp Ser Gly Gly Pro His Val Thr Arg Phe Lys Asp Thr Tyr
                325                 330                 335

Phe Val Thr Gly Ile Val Ser Trp Gly Glu Gly Cys Ala Arg Lys Gly
            340                 345                 350

Lys Tyr Gly Ile Tyr Thr Lys Val Thr Ala Phe Leu Lys Trp Ile Asp
```

-continued

```
                355                 360                 365
Arg Ser Met Lys Thr Arg Gly Leu Pro Lys Ala Lys Ser His Ala Pro
    370                 375                 380

Glu Val Ile Thr Ser Ser Pro Leu Lys
385                 390

<210> SEQ ID NO 7
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(7)
<223> OTHER INFORMATION: Gamma-Carboxyglutamic acid
<220> FEATURE:
<221> NAME/KEY: MOD_RES
<222> LOCATION: (14)..(14)
<223> OTHER INFORMATION: Gamma-Carboxyglutamic acid
<220> FEATURE:
<221> NAME/KEY: MOD_RES
<222> LOCATION: (16)..(16)
<223> OTHER INFORMATION: Gamma-Carboxyglutamic acid
<220> FEATURE:
<221> NAME/KEY: MOD_RES
<222> LOCATION: (19)..(20)
<223> OTHER INFORMATION: Gamma-Carboxyglutamic acid
<220> FEATURE:
<221> NAME/KEY: MOD_RES
<222> LOCATION: (25)..(26)
<223> OTHER INFORMATION: Gamma-Carboxyglutamic acid
<220> FEATURE:
<221> NAME/KEY: MOD_RES
<222> LOCATION: (29)..(29)
<223> OTHER INFORMATION: Gamma-Carboxyglutamic acid
<220> FEATURE:
<221> NAME/KEY: MOD_RES
<222> LOCATION: (32)..(32)
<223> OTHER INFORMATION: Gamma-Carboxyglutamic acid
<220> FEATURE:
<221> NAME/KEY: MOD_RES
<222> LOCATION: (39)..(39)
<223> OTHER INFORMATION: Gamma-Carboxyglutamic acid

<400> SEQUENCE: 7

Ala Asn Ser Phe Leu Xaa Xaa Met Lys Lys Gly His Leu Xaa Arg Xaa
1               5                   10                  15

Cys Met Xaa Xaa Thr Cys Ser Tyr Xaa Xaa Ala Arg Xaa Val Phe Xaa
            20                  25                  30

Asp Ser Asp Lys Thr Asn Xaa Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Ile Val Gly Gly Gln
    130                 135                 140

Glu Cys Lys Asp Gly Glu Cys Pro Trp Gln Ala Leu Leu Ile Asn Glu
```

```
                145                 150                 155                 160
        Glu Asn Glu Gly Phe Cys Gly Gly Thr Ile Leu Ser Glu Phe Tyr Ile
                        165                 170                 175

Leu Thr Ala Ala His Cys Leu Tyr Gln Ala Lys Arg Phe Lys Val Arg
                        180                 185                 190

Val Gly Asp Arg Asn Thr Glu Gln Glu Glu Gly Gly Glu Ala Val His
                        195                 200                 205

Glu Val Glu Val Val Ile Lys His Asn Arg Phe Thr Lys Glu Thr Tyr
                        210                 215                 220

Asp Phe Asp Ile Ala Val Leu Arg Leu Lys Thr Pro Ile Thr Phe Arg
        225                 230                 235                 240

Met Asn Val Ala Pro Ala Cys Leu Pro Glu Arg Asp Trp Ala Glu Ser
                            245                 250                 255

Thr Leu Met Thr Gln Lys Thr Gly Ile Val Ser Gly Phe Gly Arg Thr
                        260                 265                 270

His Glu Lys Gly Arg Gln Ser Thr Arg Leu Lys Met Leu Glu Val Pro
                        275                 280                 285

Tyr Val Asp Arg Asn Ser Cys Lys Leu Ser Ser Ser Phe Ile Ile Thr
                        290                 295                 300

Gln Asn Met Phe Cys Ala Gly Tyr Asp Thr Lys Gln Glu Asp Ala Cys
        305                 310                 315                 320

Gln Gly Asp Ser Gly Gly Pro His Val Thr Arg Phe Lys Asp Thr Tyr
                        325                 330                 335

Phe Val Thr Gly Ile Val Ser Trp Gly Glu Gly Cys Ala Arg Lys Gly
                        340                 345                 350

Lys Tyr Gly Ile Tyr Thr Lys Val Thr Ala Phe Leu Lys Trp Ile Asp
                        355                 360                 365

Arg Ser Met Lys Thr Arg Gly Leu Pro Lys Ala Lys Ser His Ala Pro
                        370                 375                 380

Glu Val Ile Thr Ser Ser Pro Leu Lys
        385                 390

<210> SEQ ID NO 8
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(7)
<223> OTHER INFORMATION: Gamma-Carboxyglutamic acid
<220> FEATURE:
<221> NAME/KEY: MOD_RES
<222> LOCATION: (14)..(14)
<223> OTHER INFORMATION: Gamma-Carboxyglutamic acid
<220> FEATURE:
<221> NAME/KEY: MOD_RES
<222> LOCATION: (16)..(16)
<223> OTHER INFORMATION: Gamma-Carboxyglutamic acid
<220> FEATURE:
<221> NAME/KEY: MOD_RES
<222> LOCATION: (19)..(20)
<223> OTHER INFORMATION: Gamma-Carboxyglutamic acid
<220> FEATURE:
<221> NAME/KEY: MOD_RES
<222> LOCATION: (25)..(26)
<223> OTHER INFORMATION: Gamma-Carboxyglutamic acid
<220> FEATURE:
<221> NAME/KEY: MOD_RES
<222> LOCATION: (29)..(29)
<223> OTHER INFORMATION: Gamma-Carboxyglutamic acid
```

```
<220> FEATURE:
<221> NAME/KEY: MOD_RES
<222> LOCATION: (32)..(32)
<223> OTHER INFORMATION: Gamma-Carboxyglutamic acid
<220> FEATURE:
<221> NAME/KEY: MOD_RES
<222> LOCATION: (39)..(39)
<223> OTHER INFORMATION: Gamma-Carboxyglutamic acid

<400> SEQUENCE: 8

Ala Asn Ser Phe Leu Xaa Xaa Met Lys Lys Gly His Leu Xaa Arg Xaa
1               5                   10                  15

Cys Met Xaa Xaa Thr Cys Ser Tyr Xaa Xaa Ala Arg Xaa Val Phe Xaa
            20                  25                  30

Asp Ser Asp Lys Thr Asn Xaa Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg
    130                 135

<210> SEQ ID NO 9
<211> LENGTH: 254
<212> TYPE: PRT
<213> ORGANISM: Homo sapiens

<400> SEQUENCE: 9

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175
```

```
Gln Glu Asp Ala Cys Gln Gly Asp Ser Gly Gly Pro His Val Thr Arg
                180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 10
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (280)..(280)
<223> OTHER INFORMATION: Dehydroalanine

<400> SEQUENCE: 10

Lys Asp Gly Asp Gln Cys Glu Thr Ser Pro Cys Gln Asn Gln Gly Lys
1               5                   10                  15

Cys Lys Asp Gly Leu Gly Glu Tyr Thr Cys Thr Cys Leu Glu Gly Phe
                20                  25                  30

Glu Gly Lys Asn Cys Glu Leu Phe Thr Arg Lys Leu Cys Ser Leu Asp
            35                  40                  45

Asn Gly Asp Cys Asp Gln Phe Cys His Glu Glu Gln Asn Ser Val Val
        50                  55                  60

Cys Ser Cys Ala Arg Gly Tyr Thr Leu Ala Asp Asn Gly Lys Ala Cys
65                  70                  75                  80

Ile Pro Thr Gly Pro Tyr Pro Cys Gly Lys Gln Thr Leu Glu Arg Ile
                85                  90                  95

Val Gly Gly Gln Glu Cys Lys Asp Gly Glu Cys Pro Trp Gln Ala Leu
            100                 105                 110

Leu Ile Asn Glu Glu Asn Glu Gly Phe Cys Gly Gly Thr Ile Leu Ser
        115                 120                 125

Glu Phe Tyr Ile Leu Thr Ala Ala His Cys Leu Tyr Gln Ala Lys Arg
    130                 135                 140

Phe Lys Val Arg Val Gly Asp Arg Asn Thr Glu Gln Glu Glu Gly Gly
145                 150                 155                 160

Glu Ala Val His Glu Val Glu Val Val Ile Lys His Asn Arg Phe Thr
                165                 170                 175

Lys Glu Thr Tyr Asp Phe Asp Ile Ala Val Leu Arg Leu Lys Thr Pro
            180                 185                 190

Ile Thr Phe Arg Met Asn Val Ala Pro Ala Cys Leu Pro Glu Arg Asp
        195                 200                 205

Trp Ala Glu Ser Thr Leu Met Thr Gln Lys Thr Gly Ile Val Ser Gly
    210                 215                 220

Phe Gly Arg Thr His Glu Lys Gly Arg Gln Ser Thr Arg Leu Lys Met
225                 230                 235                 240

Leu Glu Val Pro Tyr Val Asp Arg Asn Ser Cys Lys Leu Ser Ser Ser
                245                 250                 255

Phe Ile Ile Thr Gln Asn Met Phe Cys Ala Gly Tyr Asp Thr Lys Gln
```

```
                260                 265                 270
Glu Asp Ala Cys Gln Gly Asp Xaa Gly Gly Pro His Val Thr Arg Phe
            275                 280                 285
Lys Asp Thr Tyr Phe Val Thr Gly Ile Val Ser Trp Gly Glu Gly Cys
        290                 295                 300
Ala Arg Lys Gly Lys Tyr Gly Ile Tyr Thr Lys Val Thr Ala Phe Leu
305                 310                 315                 320
Lys Trp Ile Asp Arg Ser Met Lys Thr Arg Gly Leu Pro Lys Ala Lys
                325                 330                 335
Ser His Ala Pro Glu Val Ile Thr Ser Ser Pro Leu Lys
            340                 345

<210> SEQ ID NO 11
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Gly Asp Gln Cys Glu Thr Ser Pro Cys Gln Asn Gln Gly Lys Cys
1               5                   10                  15
Lys Asp Gly Leu Gly Glu Tyr Thr Cys Thr Cys Leu Glu Gly Phe Glu
            20                  25                  30
Gly Lys Asn Cys Glu Leu Phe Thr Arg Lys Leu Cys Ser Leu Asp Asn
        35                  40                  45
Gly Asp Cys Asp Gln Phe Cys His Glu Glu Gln Asn Ser Val Val Cys
    50                  55                  60
Ser Cys Ala Arg Gly Tyr Thr Leu Ala Asp Asn Gly Lys Ala Cys Ile
65                  70                  75                  80
Pro Thr Gly Pro Tyr Pro Cys Gly Lys Gln Thr Leu Glu Arg Ile Val
                85                  90                  95
Gly Gly Gln Glu Cys Lys Asp Gly Glu Cys Pro Trp Gln Ala Leu Leu
            100                 105                 110
Ile Asn Glu Glu Asn Glu Gly Phe Cys Gly Gly Thr Ile Leu Ser Glu
        115                 120                 125
Phe Tyr Ile Leu Thr Ala Ala His Cys Leu Tyr Gln Ala Lys Arg Phe
    130                 135                 140
Lys Val Arg Val Gly Asp Arg Asn Thr Glu Gln Glu Glu Gly Gly Glu
145                 150                 155                 160
Ala Val His Glu Val Glu Val Val Ile Lys His Asn Arg Phe Thr Lys
                165                 170                 175
Glu Thr Tyr Asp Phe Asp Ile Ala Val Leu Arg Leu Lys Thr Pro Ile
            180                 185                 190
Thr Phe Arg Met Asn Val Ala Pro Ala Cys Leu Pro Glu Arg Asp Trp
        195                 200                 205
Ala Glu Ser Thr Leu Met Thr Gln Lys Thr Gly Ile Val Ser Gly Phe
    210                 215                 220
Gly Arg Thr His Glu Lys Gly Arg Gln Ser Thr Arg Leu Lys Met Leu
225                 230                 235                 240
Glu Val Pro Tyr Val Asp Arg Asn Ser Cys Lys Leu Ser Ser Ser Phe
                245                 250                 255
Ile Ile Thr Gln Asn Met Phe Cys Ala Gly Tyr Asp Thr Lys Gln Glu
            260                 265                 270
```

```
Asp Ala Cys Gln Gly Asp Ala Gly Gly Pro His Val Thr Arg Phe Lys
                275                 280                 285

Asp Thr Tyr Phe Val Thr Gly Ile Val Ser Trp Gly Glu Gly Cys Ala
290                 295                 300

Arg Lys Gly Lys Tyr Gly Ile Tyr Thr Lys Val Thr Ala Phe Leu Lys
305                 310                 315                 320

Trp Ile Asp Arg Ser Met Lys Thr Arg Gly Leu Pro Lys Ala Lys Ser
                325                 330                 335

His Ala Pro Glu Val Ile Thr Ser Ser Pro Leu Lys
                340                 345

<210> SEQ ID NO 12
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
                20                  25                  30

Glu Tyr Thr Cys Thr Cys Leu Glu Gly Phe Glu Gly Lys Asn Cys Glu
            35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Arg Lys Arg Ile
            100                 105                 110

Val Gly Gly Gln Glu Cys Lys Asp Gly Glu Cys Pro Trp Gln Ala Leu
        115                 120                 125

Leu Ile Asn Glu Glu Asn Glu Gly Phe Cys Gly Gly Thr Ile Leu Ser
    130                 135                 140

Glu Phe Tyr Ile Leu Thr Ala Ala His Cys Leu Tyr Gln Ala Lys Arg
145                 150                 155                 160

Phe Lys Val Arg Val Gly Asp Arg Asn Thr Glu Gln Glu Glu Gly Gly
                165                 170                 175

Glu Ala Val His Glu Val Glu Val Val Ile Lys His Asn Arg Phe Thr
            180                 185                 190

Lys Glu Thr Tyr Asp Phe Asp Ile Ala Val Leu Arg Leu Lys Thr Pro
        195                 200                 205

Ile Thr Phe Arg Met Asn Val Ala Pro Ala Cys Leu Pro Glu Arg Asp
    210                 215                 220

Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
                245                 250                 255

Leu Glu Val Pro Tyr Val Asp Arg Asn Ser Cys Lys Leu Ser Ser Ser
            260                 265                 270

Phe Ile Ile Thr Gln Asn Met Phe Cys Ala Gly Tyr Asp Thr Lys Gln
        275                 280                 285
```

Glu Asp Ala Cys Gln Gly Asp Ala Gly Gly Pro His Val Thr Arg Phe
            290                 295                 300

Lys Asp Thr Tyr Phe Val Thr Gly Ile Val Ser Trp Gly Glu Gly Cys
305                 310                 315                 320

Ala Arg Lys Gly Lys Tyr Gly Ile Tyr Thr Lys Val Thr Ala Phe Leu
                325                 330                 335

Lys Trp Ile Asp Arg Ser Met Lys Thr Arg Gly Leu Pro Lys Ala Lys
                340                 345                 350

Ser His Ala Pro Glu Val Ile Thr Ser Ser Pro Leu Lys
                355                 360                 365

<210> SEQ ID NO 13
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
                20                  25                  30

Glu Tyr Thr Cys Thr Cys Leu Glu Gly Phe Glu Gly Lys Asn Cys Glu
            35                  40                  45

Leu Phe Thr Arg Lys Leu Cys Ser Leu Asp Asn Gly Asp Cys Asp Gln
50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Ile Val Gly Gly Gln Glu Cys
            100                 105                 110

Lys Asp Gly Glu Cys Pro Trp Gln Ala Leu Leu Ile Asn Glu Glu Asn
        115                 120                 125

Glu Gly Phe Cys Gly Gly Thr Ile Leu Ser Glu Phe Tyr Ile Leu Thr
130                 135                 140

Ala Ala His Cys Leu Tyr Gln Ala Lys Arg Phe Lys Val Arg Val Gly
145                 150                 155                 160

Asp Arg Asn Thr Glu Gln Glu Glu Gly Gly Glu Ala Val His Glu Val
                165                 170                 175

Glu Val Val Ile Lys His Asn Arg Phe Thr Lys Glu Thr Tyr Asp Phe
            180                 185                 190

Asp Ile Ala Val Leu Arg Leu Lys Thr Pro Ile Thr Phe Arg Met Asn
        195                 200                 205

Val Ala Pro Ala Cys Leu Pro Glu Arg Asp Trp Ala Glu Ser Thr Leu
210                 215                 220

Met Thr Gln Lys Thr Gly Ile Val Ser Gly Phe Gly Arg Thr His Glu
225                 230                 235                 240

Lys Gly Arg Gln Ser Thr Arg Leu Lys Met Leu Glu Val Pro Tyr Val
                245                 250                 255

Asp Arg Asn Ser Cys Lys Leu Ser Ser Ser Phe Ile Ile Thr Gln Asn
            260                 265                 270

Met Phe Cys Ala Gly Tyr Asp Thr Lys Gln Glu Asp Ala Cys Gln Gly

```
                275                 280                 285

Asp Ala Gly Gly Pro His Val Thr Arg Phe Lys Asp Thr Tyr Phe Val
    290                 295                 300

Thr Gly Ile Val Ser Trp Gly Glu Gly Cys Ala Arg Lys Gly Lys Tyr
305                 310                 315                 320

Gly Ile Tyr Thr Lys Val Thr Ala Phe Leu Lys Trp Ile Asp Arg Ser
                325                 330                 335

Met Lys Thr Arg Gly Leu Pro Lys Ala Lys Ser His Ala Pro Glu Val
            340                 345                 350

Ile Thr Ser Ser Pro Leu Lys
            355

<210> SEQ ID NO 14
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg
            100                 105

<210> SEQ ID NO 15
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
```

```
                    100                 105                 110
Asp Trp Ala Glu Ser Thr Leu Met Thr Gln Lys Thr Gly Ile Val Ser
            115                 120                 125

Gly Phe Gly Arg Thr His Glu Lys Gly Arg Gln Ser Thr Arg Leu Lys
        130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
        210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250
```

<210> SEQ ID NO 16
<211> LENGTH: 1218
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1215)

<400> SEQUENCE: 16

```
atg ggg cgc cca ctg cac ctc gtc ctg ctc agt gcc tcc ctg gct ggc    48
Met Gly Arg Pro Leu His Leu Val Leu Leu Ser Ala Ser Leu Ala Gly
1               5                   10                  15 ctc ctg ctg ctc ggg gaa agt ctg ttc atc cgc agg gag cag gcc aac    96
Leu Leu Leu Leu Gly Glu Ser Leu Phe Ile Arg Arg Glu Gln Ala Asn
            20                  25                  30 aac atc ctg gcg agg gtc acg agg gcc aat tcc ttt ctt ttc tgg aat   144
Asn Ile Leu Ala Arg Val Thr Arg Ala Asn Ser Phe Leu Phe Trp Asn
        35                  40                  45 aaa tac aaa gat ggc gac cag tgt gag acc agt cct tgc cag aac cag   192
Lys Tyr Lys Asp Gly Asp Gln Cys Glu Thr Ser Pro Cys Gln Asn Gln
    50                  55                  60 ggc aaa tgt aaa gac ggc ctc ggg gaa tac acc tgc acc tgt tta gaa   240
Gly Lys Cys Lys Asp Gly Leu Gly Glu Tyr Thr Cys Thr Cys Leu Glu
65                  70                  75                  80 gga ttc gaa ggc aaa aac tgt gaa tta ttc aca cgg aag ctc tgc agc   288
Gly Phe Glu Gly Lys Asn Cys Glu Leu Phe Thr Arg Lys Leu Cys Ser
                85                  90                  95 ctg gac aac ggg gac tgt gac cag ttc tgc cac gag gaa cag aac tct   336
Leu Asp Asn Gly Asp Cys Asp Gln Phe Cys His Glu Glu Gln Asn Ser
            100                 105                 110 gtg gtg tgc tcc tgc gcc cgc ggg tac acc ctg gct gac aac ggc aag   384
Val Val Cys Ser Cys Ala Arg Gly Tyr Thr Leu Ala Asp Asn Gly Lys
        115                 120                 125 gcc tgc att ccc aca ggg ccc tac ccc tgt ggg aaa cag acc ctg gaa   432
Ala Cys Ile Pro Thr Gly Pro Tyr Pro Cys Gly Lys Gln Thr Leu Glu
    130                 135                 140
```

```
cgc agg aag agg agg aag agg atc gtg gga ggc cag gaa tgc aag gac    480
Arg Arg Lys Arg Arg Lys Arg Ile Val Gly Gly Gln Glu Cys Lys Asp
145                 150                 155                 160 ggg gag tgt ccc tgg cag gcc ctg ctc atc aat gag gaa aac gag ggt    528
Gly Glu Cys Pro Trp Gln Ala Leu Leu Ile Asn Glu Glu Asn Glu Gly
                165                 170                 175 ttc tgt ggt gga acc att ctg agc gag ttc tac atc cta acg gca gcc    576
Phe Cys Gly Gly Thr Ile Leu Ser Glu Phe Tyr Ile Leu Thr Ala Ala
            180                 185                 190 cac tgt ctc tac caa gcc aag aga ttc aag gtg agg gta ggg gac cgg    624
His Cys Leu Tyr Gln Ala Lys Arg Phe Lys Val Arg Val Gly Asp Arg
        195                 200                 205 aac acg gag cag gag gag ggc ggt gag gcg gtg cac gag gtg gag gtg    672
Asn Thr Glu Gln Glu Glu Gly Gly Glu Ala Val His Glu Val Glu Val
    210                 215                 220 gtc atc aag cac aac cgg ttc aca aag gag acc tat gac ttc gac atc    720
Val Ile Lys His Asn Arg Phe Thr Lys Glu Thr Tyr Asp Phe Asp Ile
225                 230                 235                 240 gcc gtg ctc cgg ctc aag acc ccc atc acc ttc cgc atg aac gtg gcg    768
Ala Val Leu Arg Leu Lys Thr Pro Ile Thr Phe Arg Met Asn Val Ala
                245                 250                 255 cct gcc tgc ctc ccc gag cgt gac tgg gcc gag tcc acg ctg atg acg    816
Pro Ala Cys Leu Pro Glu Arg Asp Trp Ala Glu Ser Thr Leu Met Thr
            260                 265                 270 cag aag acg ggg att gtg agc ggc ttc ggg cgc acc cac gag aag ggc    864
Gln Lys Thr Gly Ile Val Ser Gly Phe Gly Arg Thr His Glu Lys Gly
        275                 280                 285 cgg cag tcc acc agg ctc aag atg ctg gag gtg ccc tac gtg gac cgc    912
Arg Gln Ser Thr Arg Leu Lys Met Leu Glu Val Pro Tyr Val Asp Arg
    290                 295                 300 aac agc tgc aag ctg tcc agc agc ttc atc atc acc cag aac atg ttc    960
Asn Ser Cys Lys Leu Ser Ser Ser Phe Ile Ile Thr Gln Asn Met Phe
305                 310                 315                 320 tgt gcc ggc tac gac acc aag cag gag gat gcc tgc cag ggg gac gca   1008
Cys Ala Gly Tyr Asp Thr Lys Gln Glu Asp Ala Cys Gln Gly Asp Ala
                325                 330                 335 ggg ggc ccg cac gtc acc cgc ttc aag gac acc tac ttc gtg aca ggc   1056
Gly Gly Pro His Val Thr Arg Phe Lys Asp Thr Tyr Phe Val Thr Gly
            340                 345                 350 atc gtc agc tgg gga gag ggc tgt gcc cgt aag ggg aag tac ggg atc   1104
Ile Val Ser Trp Gly Glu Gly Cys Ala Arg Lys Gly Lys Tyr Gly Ile
        355                 360                 365 tac acc aag gtc acc gcc ttc ctc aag tgg atc gac agg tcc atg aaa   1152
Tyr Thr Lys Val Thr Ala Phe Leu Lys Trp Ile Asp Arg Ser Met Lys
    370                 375                 380 acc agg ggc ttg ccc aag gcc aag agc cat gcc ccg gag gtc ata acg   1200
Thr Arg Gly Leu Pro Lys Ala Lys Ser His Ala Pro Glu Val Ile Thr
385                 390                 395                 400 tcc tct cca tta aag tga                                           1218
Ser Ser Pro Leu Lys
                405
```

<210> SEQ ID NO 17
<211> LENGTH: 7303
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
tctagacaca gtactcggcc acaccatggg gcgcccactg cacctcgtcc tgctcagtgc    60
ctccctggct ggcctcctgc tgctcgggga agtctgttc atccgcaggg agcaggccaa    120
caacatcctg gcgagggtca cgagggccaa ttcctttctt ttctggaata aatacaaaga   180
tggcgaccag tgtgagacca gtccttgcca gaaccagggc aaatgtaaag acggcctcgg   240
ggaatacacc tgcacctgtt tagaaggatt cgaaggcaaa aactgtgaat tattcacacg   300
gaagctctgc agcctggaca acggggactg tgaccagttc tgccacgagg aacagaactc   360
tgtggtgtgc tcctgcgccc gcgggtacac cctggctgac aacggcaagg cctgcattcc   420
cacagggccc taccctgtg gaaacagac cctggaacgc aggaagagga ggaagaggat     480
cgtgggaggc caggaatgca aggacgggga gtgtccctgg caggccctgc tcatcaatga   540
ggaaaacgag ggtttctgtg gtggaaccat tctgagcgag ttctacatcc taacggcagc   600
ccactgtctc taccaagcca agagattcaa ggtgagggta ggggaccgga cacggagca    660
ggaggagggc ggtgaggcgg tgcacgaggt ggaggtggtc atcaagcaca accggttcac   720
aaaggagacc tatgacttcg acatcgccgt gctccggctc aagaccccca tcaccttccg   780
catgaacgtg gcgcctgcct gcctccccga gcgtgactgg gccgagtcca cgctgatgac   840
gcagaagacg gggattgtga gcggcttcgg gcgcacccac gagaagggcc ggcagtccac   900
caggctcaag atgctggagg tgccctacgt ggaccgcaac agctgcaagc tgtccagcag   960
cttcatcatc acccagaaca tgttctgtgc cggctacgac accaagcagg aggatgcctg   1020
ccagggggac gcaggggcc cgcacgtcac ccgcttcaag gacacctact tcgtgacagg    1080
catcgtcagc tggggagagg gctgtgcccg taagggaag tacgggatct acaccaaggt    1140
caccgccttc ctcaagtgga tcgacaggtc catgaaaacc aggggcttgc caaggccaa    1200
gagccatgcc ccgaggtca taacgtcctc tccattaaag tgagatccca ctcggatccc    1260
tattctatag tgtcacctaa atgctagagc tcgctgatca gcctcgactg tgccttctag   1320
ttgccagcca tctgttgttt gcccctcccc cgtgccttcc ttgaccctgg aaggtgccac   1380
tcccactgtc ctttcctaat aaaatgagga aattgcatcg cattgtctga gtaggtgtca   1440
ttctattctg gggggtgggg tgggcagga cagcaagggg gaggattggg aagacaatag    1500
caggcatgct ggggatgcgg tgggctctat ggcttctgag gcggaaagaa ccagctgggg   1560
ctcgagcggc cgcccttct gaggcggaaa gaaccagctg tggaatgtgt gtcagttagg    1620
gtgtggaaag tccccaggct ccccagcagg cagaagtatg caaagcatgc atctcaatta   1680
gtcagcaacc aggtgtggaa agtccccagg ctccccagca ggcagaagta tgcaaagcat   1740
gcatctcaat tagtcagcaa ccatagtccc gccctaact ccgcccatcc cgccctaac    1800
tccgcccagt tccgcccatt ctccgcccca tggctgacta atttttttta tttatgcaga   1860
ggccgaggcc gcctcggcct ctgagctatt ccagaagtag tgaggaggct ttttggagg    1920
cctaggcttt tgcaaaaaag ctagcttccc gctgccatca tggttcgacc attgaactgc   1980
atcgtcgccg tgtcccaaaa tatggggatt ggcaagaacg agacctacc ctggcctccg    2040
ctcaggaacg agttcaagta cttccaaaga atgaccacaa cctcttcagt ggaaggtaaa   2100
cagaatctgg tgattatggg taggaaaacc tggttctcca ttcctgagaa gatcgacct    2160
ttaaaggaca gaattaatat agttctcagt agagaactca agaaccacc acgaggagct    2220
cattttcttg ccaaaagttt ggatgatgcc ttaagactta ttgaacaacc ggaattggca   2280
agtaaagtag acatggtttg gatagtcgga ggcagttctg tttaccagga agccatgaat   2340
caaccaggcc accttagact ctttgtgaca aggatcatgc aggaatttga agtgacacg    2400
```

```
tttttcccag aaattgattt ggggaaatat aaacttctcc cagaataccc aggcgtcctc    2460
tctgaggtcc aggaggaaaa aggcatcaag tataagtttg aagtctacga gaagaaagac    2520
taacaggaag atgctttcaa gttctctgct cccctcctaa agctatgcat ttttataaga    2580
ccatgggact tttgctggct ttagatcccg cggagatcca gacatgataa gatacattga    2640
tgagtttgga caaccacaa ctagaatgca gtgaaaaaaa tgctttattt gtgaaatttg     2700
tgatgctatt gctttatttg taaccattat aagctgcaat aaacaagtta caacaacaa     2760 ttgcattcat tttatgtttc aggttcaggg ggaggtgtgg gaggtttttt aaagcaagta    2820
aaacctctac aaatgtggta tggctgatta tgagctccag cttttgttcc ctttagtgag    2880
ggttaattgc gcgcttggcg taatcatggt catagctgtt tcctgtgtga aattgttatc    2940
cgctcacaat tccacacaac atacgagccg gaagcataaa gtgtaaagcc tggggtgcct    3000
aatgagtgag ctaactcaca ttaattgcgt tgcgctcact gcccgctttc cagtcgggaa    3060
acctgtcgtg ccagctgcat taatgaatcg gccaacgcgc ggggagaggc ggtttgcgta    3120
ttgggcgctc ttccgcttcc tcgctcactg actcgctgcg ctcggtcgtt cggctgcggc    3180
gagcggtatc agctcactca aaggcggtaa tacggttatc cacagaatca ggggataacg    3240
caggaaagaa catgtgagca aaaggccagc aaaaggccag gaaccgtaaa aaggccgcgt    3300
tgctggcgtt tttccatagg ctccgccccc ctgacgagca tcacaaaaat cgacgctcaa    3360
gtcagaggtg gcgaaacccg acaggactat aaagatacca ggcgtttccc cctggaagct    3420
ccctcgtgcg ctctcctgtt ccgaccctgc cgcttaccgg atacctgtcc gcctttctcc    3480
cttcgggaag cgtggcgctt tctcatagct cacgctgtag gtatctcagt tcggtgtagg    3540
tcgttcgctc caagctgggc tgtgtgcacg aaccccccgt tcagcccgac cgctgcgcct    3600
tatccggtaa ctatcgtctt gagtccaacc cggtaagaca cgacttatcg ccactggcag    3660
cagccactgg taacaggatt agcagagcga ggtatgtagg cggtgctaca gagttcttga    3720
agtggtggcc taactacggc tacactagaa ggacagtatt tggtatctgc gctctgctga    3780
agccagttac cttcggaaaa agagttggta gctcttgatc cggcaaacaa accaccgctg    3840
gtagcggtgg tttttttgtt tgcaagcagc agattacgcg cagaaaaaaa ggatctcaag    3900
aagatccttt gatcttttct acggggtctg acgctcagtg gaacgaaaac tcacgttaag    3960
ggattttggt catgagatta tcaaaaagga tcttcaccta gatcctttta aattaaaaat    4020
gaagttttaa atcaatctaa agtatatatg agtaaacttg gtctgacagt taccaatgct    4080
taatcagtga ggcacctatc tcagcgatct gtctatttcg ttcatccata gttgcctgac    4140
tccccgtcgt gtagataact acgatacggg agggcttacc atctggcccc agtgctgcaa    4200
tgataccgcg agacccacgc tcaccggctc cagatttatc agcaataaac cagccagccg    4260
gaagggccga gcgcagaagt ggtcctgcaa ctttatccgc ctccatccag tctattaatt    4320
gttgccggga agctagagta agtagttcgc cagttaatag tttgcgcaac gttgttgcca    4380
ttgctacagg catcgtggtg tcacgctcgt cgtttggtat ggcttcattc agctccggtt    4440
cccaacgatc aaggcgagtt acatgatccc ccatgttgtg caaaaaagcg gttagctcct    4500
tcggtcctcc gatcgttgtc agaagtaagt tggccgcagt gttatcactc atggttatgg    4560
cagcactgca taattctctt actgtcatgc catccgtaag atgcttttct gtgactggtg    4620
agtactcaac caagtcattc tgagaatagt gtatgcggcg accgagttgc tcttgcccgg    4680
cgtcaatacg ggataatacc gcgccacata gcagaacttt aaaagtgctc atcattggaa    4740
```

```
aacgttcttc ggggcgaaaa ctctcaagga tcttaccgct gttgagatcc agttcgatgt      4800
aacccactcg tgcacccaac tgatcttcag catcttttac tttcaccagc gtttctgggt      4860
gagcaaaaac aggaaggcaa aatgccgcaa aaagggaat aagggcgaca cggaaatgtt       4920
gaatactcat actcttcctt tttcaatatt attgaagcat ttatcagggt tattgtctca      4980
tgagcggata catatttgaa tgtatttaga aaataaaca aatagggggtt ccgcgcacat      5040 ttccccgaaa agtgccacct gggaaattgt aaacgttaat attttgttaa aattcgcgtt     5100
aaatttttgt taaatcagct cattttttaa ccataggcc gaaatcggca aaatccctta      5160
taaatcaaaa gaatagaccg agatagggtt gagtgttgtt ccagtttgga caagagtcc      5220 actattaaag aacgtggact ccaacgtcaa agggcgaaaa accgtctatc agggcgatgg     5280
cccactacgt gaaccatcac cctaatcaag ttttttgggg tcgaggtgcc gtaaagcact     5340
aaatcggaac cctaaaggga gccccgatt tagagcttga cggggaaagc cggcgaacgt       5400
ggcgagaaag gaagggaaga aagcgaaagg agcgggcgct agggcgctgg caagtgtagc    5460
ggtcacgctg cgcgtaacca ccacacccgc cgcgcttaat gcgccgctac agggcgcgtc     5520
gcgccattcg ccattcaggc tgcgcaactg ttgggaaggg cgatcggtgc gggcctcttc     5580
gctattacgc cagctggcga aagggggatg tgctgcaagg cgattaagtt gggtaacgcc     5640
agggttttcc cagtcacgac gttgtaaaac gacggccagt gagcgcgcgt aatacgactc     5700
actatagggc gaattggaat taattcgctg gctgagacc cgcagaggaa gacgctctag      5760
ggatttgtcc cggactagcg agatggcaag gctgaggacg ggaggctgat tgagaggcga    5820
aggtacaccc taatctcaat acaacccttg gagctaagcc agcaatggta gagggaagat    5880
tctgcacgtc ccttccaggc ggcctcccg tcaccaccca ccccaacccg ccccgaccgg     5940
agctgagagt aattcataca aaaggactcg cccctgcctt ggggaatccc agggaccgtc    6000
gttaaactcc cactaacgta gaacccagag atcgctgcgt tcccgccccc tcacccgccc    6060
gctctcgtca tcactgaggt ggagaagagc atgcgtgagg ctccggtgcc cgtcagtggg    6120
cagagcgcac atcgcccaca gtccccgaga agttgggggg aggggtcggc aattgaaccg     6180
gtgcctagag aaggtggcgc ggggtaaact gggaaagtga tgtcgtgtac tggctccgcc    6240
tttttcccga gggtggggga gaaccgtata taagtgcagt agtcgccgtg aacgttcttt     6300
ttcgcaacgg gtttgccgcc agaacacagg taagtgccgt gtgtggttcc cgcgggcctg    6360
gcctctttac gggttatggc ccttgcgtgc cttgaattac ttccacgccc ctggctgcag    6420
tacgtgattc ttgatcccga gcttcgggtt gaaagtgggt gggagagttc gaggccttgc    6480
gcttaaggag ccccttcgcc tcgtgcttga gttgaggcct ggcttgggcg ctgggccgc     6540 cgcgtgcgaa tctggtggca ccttcgcgcc tatctcgctg ctttcgataa gtctctagcc     6600
atttaaaatt tttgatgacc tgctgcgacg ctttttttct ggcaagatag tcttgtaaat    6660
gcgggccaag atctgcacac tggtatttcg gttttttgggg ccgcgggcgg cgacggggcc   6720
cgtgcgtccc agcgcacatg ttcggcgagg cgggcctgc gagcgcggcc accgagaatc    6780
ggacgggggt agtctcaagc tggccggcct gctctggtgc ctggcctcgc gccgccgtgt    6840
atcgccccgc cctgggcggc aaggctgccc cggtcggcac cagttgcgtg agcggaaaga    6900
tggccgcttc ccggccctgc tgcagggagc tcaaaatgga ggacgcggcg ctcgggagag    6960
cgggcgggtg agtcacccac acaaaggaaa agggccttc cgtcctcagc cgtcgcttca     7020
tgtgactcca cggagtaccg ggcgccgtcc aggcacctcg attagttctc gagcttttgg    7080
agtacgtcgt ctttaggttg gggggagggg ttttatgcga tggagtttcc ccacactgag    7140
```

```
tgggtggaga ctgaagttag gccagcttgg cacttgatgt aattctcctt ggaatttgcc    7200 cttttttgagt ttggatcttg gttcattctc aagcctcaga cagtggttca aagttttttt    7260
cttccatttc aggtgtcgtg aaaactaccc ctaaaagcca aat                        7303
```

```
<210> SEQ ID NO 18
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg
            35                  40

<210> SEQ ID NO 19
<211> LENGTH: 417
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Lys Arg Ser
            100                 105                 110

Val Ala Gln Ala Thr Ser Ser Gly Glu Ala Pro Asp Ser Ile Thr
        115                 120                 125

Trp Lys Pro Tyr Asp Ala Ala Asp Leu Asp Pro Thr Glu Asn Pro Phe
    130                 135                 140

Asp Leu Leu Asp Phe Asn Gln Thr Gln Pro Glu Arg Gly Asp Asn Asn
145                 150                 155                 160

Leu Thr Arg Ile Val Gly Gly Gln Glu Cys Lys Asp Gly Glu Cys Pro
                165                 170                 175

Trp Gln Ala Leu Leu Ile Asn Glu Glu Asn Glu Gly Phe Cys Gly Gly
            180                 185                 190

Thr Ile Leu Ser Glu Phe Tyr Ile Leu Thr Ala Ala His Cys Leu Tyr
        195                 200                 205

Gln Ala Lys Arg Phe Lys Val Arg Val Gly Asp Arg Asn Thr Glu Gln
    210                 215                 220
```

```
Glu Gly Gly Glu Ala Val His Glu Val Glu Val Ile Lys His
225                 230                 235                 240

Asn Arg Phe Thr Lys Glu Thr Tyr Asp Phe Asp Ile Ala Val Leu Arg
            245                 250                 255

Leu Lys Thr Pro Ile Thr Phe Arg Met Asn Val Ala Pro Ala Cys Leu
                260                 265                 270

Pro Glu Arg Asp Trp Ala Glu Ser Thr Leu Met Thr Gln Lys Thr Gly
            275                 280                 285

Ile Val Ser Gly Phe Gly Arg Thr His Glu Lys Gly Arg Gln Ser Thr
290                 295                 300

Arg Leu Lys Met Leu Glu Val Pro Tyr Val Asp Arg Asn Ser Cys Lys
305                 310                 315                 320

Leu Ser Ser Ser Phe Ile Ile Thr Gln Asn Met Phe Cys Ala Gly Tyr
                325                 330                 335

Asp Thr Lys Gln Glu Asp Ala Cys Gln Gly Asp Ala Gly Gly Pro His
            340                 345                 350

Val Thr Arg Phe Lys Asp Thr Tyr Phe Val Thr Gly Ile Val Ser Trp
            355                 360                 365

Gly Glu Gly Cys Ala Arg Lys Gly Lys Tyr Gly Ile Tyr Thr Lys Val
370                 375                 380

Thr Ala Phe Leu Lys Trp Ile Asp Arg Ser Met Lys Thr Arg Gly Leu
385                 390                 395                 400

Pro Lys Ala Lys Ser His Ala Pro Glu Val Ile Thr Ser Ser Pro Leu
            405                 410                 415

Lys

<210> SEQ ID NO 20
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Asn Ser Phe Leu Phe Trp Asn Lys Tyr Lys Asp Gly Asp Gln Cys
1               5                   10                  15

Glu Thr Ser Pro Cys Gln Asn Gly Lys Cys Lys Asp Gly Leu Gly
            20                  25                  30

Glu Tyr Thr Cys Thr Cys Leu Glu Gly Phe Glu Gly Lys Asn Cys Glu
            35                  40                  45

Leu Phe Thr Arg Lys Leu Cys Ser Leu Asp Asn Gly Asp Cys Asp Gln
50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Arg Lys Arg Ile
            100                 105                 110

Val Gly Gly Gln Glu Cys Lys Asp Gly Glu Cys Pro Trp Gln Ala Leu
            115                 120                 125

Leu Ile Asn Glu Glu Asn Glu Gly Phe Cys Gly Gly Thr Ile Leu Ser
    130                 135                 140

Glu Phe Tyr Ile Leu Thr Ala Ala His Cys Leu Tyr Gln Ala Lys Arg
145                 150                 155                 160
```

```
Phe Lys Val Arg Val Gly Asp Arg Asn Thr Glu Gln Glu Glu Gly Gly
                165                 170                 175

Glu Ala Val His Glu Val Glu Val Val Ile Lys His Asn Arg Phe Thr
            180                 185                 190

Lys Glu Thr Tyr Asp Phe Asp Ile Ala Val Leu Arg Leu Lys Thr Pro
        195                 200                 205

Ile Thr Phe Arg Met Asn Val Ala Pro Ala Cys Leu Pro Glu Arg Asp
210                 215                 220

Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
                245                 250                 255

Leu Glu Val Pro Tyr Val Asp Arg Asn Ser Cys Lys Leu Ser Ser Ser
            260                 265                 270

Phe Ile Ile Thr Gln Asn Met Phe Cys Ala Gly Tyr Asp Thr Lys Gln
        275                 280                 285

Glu Asp Ala Cys Gln Gly Asp Ala Gly Gly Pro His Val Thr Arg Phe
290                 295                 300

Lys Asp Thr Tyr Phe Val Thr Gly Ile Val Ser Trp Gly Glu Gly Cys
305                 310                 315                 320

Ala Arg Lys Gly Lys Tyr Gly Ile Tyr Thr Lys Val Thr Ala Phe Leu
                325                 330                 335

Lys Trp Ile Asp Arg Ser Met Lys Thr Arg
                340                 345

<210> SEQ ID NO 21
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Arg Lys Arg Ile
            100                 105                 110

Val Gly Gly Gln Glu Cys Lys Asp Gly Glu Cys Pro Trp Gln Ala Leu
        115                 120                 125

Leu Ile Asn Glu Glu Asn Glu Gly Phe Cys Gly Gly Thr Ile Leu Ser
    130                 135                 140

Glu Phe Tyr Ile Leu Thr Ala Ala His Cys Leu Tyr Gln Ala Lys Arg
145                 150                 155                 160

Phe Lys Val Arg Val Gly Asp Arg Asn Thr Glu Gln Glu Glu Gly Gly
```

```
                  165                 170                 175
Glu Ala Val His Glu Val Glu Val Ile Lys His Asn Arg Phe Thr
            180                 185                 190

Lys Glu Thr Tyr Asp Phe Asp Ile Ala Val Leu Arg Leu Lys Thr Pro
        195                 200                 205

Ile Thr Phe Arg Met Asn Val Ala Pro Ala Cys Leu Pro Glu Arg Asp
    210                 215                 220

Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
                245                 250                 255

Leu Glu Val Pro Tyr Val Asp Arg Asn Ser Cys Lys Leu Ser Ser Ser
            260                 265                 270

Phe Ile Ile Thr Gln Asn Met Phe Cys Ala Gly Tyr Asp Thr Lys Gln
        275                 280                 285

Glu Asp Ala Cys Gln Gly Asp Ala Gly Gly Pro His Val Thr Arg Phe
    290                 295                 300

Lys Asp Thr Tyr Phe Val Thr Gly Ile Val Ser Trp Gly Glu Gly Cys
305                 310                 315                 320

Ala Arg Lys Gly Lys Tyr Gly Ile Tyr Thr Lys Val Thr Ala Phe Leu
                325                 330                 335

Lys Trp Ile Asp Arg Ser Met Lys Thr Gln Gly Leu Pro Lys Ala Lys
            340                 345                 350

Ser His Ala Pro Glu Val Ile Thr Ser Ser Pro Leu Lys
        355                 360                 365

<210> SEQ ID NO 22
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Lys Arg Ile
            100                 105                 110

Val Gly Gly Gln Glu Cys Lys Asp Gly Glu Cys Pro Trp Gln Ala Leu
        115                 120                 125

Leu Ile Asn Glu Glu Asn Glu Gly Phe Cys Gly Gly Thr Ile Leu Ser
    130                 135                 140

Glu Phe Tyr Ile Leu Thr Ala Ala His Cys Leu Tyr Gln Ala Lys Arg
145                 150                 155                 160
```

Phe Lys Val Arg Val Gly Asp Arg Asn Thr Glu Gln Glu Glu Gly Gly
                165                 170                 175

Glu Ala Val His Glu Val Glu Val Val Ile Lys His Asn Arg Phe Thr
        180                 185                 190

Lys Glu Thr Tyr Asp Phe Asp Ile Ala Val Leu Arg Leu Lys Thr Pro
            195                 200                 205

Ile Thr Phe Arg Met Asn Val Ala Pro Ala Cys Leu Pro Glu Arg Asp
        210                 215                 220

Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
                245                 250                 255

Leu Glu Val Pro Tyr Val Asp Arg Asn Ser Cys Lys Leu Ser Ser Ser
            260                 265                 270

Phe Ile Ile Thr Gln Asn Met Phe Cys Ala Gly Tyr Asp Thr Lys Gln
        275                 280                 285

Glu Asp Ala Cys Gln Gly Asp Ala Gly Gly Pro His Val Thr Arg Phe
        290                 295                 300

Lys Asp Thr Tyr Phe Val Thr Gly Ile Val Ser Trp Gly Glu Gly Cys
305                 310                 315                 320

Ala Arg Lys Gly Lys Tyr Gly Ile Tyr Thr Lys Val Thr Ala Phe Leu
                325                 330                 335

Lys Trp Ile Asp Arg Ser Met Lys Thr Gln Gly Leu Pro Lys Ala Lys
            340                 345                 350

Ser His Ala Pro Glu Val Ile Ala Ser Ser Pro Leu Lys
            355                 360                 365

<210> SEQ ID NO 23
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Asn Ser Phe Leu Thr Arg Lys Leu Cys Ser Leu Asp Asn Gly Asp
1               5                   10                  15

Cys Asp Gln Phe Cys His Glu Glu Gln Asn Ser Val Val Cys Ser Cys
            20                  25                  30

Ala Arg Gly Tyr Thr Leu Ala Asp Asn Gly Lys Ala Cys Ile Pro Thr
        35                  40                  45

Gly Pro Tyr Pro Cys Gly Lys Gln Thr Leu Glu Arg Arg Lys Arg Arg
    50                  55                  60

Lys Arg Ile Val Gly Gly Gln Glu Cys Lys Asp Gly Glu Cys Pro Trp
65                  70                  75                  80

Gln Ala Leu Leu Ile Asn Glu Glu Asn Glu Gly Phe Cys Gly Gly Thr
                85                  90                  95

Ile Leu Ser Glu Phe Tyr Ile Leu Thr Ala Ala His Cys Leu Tyr Gln
            100                 105                 110

Ala Lys Arg Phe Lys Val Arg Val Gly Asp Arg Asn Thr Glu Gln Glu
        115                 120                 125

Glu Gly Gly Glu Ala Val His Glu Val Glu Val Val Ile Lys His Asn
    130                 135                 140

Arg Phe Thr Lys Glu Thr Tyr Asp Phe Asp Ile Ala Val Leu Arg Leu
145                 150                 155                 160

```
Lys Thr Pro Ile Thr Phe Arg Met Asn Val Ala Pro Ala Cys Leu Pro
                165                 170                 175

Glu Arg Asp Trp Ala Glu Ser Thr Leu Met Thr Gln Lys Thr Gly Ile
            180                 185                 190

Val Ser Gly Phe Gly Arg Thr His Glu Lys Gly Arg Gln Ser Thr Arg
        195                 200                 205

Leu Lys Met Leu Glu Val Pro Tyr Val Asp Arg Asn Ser Cys Lys Leu
    210                 215                 220

Ser Ser Ser Phe Ile Ile Thr Gln Asn Met Phe Cys Ala Gly Tyr Asp
225                 230                 235                 240

Thr Lys Gln Glu Asp Ala Cys Gln Gly Asp Ala Gly Gly Pro His Val
                245                 250                 255

Thr Arg Phe Lys Asp Thr Tyr Phe Val Thr Gly Ile Val Ser Trp Gly
            260                 265                 270

Glu Gly Cys Ala Arg Lys Gly Lys Tyr Gly Ile Tyr Thr Lys Val Thr
        275                 280                 285

Ala Phe Leu Lys Trp Ile Asp Arg Ser Met Lys Thr Arg Gly Leu Pro
    290                 295                 300

Lys Ala Lys Ser His Ala Pro Glu Val Ile Thr Ser Ser Pro Leu Lys
305                 310                 315                 320

<210> SEQ ID NO 24
<211> LENGTH: 414
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Ser Val Ala Gln
            100                 105                 110

Ala Thr Ser Ser Ser Gly Glu Ala Pro Asp Ser Ile Thr Trp Lys Pro
        115                 120                 125

Tyr Asp Ala Ala Asp Leu Asp Pro Thr Glu Asn Pro Phe Asp Leu Leu
    130                 135                 140

Asp Phe Asn Gln Thr Gln Pro Glu Arg Gly Asp Asn Asn Leu Thr Arg
145                 150                 155                 160

Ile Val Gly Gly Gln Glu Cys Lys Asp Gly Glu Cys Pro Trp Gln Ala
                165                 170                 175

Leu Leu Ile Asn Glu Glu Asn Glu Gly Phe Cys Gly Gly Thr Ile Leu
            180                 185                 190

Ser Glu Phe Tyr Ile Leu Thr Ala Ala His Cys Leu Tyr Gln Ala Lys
```

```
            195                 200                 205
Arg Phe Lys Val Arg Val Gly Asp Arg Asn Thr Glu Gln Glu Glu Gly
    210                 215                 220

Gly Glu Ala Val His Glu Val Glu Val Val Ile Lys His Asn Arg Phe
225                 230                 235                 240

Thr Lys Glu Thr Tyr Asp Phe Asp Ile Ala Val Leu Arg Leu Lys Thr
                245                 250                 255

Pro Ile Thr Phe Arg Met Asn Val Ala Pro Ala Cys Leu Pro Glu Arg
            260                 265                 270

Asp Trp Ala Glu Ser Thr Leu Met Thr Gln Lys Thr Gly Ile Val Ser
        275                 280                 285

Gly Phe Gly Arg Thr His Glu Lys Gly Arg Gln Ser Thr Arg Leu Lys
    290                 295                 300

Met Leu Glu Val Pro Tyr Val Asp Arg Asn Ser Cys Lys Leu Ser Ser
305                 310                 315                 320

Ser Phe Ile Ile Thr Gln Asn Met Phe Cys Ala Gly Tyr Asp Thr Lys
                325                 330                 335

Gln Glu Asp Ala Cys Gln Gly Asp Ala Gly Gly Pro His Val Thr Arg
            340                 345                 350

Phe Lys Asp Thr Tyr Phe Val Thr Gly Ile Val Ser Trp Gly Glu Gly
        355                 360                 365

Cys Ala Arg Lys Gly Lys Tyr Gly Ile Tyr Thr Lys Val Thr Ala Phe
370                 375                 380

Leu Lys Trp Ile Asp Arg Ser Met Lys Thr Gln Gly Leu Pro Lys Ala
385                 390                 395                 400

Lys Ser His Ala Pro Glu Val Ile Thr Ser Ser Pro Leu Lys
                405                 410

<210> SEQ ID NO 25
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Ile Val Gly Gly
            100                 105                 110

Gln Glu Cys Lys Asp Gly Glu Cys Pro Trp Gln Ala Leu Leu Ile Asn
        115                 120                 125

Glu Glu Asn Glu Gly Phe Cys Gly Gly Thr Ile Leu Ser Glu Phe Tyr
    130                 135                 140
```

```
Ile Leu Thr Ala Ala His Cys Leu Tyr Gln Ala Lys Arg Phe Lys Val
145                 150                 155                 160

Arg Val Gly Asp Arg Asn Thr Glu Gln Glu Glu Gly Gly Glu Ala Val
                165                 170                 175

His Glu Val Glu Val Val Ile Lys His Asn Arg Phe Thr Lys Glu Thr
            180                 185                 190

Tyr Asp Phe Asp Ile Ala Val Leu Arg Leu Lys Thr Pro Ile Thr Phe
        195                 200                 205

Arg Met Asn Val Ala Pro Ala Cys Leu Pro Glu Arg Asp Trp Ala Glu
    210                 215                 220

Ser Thr Leu Met Thr Gln Lys Thr Gly Ile Val Ser Gly Phe Gly Arg
225                 230                 235                 240

Thr His Glu Lys Gly Arg Gln Ser Thr Arg Leu Lys Met Leu Glu Val
                245                 250                 255

Pro Tyr Val Asp Arg Asn Ser Cys Lys Leu Ser Ser Ser Phe Ile Ile
            260                 265                 270

Thr Gln Asn Met Phe Cys Ala Gly Tyr Asp Thr Lys Gln Glu Asp Ala
        275                 280                 285

Cys Gln Gly Asp Ala Gly Gly Pro His Val Thr Arg Phe Lys Asp Thr
    290                 295                 300

Tyr Phe Val Thr Gly Ile Val Ser Trp Gly Glu Gly Cys Ala Arg Lys
305                 310                 315                 320

Gly Lys Tyr Gly Ile Tyr Thr Lys Val Thr Ala Phe Leu Lys Trp Ile
                325                 330                 335

Asp Arg Ser Met Lys Thr Arg Gly Leu Pro Lys Ala Lys Ser His Ala
            340                 345                 350

Pro Glu Val Ile Thr Ser Ser Pro Leu Lys
        355                 360

<210> SEQ ID NO 26
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala His Val Arg Gly Leu Gln Leu Pro Gly Cys Leu Ala Leu Ala
1               5                   10                  15

Ala Leu Cys Ser Leu Val His Ser Ala Asn Ser Phe Leu Phe Trp Asn
            20                  25                  30

Lys Tyr Lys Asp Gly Asp Gln Cys Glu Thr Ser Pro Cys Gln Asn Gln
        35                  40                  45

Gly Lys Cys Lys Asp Gly Leu Gly Glu Tyr Thr Cys Thr Cys Leu Glu
    50                  55                  60

Gly Phe Glu Gly Lys Asn Cys Glu Leu Phe Thr Arg Lys Leu Cys Ser
65                  70                  75                  80

Leu Asp Asn Gly Asp Cys Asp Gln Phe Cys His Glu Glu Gln Asn Ser
                85                  90                  95

Val Val Cys Ser Cys Ala Arg Gly Tyr Thr Leu Ala Asp Asn Gly Lys
            100                 105                 110

Ala Cys Ile Pro Thr Gly Pro Tyr Pro Cys Gly Lys Gln Thr Leu Glu
        115                 120                 125

Arg Arg Lys Arg Arg Lys Arg Ile Val Gly Gly Gln Glu Cys Lys Asp
    130                 135                 140
```

Gly Glu Cys Pro Trp Gln Ala Leu Leu Ile Asn Glu Glu Asn Glu Gly
145                 150                 155                 160

Phe Cys Gly Gly Thr Ile Leu Ser Glu Phe Tyr Ile Leu Thr Ala Ala
                165                 170                 175

His Cys Leu Tyr Gln Ala Lys Arg Phe Lys Val Arg Val Gly Asp Arg
            180                 185                 190

Asn Thr Glu Gln Glu Glu Gly Gly Glu Ala Val His Glu Val Glu Val
        195                 200                 205

Val Ile Lys His Asn Arg Phe Thr Lys Glu Thr Tyr Asp Phe Asp Ile
210                 215                 220

Ala Val Leu Arg Leu Lys Thr Pro Ile Thr Phe Arg Met Asn Val Ala
225                 230                 235                 240

Pro Ala Cys Leu Pro Glu Arg Asp Trp Ala Glu Ser Thr Leu Met Thr
                245                 250                 255

Gln Lys Thr Gly Ile Val Ser Gly Phe Gly Arg Thr His Glu Lys Gly
            260                 265                 270

Arg Gln Ser Thr Arg Leu Lys Met Leu Glu Val Pro Tyr Val Asp Arg
        275                 280                 285

Asn Ser Cys Lys Leu Ser Ser Phe Ile Ile Thr Gln Asn Met Phe
290                 295                 300

Cys Ala Gly Tyr Asp Thr Lys Gln Glu Asp Ala Cys Gln Gly Asp Ala
305                 310                 315                 320

Gly Gly Pro His Val Thr Arg Phe Lys Asp Thr Tyr Phe Val Thr Gly
                325                 330                 335

Ile Val Ser Trp Gly Glu Gly Cys Ala Arg Lys Gly Lys Tyr Gly Ile
            340                 345                 350

Tyr Thr Lys Val Thr Ala Phe Leu Lys Trp Ile Asp Arg Ser Met Lys
        355                 360                 365

Thr Arg Gly Leu Pro Lys Ala Lys Ser His Ala Pro Glu Val Ile Thr
370                 375                 380

Ser Ser Pro Leu Lys
385

<210> SEQ ID NO 27
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Arg Leu Ala Val Gly Ala Leu Leu Val Cys Ala Val Leu Gly Leu
1               5                   10                  15

Cys Leu Ala Ala Asn Ser Phe Leu Phe Trp Asn Lys Tyr Lys Asp Gly
            20                  25                  30

Asp Gln Cys Glu Thr Ser Pro Cys Gln Asn Gly Lys Cys Lys Asp
        35                  40                  45

Gly Leu Gly Glu Tyr Thr Cys Thr Cys Leu Glu Gly Phe Glu Gly Lys
    50                  55                  60

Asn Cys Glu Leu Phe Thr Arg Lys Leu Cys Ser Leu Asp Asn Gly Asp
65                  70                  75                  80

Cys Asp Gln Phe Cys His Glu Glu Gln Asn Ser Val Val Cys Ser Cys
                85                  90                  95

Ala Arg Gly Tyr Thr Leu Ala Asp Asn Gly Lys Ala Cys Ile Pro Thr

```
                  100                 105                 110
Gly Pro Tyr Pro Cys Gly Lys Gln Thr Leu Glu Arg Arg Lys Arg Arg
            115                 120                 125

Lys Arg Ile Val Gly Gly Gln Glu Cys Lys Asp Gly Glu Cys Pro Trp
        130                 135                 140

Gln Ala Leu Leu Ile Asn Glu Glu Asn Glu Gly Phe Cys Gly Gly Thr
145                 150                 155                 160

Ile Leu Ser Glu Phe Tyr Ile Leu Thr Ala Ala His Cys Leu Tyr Gln
                165                 170                 175

Ala Lys Arg Phe Lys Val Arg Val Gly Asp Arg Asn Thr Glu Gln Glu
            180                 185                 190

Glu Gly Gly Glu Ala Val His Glu Val Glu Val Val Ile Lys His Asn
        195                 200                 205

Arg Phe Thr Lys Glu Thr Tyr Asp Phe Asp Ile Ala Val Leu Arg Leu
    210                 215                 220

Lys Thr Pro Ile Thr Phe Arg Met Asn Val Ala Pro Ala Cys Leu Pro
225                 230                 235                 240

Glu Arg Asp Trp Ala Glu Ser Thr Leu Met Thr Gln Lys Thr Gly Ile
                245                 250                 255

Val Ser Gly Phe Gly Arg Thr His Glu Lys Gly Arg Gln Ser Thr Arg
            260                 265                 270

Leu Lys Met Leu Glu Val Pro Tyr Val Asp Arg Asn Ser Cys Lys Leu
        275                 280                 285

Ser Ser Ser Phe Ile Ile Thr Gln Asn Met Phe Cys Ala Gly Tyr Asp
    290                 295                 300

Thr Lys Gln Glu Asp Ala Cys Gln Gly Asp Ala Gly Gly Pro His Val
305                 310                 315                 320

Thr Arg Phe Lys Asp Thr Tyr Phe Val Thr Gly Ile Val Ser Trp Gly
                325                 330                 335

Glu Gly Cys Ala Arg Lys Gly Lys Tyr Gly Ile Tyr Thr Lys Val Thr
            340                 345                 350

Ala Phe Leu Lys Trp Ile Asp Arg Ser Met Lys Thr Arg Gly Leu Pro
        355                 360                 365

Lys Ala Lys Ser His Ala Pro Glu Val Ile Thr Ser Ser Pro Leu Lys
    370                 375                 380

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agtctctaga cacagtactc ggccacacca tgggg                              35

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agctggatcc gagtgggatc tcactttaat ggagagg                            37
```

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gaggccagga atgcaaggac gg                                                22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccgtccttgc attcctggcc tc                                                22

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tcatcagcgt ggactcggcc cagt                                              24

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccaattcctt tcttttctgg aataaataca aagatggcga cc                          42

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttccagaaaa gaaaggaatt ggccctcgtg accc                                   34

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggaagaggag gaagaggatc gtgggaggcc aggaa                                  35

```
<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cacgatcctc ttcctcctct tcctgcgttc caggg                                 35

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37 aggggacgc aggggccccg cacgtcaccc                                        30

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gggtgacgtg cgggcccctg cttccccct                                        29

<210> SEQ ID NO 39
<211> LENGTH: 11
<212> TYPE: PRT
<213> ORGANISM: Homo sapiens

<400> SEQUENCE: 39

Arg Thr His Glu Lys Gly Arg Gln Ser Thr Arg
1               5                   10

<210> SEQ ID NO 40
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Lys Arg
1

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Lys Arg Arg Lys Arg
1               5

<210> SEQ ID NO 42
```

<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Asn Ser Phe Leu
1               5

<210> SEQ ID NO 43
<211> LENGTH: 405
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
                20                  25                  30

Asn Ile Leu Ala Arg Val Thr Arg Ala Asn Ser Phe Leu Phe Trp Asn
            35                  40                  45

Lys Tyr Lys Asp Gly Asp Gln Cys Glu Thr Ser Pro Cys Gln Asn Gln
        50                  55                  60

Gly Lys Cys Lys Asp Gly Leu Gly Glu Tyr Thr Cys Thr Cys Leu Glu
65                  70                  75                  80

Gly Phe Glu Gly Lys Asn Cys Glu Leu Phe Thr Arg Lys Leu Cys Ser
                85                  90                  95

Leu Asp Asn Gly Asp Cys Asp Gln Phe Cys His Glu Glu Gln Asn Ser
            100                 105                 110

Val Val Cys Ser Cys Ala Arg Gly Tyr Thr Leu Ala Asp Asn Gly Lys
        115                 120                 125

Ala Cys Ile Pro Thr Gly Pro Tyr Pro Cys Gly Lys Gln Thr Leu Glu
130                 135                 140

Arg Arg Lys Arg Arg Lys Arg Ile Val Gly Gly Gln Glu Cys Lys Asp
145                 150                 155                 160

Gly Glu Cys Pro Trp Gln Ala Leu Leu Ile Asn Glu Glu Asn Glu Gly
                165                 170                 175

Phe Cys Gly Gly Thr Ile Leu Ser Glu Phe Tyr Ile Leu Thr Ala Ala
            180                 185                 190

His Cys Leu Tyr Gln Ala Lys Arg Phe Lys Val Arg Val Gly Asp Arg
        195                 200                 205

Asn Thr Glu Gln Glu Glu Gly Gly Glu Ala Val His Glu Val Glu Val
    210                 215                 220

Val Ile Lys His Asn Arg Phe Thr Lys Glu Thr Tyr Asp Phe Asp Ile
225                 230                 235                 240

Ala Val Leu Arg Leu Lys Thr Pro Ile Thr Phe Arg Met Asn Val Ala
                245                 250                 255

Pro Ala Cys Leu Pro Glu Arg Asp Trp Ala Glu Ser Thr Leu Met Thr
            260                 265                 270

Gln Lys Thr Gly Ile Val Ser Gly Phe Gly Arg Thr His Glu Lys Gly
        275                 280                 285

Arg Gln Ser Thr Arg Leu Lys Met Leu Glu Val Pro Tyr Val Asp Arg
    290                 295                 300

-continued

```
Asn Ser Cys Lys Leu Ser Ser Phe Ile Ile Thr Gln Asn Met Phe
305                 310             315                 320

Cys Ala Gly Tyr Asp Thr Lys Gln Glu Asp Ala Cys Gln Gly Asp Ala
                325             330                 335

Gly Gly Pro His Val Thr Arg Phe Lys Asp Thr Tyr Phe Val Thr Gly
            340             345                 350

Ile Val Ser Trp Gly Glu Gly Cys Ala Arg Lys Gly Lys Tyr Gly Ile
            355             360             365

Tyr Thr Lys Val Thr Ala Phe Leu Lys Trp Ile Asp Arg Ser Met Lys
        370             375             380

Thr Arg Gly Leu Pro Lys Ala Lys Ser His Ala Pro Glu Val Ile Thr
385                 390             395                 400

Ser Ser Pro Leu Lys
            405
```

The invention claimed is:

1. An isolated two-chain polypeptide comprising:
   a first chain comprising amino acid residues 95-105 of SEQ ID NO: 20 or a first amino acid sequence having at least 95% sequence identity to amino acid residues 95-105 of SEQ ID NO: 20 and
   a second chain comprising amino acid residues 112-346 of SEQ ID NO: 20 or a second amino acid sequence having at least 95% sequence identity to amino acid residues 112-346 of SEQ ID NO: 20,
   wherein the polypeptide (a) has reduced catalytic activity as compared to the corresponding wild-type factor Xa protein, (b) is capable of binding to a factor Xa inhibitor and (c) cannot assemble into a prothrombinase complex, and
   wherein (i) the first chain does not include amino acid residues 12-50 of SEQ ID NO: 20, (ii) the first chain does not include amino acid residues 51-94 of SEQ ID NO: 20, or (iii) the second chain does not include amino acid residues 347-365 of SEQ ID NO: 6.

2. The polypeptide of claim 1, wherein the first chain does not include amino acid residues 6-39 of SEQ ID NO: 6.

3. The polypeptide of claim 2, wherein the first chain comprises amino acid residues 95-105 of SEQ ID NO: 20 and the second chain comprises amino acid residues 112-346 of SEQ ID NO: 20.

4. The polypeptide of claim 2, wherein the first chain comprises amino acid residues 51-105 of SEQ ID NO: 20 and the second chain comprises amino acid residues 112-346 of SEQ ID NO: 20.

5. The polypeptide of claim 2, wherein the first chain comprises amino acid residues 12-105 of SEQ ID NO: 20 and the second chain comprises amino acid residues 112-346 of SEQ ID NO: 20.

6. The polypeptide of claim 1, wherein the first amino acid sequence has at least 98% sequence identity to amino acid residues 95-105 of SEQ ID NO: 20, and the second amino acid sequence has at least 98% sequence identity to amino acid residues 112-346 of SEQ ID NO: 20.

7. The polypeptide of claim 1, wherein the first amino acid sequence has at least 99% sequence identity to amino acid residues 95-105 of SEQ ID NO: 20, and the second amino acid sequence has at least 99% sequence identity to amino acid residues 112-346 of SEQ ID NO: 20.

* * * * *